United States Patent
Albaugh et al.

(10) Patent No.: US 8,026,243 B2
(45) Date of Patent: Sep. 27, 2011

(54) [4,5']BIPYRIMIDINYL-6,4'-DIAMINE DERIVATIVES AS PROTEIN KINASE INHIBITORS

(75) Inventors: Pamela A. Albaugh, Emeryville, CA (US); Yun He, Shanghai (CN); Songchun Jiang, Emeryville, CA (US); Pingda Ren, Emeryville, CA (US); Xia Wang, Emeryville, CA (US); Xing Wang, Emeryville, CA (US); Yongping Xie, Emeryville, CA (US)

(73) Assignee: Novartis AG, Basel (CH)

( * ) Notice: Subject to any disclaimer, the term of this patent is extended or adjusted under 35 U.S.C. 154(b) by 179 days.

(21) Appl. No.: 12/373,441

(22) PCT Filed: Jul. 10, 2007

(86) PCT No.: PCT/US2007/073111
§ 371 (c)(1),
(2), (4) Date: Jan. 12, 2009

(87) PCT Pub. No.: WO2008/008747
PCT Pub. Date: Jan. 17, 2008

(65) Prior Publication Data
US 2010/0234376 A1 Sep. 16, 2010

Related U.S. Application Data

(60) Provisional application No. 60/830,492, filed on Jul. 12, 2006.

(51) Int. Cl.
*A01N 43/54* (2006.01)
*C07D 239/42* (2006.01)
*C07D 401/04* (2006.01)
*C07D 403/00* (2006.01)

(52) U.S. Cl. .................. 514/256; 544/296; 544/328

(58) Field of Classification Search .................. 514/256; 544/296, 328
See application file for complete search history.

(56) References Cited

FOREIGN PATENT DOCUMENTS

| WO | WO 01/29009 A1 | 4/2001 |
| WO | WO 2004/110350 A2 | 12/2004 |
| WO | WO 2005/033086 A1 | 4/2005 |
| WO | WO 2005/113494 A2 | 12/2005 |
| WO | WO 2007/092531 A2 | 8/2007 |

OTHER PUBLICATIONS

Cappellen D, De Oliveira C, Ricol D, de Medina S, Bourdin J, Sastre-Garau X, Chopin D, Thiery JP, Radvanyi F. Frequent activating mutations of FGFR3 in human bladder and cervix carcinomas. Nat Genet. Sep. 1999;23(1):18-20.*
Zhu L, Somlo G, Zhou B, Shao J, Bedell V, Slovak ML, Liu X, Luo J, Yen Y. Fibroblast growth factor receptor 3 inhibition by short hairpin RNAs leads to apoptosis in multiple myeloma. Mol Cancer Ther. May 2005;4(5):787-98.*
Zieger K, Dyrskjøt L, Wiuf C, Jensen JL, Andersen CL, Jensen KM, Ørntoft TFRole of activating fibroblast growth factor receptor 3 mutations in the development of bladder tumors. Clin Cancer Res. Nov. 1, 2005;11(21):7709-19.*

* cited by examiner

Primary Examiner — San-Ming Hui
Assistant Examiner — Paul Zarek

(57) ABSTRACT

The invention provides a novel class of compounds of the Formula I:

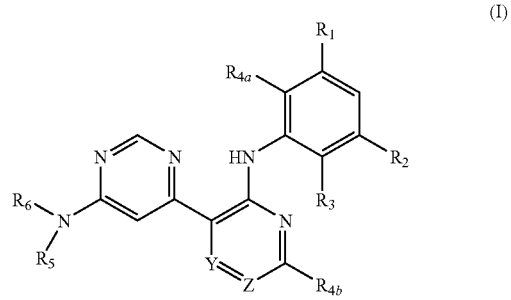

in which the symbols have the meanings given in the description and claims, to pharmaceutical compositions comprising such compounds and methods of using such compounds to treat or prevent diseases or disorders associated with abnormal or deregulated kinase activity, particularly diseases or disorders that involve abnormal activation of FGFR3 kinase.

19 Claims, No Drawings

[4,5']BIPYRIMIDINYL-6,4'-DIAMINE DERIVATIVES AS PROTEIN KINASE INHIBITORS

This application is a U.S. National Phase filing of International Application Serial No. PCT/US2007/073111 filed 10 Jul. 2007, and claims priority to U.S. Provisional Application Ser. No. 60/830,492 filed 12 Jul. 2006, the contents of which are incorporated herein by reference in their entirety.

BACKGROUND OF THE INVENTION

1. Field of the Invention

The invention provides a novel class of compounds, pharmaceutical compositions comprising such compounds and methods of using such compounds to treat or prevent diseases or disorders associated with abnormal or deregulated kinase activity, particularly diseases or disorders that involve aberrant activation of FGFR3 kinase.

2. Background

The protein kinases represent a large family of proteins, which play a central role in the regulation of a wide variety of cellular processes and maintaining control over cellular function. A partial, non-limiting, list of these kinases include: receptor tyrosine kinases such as Vascular Endothelial Growth Factor Receptor 2 kinase (VEGF-R2=KDR), platelet-derived growth factor receptor kinase (PDGF-R), the nerve growth factor receptor, trkB, Met, and the fibroblast growth factor receptor, FGFR3; non-receptor tyrosine kinases such Abl and the fusion kinase BCR-Abl, Lck, Csk, Fes, Bmx and c-src; and serine/threonine kinases such as b-RAF, c-RAF, sgk, MAP kinases (e.g., MKK4, MKK6, etc.) and SAPK2α, SAPK2β and SAPK3. Aberrant kinase activity has been observed in many disease states including benign and malignant proliferative disorders as well as diseases resulting from inappropriate activation of the immune and nervous systems.

The novel compounds of this invention inhibit the activity of one or more protein kinases and are, therefore, expected to be useful in the treatment of kinase-associated diseases.

SUMMARY OF THE INVENTION

In one aspect, the present invention provides compounds of Formula I:

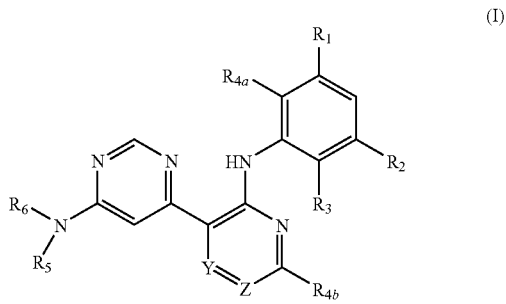

in which:
either Y is N and Z is CH or Z is N and Y is CH;
$R_1$ is $C_{1-4}$alkoxy;
$R_2$ is selected from cyano, $C_{1-4}$alkoxy, —C(O)NR$_7$R$_8$, —NR$_7$C(O)R$_8$, —NR$_7$S(O)$_2$R$_8$, —S(O)$_2$NR$_7$R$_8$, —NR$_7$R$_8$, —C(O)OR$_8$, —OC(O)R$_8$, —C(O)NR$_7$OR$_8$ and a saturated, unsaturated or partially saturated monocyclic ring containing 5 to 7 ring members selected from C, O, N and S; wherein $R_7$ is selected from hydrogen and $C_{1-4}$alkyl; and $R_8$ is selected from hydrogen, $C_{1-4}$alkyl and $C_{3-12}$cycloalkyl, or is phenyl that is unsubstituted or substituted by one or more substitutents selected from $C_1$-$C_4$-alkyl, halo-$C_1$-$C_4$-alkyl and (pyrrolidino, piperidino, piperazino or 4-$C_1$-$C_4$-alkylpiperazino)-$C_1$-$C_4$-alkyl;
or $R_1$ and $R_2$ are independently H when Y is N and Z is CH;
$R_3$ is selected from hydrogen, halo, $C_{1-4}$alkyl and $C_{1-4}$alkoxy;
$R_{4a}$ is selected from halo and $C_{1-4}$alkyl;
$R_{4b}$ is selected from hydrogen and $C_{1-4}$alkyl;
$R_5$ is hydrogen and $C_{1-4}$alkyl;
$R_6$ is selected from hydrogen, —X$_1$R$_9$, —C(O)NR$_{10}$X$_1$R$_9$ and X$_1$NR$_{10}$R$_{11}$; wherein each $X_1$ is independently selected from a bond and $C_{1-4}$alkylene; $R_9$ is selected from $C_{6-10}$aryl, a monocyclic ring containing 5 to 7 ring members selected from C, O, N and S, and a bridged or fused bicyclic ring system containing 8 to 14 members selected from C, O, N and S; wherein said monocyclic and bridged or fused bicyclic rings of $R_9$ can be saturated, unsaturated or partially unsaturated; $R_{10}$ and $R_{11}$ are independently selected from hydrogen and $C_{1-4}$alkyl;
wherein said aryl, monocyclic or bicyclic rings of $R_9$ can be optionally substituted with a group selected from $C_{1-4}$alkyl, —X$_2$R$_{12}$, and —OX$_2$NR$_{13}$R$_{14}$; wherein each $X_2$ is independently selected from a bond and $C_{1-4}$alkylene; $R_{13}$ and $R_{14}$ are independently selected from hydrogen and $C_{1-4}$alkyl; $R_{12}$ is selected from a monocyclic ring containing 5 to 7 ring members selected from C, O, N and S optionally substituted with up to 3 groups selected from $C_{1-4}$alkyl, —X$_3$C(O)NR$_{15}$R$_{16}$, —X$_3$OR$_{16}$, —X$_3$C(O)X$_3$OR$_{15}$, —X$_3$C(O)R$_{15}$ and —X$_3$NR$_{15}$R$_{16}$; wherein said monocyclic ring of $R_{12}$ can be saturated, unsaturated or partially unsaturated; wherein each $X_3$ is independently selected from a bond and $C_{1-4}$alkylene; each $R_{15}$ and $R_{16}$ is independently selected from hydrogen and $C_{1-4}$alkyl;
wherein any alkyl substituents of $R_9$ can optionally substituted with up to 3 hydroxyl groups; the N-oxide derivatives, prodrug derivatives, protected derivatives, individual isomers and mixture of isomers thereof; and/or the pharmaceutically acceptable salts and solvates (e.g. hydrates) of such compounds.

In a second aspect, the present invention provides a pharmaceutical composition which contains a compound of Formula I or an N-oxide derivative, an individual isomer, a mixture of isomers; and/or a pharmaceutically acceptable salt thereof, in admixture with one or more suitable (pharmaceutically acceptable) excipients.

In a third aspect, the present invention provides a method of treating a disease in an animal in which inhibition of kinase activity, particularly FGFR3 activity, can prevent, inhibit or ameliorate the pathology and/or symptomology of the diseases, which method comprises administering to the animal a therapeutically effective amount of a compound of Formula I or a N-oxide derivative, an individual isomer, a mixture of isomers, and/or a pharmaceutically acceptable salt thereof.

In a fourth aspect, the present invention provides the use of a compound of Formula I, an N-oxide derivative, an individual isomer, a mixture of isomers, or a pharmaceutically acceptable salt thereof, in the manufacture of a medicament for treating a disease in an animal in which kinase activity, particularly FGFR3 activity, contributes to the pathology and/or symptomology of the disease.

In a fifth aspect, the present invention provides a process for preparing compounds of Formula I, the N-oxide derivatives, prodrug derivatives, protected derivatives, individual isomers, mixtures of isomers thereof, and/or the pharmaceutically acceptable salts thereof.

In an eighth aspect, the invention provides for a compound of the Formula I, an N-oxide derivative, an individual isomer, a mixture of isomers, or a pharmaceutically acceptable salt thereof, for use in the treatment of the animal (including human) body, especially for treating a disease in an animal in which inhibition of kinase activity, particularly FGFR3 activity, can prevent, inhibit or ameliorate the pathology and/or symptomology of the disease, or for use in the preparation of a pharmaceutical composition useful in the treatment of said disease.

DETAILED DESCRIPTION OF THE INVENTION

Definitions

"Alkyl" as a group and as a structural element of other groups, for example halo-substituted-alkyl and alkoxy, can be either straight-chained or branched. $C_{1-4}$-alkoxy includes, methoxy, ethoxy, and the like. Halo-substituted alkyl includes trifluoromethyl, pentafluoroethyl, and the like.

"Aryl" means a monocyclic or fused bicyclic aromatic ring assembly containing six to ten ring carbon atoms. For example, aryl may be phenyl or naphthyl, preferably phenyl. "Arylene" means a divalent radical derived from an aryl group.

"a saturated, unsaturated or partially saturated monocyclic ring containing 5 to 7 ring members selected from C, O, N and S" includes, for example, pyridyl, indolyl, imidazolyl, pyrimidinyl, furanyl, oxazolyl, isoxazolyl, triazolyl, tetrazolyl, pyrazolyl, thienyl, morpholino, pyrrolidinyl, pyrrolidinyl-2-one, piperazinyl, piperidinyl, piperidinylone, etc.

The term "a bridged or fused bicyclic ring system containing 8 to 14 members selected from C, O, N and S (can be saturated, unsaturated or partially saturated) includes, for example, indazolyl, quinoxalinyl, quinolinyl, benzofuranyl, benzopyranyl, benzothiopyranyl, benzo[1,3]dioxole, benzoimidazolyl, 1,4-dioxa-8-aza-spiro[4.5]dec-8-yl, etc.

"Cycloalkyl" means a saturated or partially unsaturated, monocyclic, fused bicyclic or bridged polycyclic ring assembly containing the number of ring atoms indicated. For example, $C_{3-10}$cycloalkyl includes cyclopropyl, cyclobutyl, cyclopentyl, cyclohexyl, etc.

"Halogen" (or halo) preferably represents chloro or fluoro, but may also be bromo or iodo.

"Kinase Panel" is a list of kinases comprising Abl(human), Abl(T315I), JAK2, JAK3, ALK, JNK1α1, ALK4, KDR, Aurora-A, Lck, Blk, MAPK1, Bmx, MAPKAP-K2, B-Raf, BRK, MEK1, CaMKII(rat), Met, CDK1/cyclinB, p70S6K, CHK2, PAK2, CK1, PDGFRα, CK2, PDK1, c-kit, Pim-2, c-RAF, PKA(h), CSK, PKBα, cSrc, PKCα, DYRK2, Plk3, EGFR, ROCK-I, Fes, Ron, FGFR3, Ros, Flt3, SAPK2α, Fms, SGK, Fyn, SIK, GSK3β, Syk, IGF-1R, Tie-2, IKKβ, TrKB, IR, WNK3, IRAK4, ZAP-70, ITK, AMPK(rat), LIMK1, Rsk2, Axl, LKB1, SAPK2β, BrSK2, Lyn (h), SAPK3, BTK, MAPKAP-K3, SAPK4, CaMKIV, MARK1, Snk, CDK2/cyclinA, MINK, SRPK1, CDK3/cyclinE, MKK4(m), TAK1, CDK5/p25, MKK6(h), TBK1; CDK6/cyclinD3, MLCK, TrKA, CDK7/cyclinH/MAT1, MRCKβ, TSSK1, CHK1, MSK1, Yes, CK1d, MST2, ZIPK, c-Kit (D816V), MuSK, DAPK2, NEK2, DDR2, NEK6, DMPK, PAK4, DRAK1, PAR-1Bα, EphA1, PDGFRβ, EphA2, Pim-1, EphA5, PKBβ, EphB2, PKCβI, EphB4, PKCδ, FGFR1, PKCη, FGFR2, PKCθ, FGFR4, PKD2, Fgr, PKG1β, Flt1, PRK2, Hck, PYK2, HIPK2, Ret, IKKα, RIPK2, IRR, ROCK-II(human), JNK2α2, Rse, JNK3, Rsk1(h), PI3 Kγ, PI3 Kδ and PI3-Kβ. Compounds of the invention are screened against the kinase panel (wild type and/or mutation thereof) and inhibit the activity of at least one of said panel members.

"Mutant forms of BCR-Abl" means single or multiple amino acid changes from the wild-type sequence. Mutations in BCR-ABL act by disrupting critical contact points between protein and inhibitor (for example, Gleevec, and the like), more often, by inducing a transition from the inactive to the active state, i.e. to a conformation to which BCR-ABL and Gleevec is unable to bind. From analyses of clinical samples, the repertoire of mutations found in association with the resistant phenotype has been increasing slowly but inexorably over time. Mutations seem to cluster in four main regions. One group of mutations (G250E, Q252R, Y253F/H, E255K/V) includes amino acids that form the phosphate-binding loop for ATP (also known as the P-loop). A second group (V289A, F311L, T315I, F317L) can be found in the Gleevec binding site and interacts directly with the inhibitor via hydrogen bonds or Van der Waals' interactions. The third group of mutations (M351T, E355G) clusters in close proximity to the catalytic domain. The fourth group of mutations (H396R/P) is located in the activation loop, whose conformation is the molecular switch controlling kinase activation/inactivation. BCR-ABL point mutations associated with Gleevec resistance detected in CML and ALL patients include: M224V, L248V, G250E, G250R, Q252R, Q252H, Y253H, Y253F, E255K, E255V, D276G, T277A, V289A, F311L, T315I, T315N, F317L, M343T, M315T, E355G, F359V, F359A, V379I, F382L, L387M, L387F, H396P, H396R, A397P, S417Y, E459K, and F486S (Amino acid positions, indicated by the single letter code, are those for the GenBank sequence, accession number AAB60394, and correspond to ABL type 1a; Martinelli et al., Haematologica/The Hematology Journal, 2005, April; 90-4). Unless otherwise stated for this invention, Bcr-Abl refers to wild-type and mutant forms of the enzyme.

"Treat", "treating" and "treatment" refer to a method of alleviating or abating a disease and/or its attendant symptoms.

DESCRIPTION OF THE PREFERRED EMBODIMENTS

The present invention provides compounds, compositions and methods for the treatment of kinase related disease, particularly FGFR3 kinase related diseases. For example, bladder cancer, multiple myeloma and other cancers associated with FRFR3 overexpression or mutation can be treated through the inhibition of FGFR3.

In one embodiment, with reference to compounds of Formula I, either Y is N and Z is CH or Z is N and Y is CH, either of these variants independently being a preferred embodiment of the invention.

In another embodiment, $R_1$ is $C_{1-4}$alkoxy; $R_2$ is selected from cyano, $C_{1-4}$alkoxy, $-C(O)NR_7R_8$, $-NR_7C(O)R_8$, $-NR_7S(O)_2R_8$, $-NR_7R_8$, $-C(O)OR_8$, $-C(O)NR_7OR_8$ and a saturated, unsaturated or partially saturated monocyclic ring containing 5 to 7 ring members selected from C, O, N and S, or $R_1$ and $R_2$ are independently H when Y is N and Z is CH; wherein $R_7$ is selected from hydrogen and $C_{1-4}$alkyl; and $R_8$ is selected from hydrogen, $C_{1-4}$alkyl and $C_{3-12}$cycloalkyl.

In another embodiment, $R_3$ is selected from hydrogen, halo and $C_{1-4}$alkyl; $R_{4a}$ is selected from halo and $C_{1-4}$alkyl; $R_{4b}$ is selected from hydrogen and $C_{1-4}$alkyl; and $R_5$ is hydrogen.

In another embodiment, $R_6$ is selected from hydrogen, $-X_1R_9$, $-C(O)NR_{10}X_1R_9$ and $X_1NR_{10}R_{11}$; wherein each $X_1$ is independently selected from a bond and $C_{1-4}$alkylene; $R_9$ is selected from $C_{6-10}$aryl, a monocyclic ring containing 5 to 7 ring members selected from C, O, N and S, and a bridged or fused bicyclic ring system containing 8 to 14 members selected from C, O, N and S; wherein said monocyclic and bridged or fused bicyclic rings of $R_9$ can be saturated, unsaturated or partially unsaturated; $R_{10}$ and $R_{11}$ are independently selected from hydrogen and $C_{1-4}$alkyl; wherein said monocyclic and bridged or fused bicyclic rings of $R_9$ can be optionally substituted with a group selected from $C_{1-4}$alkyl, $-X_2R_{12}$, and $-OX_2NR_{13}R_{14}$; wherein each $X_2$ is independently selected from a bond and $C_{1-4}$alkylene; $R_{13}$ and $R_{14}$ are independently selected from hydrogen and $C_{1-4}$alkyl; $R_{12}$ is selected from a monocyclic ring containing 5 to 7 ring members selected from C, O, N and S optionally substituted with up to 3 groups selected from $C_{1-4}$alkyl, $-X_3C(O)NR_{15}R_{16}$, $-X_3OR_{16}$, $-X_3C(O)X_3OR_{15}$, $-X_3C(O)R_{15}$ and $-X_3NR_{15}R_{16}$; wherein said monocyclic and bridged or fused bicyclic rings of $R_{12}$ can be saturated, unsaturated or partially unsaturated; wherein each $X_3$ is independently selected from a bond and $C_{1-4}$alkylene; each $R_{15}$ and $R_{16}$ is independently selected from hydrogen and $C_{1-4}$alkyl; wherein any alkyl substituents of $R_9$ can optionally substituted with up to 3 hydroxyl groups.

In another embodiment, $R_1$ is methoxy; and $R_2$ is selected from cyano, methoxy, ethyl-amino-carbonyl, cyclopropyl-amino-carbonyl, cyclopropyl-carbonyl-amino, methyl-carbonyl-amino, methyl-sulfonyl-amino, amino, methoxy-carbonyl, ethoxy-amino-carbonyl and amino-carbonyl; or $R_1$ and $R_2$ are independently H when Y is N and Z is CH.

In another embodiment, $R_3$ is selected from hydrogen, chloro, fluoro, bromo and methyl; $R_{4a}$ is selected from chloro, fluoro, methyl and oxazole; $R_{4b}$ is selected from hydrogen and methyl; and $R_5$ is hydrogen.

In another embodiment, $R_6$ is selected from: hydrogen; morpholino-ethyl; morpholino-ethyl-aminocarbonyl; dimethyl-amino-butyl; methyl-piperazinyl-ethyl; methyl-piperazinyl-ethyl-aminocarbonyl; pyridinyl substituted with a group selected from 1-hydroxyethyl or especially morpholino-methyl, amino-carbonyl-piperazinyl-methyl, methyl-carbonyl-piperazinyl-methyl, morpholino-ethyl, piperidinyl-methyl, pyrrolidinyl-methyl, dimethylamino-carbonyl-piperazinyl-methyl, methylamino-carbonyl-piperazinyl-methyl, methyl-piperazinyl-methyl, ethyl-piperazinyl-methyl, hydroxy-ethyl-piperazinyl-methyl, ethyl-piperazinyl, methyl-piperazinyl-ethyl, hydroxy-methyl-carbonyl-piperazinyl, diethyl-amino-methyl and dimethyl-amino-methyl; and phenyl substituted with a group selected from ethyl-piperazinyl, 1-hydroxy-ethyl, morpholino-methyl, diethylamino-ethoxy and morpholino, or is phenyl that is substituted with piperazinyl-$C_1$-$C_4$-alkyl that is unsubstituted or substituted with $C_1$-$C_4$-alkyl.

In another embodiment, $R_2$ is $-C(O)NR_7OR_8$ wherein $R_7$ is hydrogen or $C_1$-$C_4$-alkyl and $R_8$ is selected from (halo-$C_1$-$C_4$-alkyl)-phenyl, such as 3-trifluoromethyl, or 4-[4-($C_1$-$C_4$-alkyl)-piperazin-1-yl-$C_1$-$C_4$-alkyl]-3-(halo-$C_1$-$C_4$-alkyl)-phenyl, such as 4-(4-ethylpiperazin-1-yl-methyl)-3-trifluoromethyl.

In another embodiment, are compounds of Formula I selected from N4'-(2,6-Dichloro-3,5-dimethoxy-phenyl)-[4,5']bipyrimidinyl-6,4'-diamine, N4'-(2,6-Dichloro-3,5-dimethoxy-phenyl)-N6-(5-pyrrolidin-1-ylmethyl-pyridin-2-yl)-[4,5']bipyrimidinyl-6,4'-diamine, N4'-(2,6-Dichloro-3,5-dimethoxy-phenyl)-N6-[5-(4-methyl-piperazin-1-ylmethyl)-pyridin-2-yl]-[4,5']bipyrimidinyl-6,4'-diamine, N4'-(2,6-Dichloro-3,5-dimethoxy-phenyl)-N6-(5-morpholin-4-ylmethyl-pyridin-2-yl)-[4,5']bipyrimidinyl-6,4'-diamine, N4'-(2,6-Dichloro-3,5-dimethoxy-phenyl)-N6-(4-morpholin-4-ylmethyl-pyridin-2-yl)-[4,5']bipyrimidinyl-6,4'-diamine, N4'-(2,6-Dichloro-3,5-dimethoxy-phenyl)-N6-[4-(4-methyl-piperazin-1-ylmethyl)-pyridin-2-yl]-[4,5']bipyrimidinyl-6,4'-diamine, N4'-(2,6-Dichloro-3,5-dimethoxy-phenyl)-N6-(5-dimethylaminomethyl-pyridin-2-yl)-[4,5']bipyrimidinyl-6,4'-diamine, 1-[4'-(2,6-Dichloro-3,5-dimethoxy-phenylamino)-[4,5']bipyrimidinyl-6-yl]-3-[2-(4-methyl-piperazin-1-yl)-ethyl]-urea, 1-[4'-(2,6-Dichloro-3,5-dimethoxy-phenylamino)-[4,5']bipyrimidinyl-6-yl]-3-(2-morpholin-4-yl-ethyl)-urea, N4'-(2,6-Dichloro-3,5-dimethoxy-phenyl)-N6-[4-(4-ethyl-piperazin-1-yl)-phenyl]-[4,5']bipyrimidinyl-6,4'-diamine, N4'-(2,6-Dichloro-3,5-dimethoxy-phenyl)-N6-(4-morpholin-4-yl-phenyl)-[4,5']bipyrimidinyl-6,4'-diamine, N4'-(2,6-Dichloro-3,5-dimethoxy-phenyl)-N6-(3-morpholin-4-yl-propyl)-[4,5']bipyrimidinyl-6,4'-diamine, N4'-(2,6-Dichloro-3,5-dimethoxy-phenyl)-N6-(4-dimethylamino-butyl)-[4,5']bipyrimidinyl-6,4'-diamine, N4'-(2,6-Dichloro-3,5-dimethoxy-phenyl)-N6-[2-(4-methyl-piperazin-1-yl)-ethyl]-[4,5']bipyrimidinyl-6,4'-diamine, 4-{6-[4'-(2,6-Dichloro-3,5-dimethoxy-phenylamino)-[4,5']bipyrimidinyl-6-ylamino]-pyridin-3-ylmethyl}-piperazine-1-carboxylic acid amide, 1-(4-{6-[4'-(2,6-Dichloro-3,5-dimethoxy-phenylamino)-[4,5']bipyrimidinyl-6-ylamino]-pyridin-3-ylmethyl}-piperazin-1-yl)-ethanone, N4'-(2,6-Dichloro-3,5-dimethoxy-phenyl)-N6-[4-(2-diethylamino-ethoxy)-phenyl]-[4,5']bipyrimidinyl-6,4'-diamine, N4'-(2,6-Dichloro-3,5-dimethoxy-phenyl)-N6-[5-(2-morpholin-4-yl-ethyl)-pyridin-2-yl]-[4,5']bipyrimidinyl-6,4'-diamine, 4-{6-[4'-(2,6-Dichloro-3,5-dimethoxy-phenylamino)-[4,5']bipyrimidinyl-6-ylamino]-pyridin-3-ylmethyl}-piperazine-1-carboxylic acid dimethyl-amide, 4-{6-[4'-(2,6-Dichloro-3,5-dimethoxy-phenylamino)-[4,5']bipyrimidinyl-6-ylamino]-pyridin-3-ylmethyl}-piperazine-1-carboxylic acid methylamide, N4'-(2,6-Dichloro-3,5-dimethoxy-phenyl)-N6-(5-morpholin-4-ylmethyl-pyridin-3-yl)-[4,5']bipyrimidinyl-6,4'-diamine, N4'-(2,6-Dichloro-3,5-dimethoxy-phenyl)-N6-(5-piperidin-1-ylmethyl-pyridin-2-yl)-[4,5']bipyrimidinyl-6,4'-diamine, 3-(6-Amino-[4,5']bipyrimidinyl-4'-ylamino)-2,4-dichloro-5-methoxy-benzoic acid methyl ester, 2,4-Dichloro-N-ethyl-5-methoxy-3-[6-(5-morpholin-4-ylmethyl-pyridin-2-ylamino)-[4,5']bipyrimidinyl-4'-ylamino]-benzamide, 2,4-Dichloro-N-ethoxy-5-methoxy-3-[6-(5-morpholin-4-ylmethyl-pyridin-2-ylamino)-[4,5']bipyrimidinyl-4'-ylamino]-benzamide, 2,4-Dichloro-5-methoxy-3-[6-(5-morpholin-4-yl-methyl-pyridin-2-ylamino)-[4,5']bipyrimidinyl-4'-ylamino]-benzamide, 2,4-Dichloro-5-methoxy-3-[6-(5-morpholin-4-ylmethyl-pyridin-2-ylamino)-[4,5']bipyrimidinyl-4'-ylamino]-benzoic acid methyl ester, N4'-(2,6-Dichloro-3,5-dimethoxy-phenyl)-N6-(5-diethylamino-methyl-pyridin-2-yl)-[4,5']bipyrimidinyl-6,4'-diamine, 1-{3-[4'-(2,6-Dichloro-3,5-dimethoxy-phenylamino)-[4,5']bipyrimidinyl-6-ylamino]-phenyl}-ethanol, 2,4-Dichloro-N-ethyl-5-methoxy-3-{6-[4-(4-methyl-piperazin-1-ylmethyl)-pyridin-2-ylamino]-[4,5']bipyrimidinyl-4'-ylamino}-benzamide, 2,4-Dichloro-3-[6-(5-dimethylaminomethyl-pyridin-2-ylamino)-[4,5']bipyrimidinyl-4'-ylamino]-N-ethyl-5-methoxy-benzamide, 2,4-Dichloro-N-ethyl-5-methoxy-3-{6-[5-(2-morpholin-4-yl-ethyl)-pyridin-2-ylamino]-[4,5']bipyrimidinyl-4'-yl-amino}-benzamide, 2,4-Dichloro-N-ethyl-5-methoxy-3-[6-(4-morpholin-4-ylmethyl-pyridin-2-ylamino)-[4,5']bipyrimidinyl-4'-ylamino]-benzamide, 2,4-Dichloro-N-ethyl-5-methoxy-3-{6-[5-(4-methyl-piperazin-1-ylmethyl)-pyridin-2-ylamino]-[4,5']bipyrimidinyl-4'-ylamino}-benzamide, 2,4-Dichloro-N-ethyl-5-methoxy-3-[6-(5-pyrrolidin-1-ylmethyl-pyridin-2-ylamino)-[4,5']bipyrimidinyl-4'-ylamino]-benzamide, 2,4-Dichloro-N-ethyl-3-{6-[4-(4-ethyl-piperazin-1-yl)-phenylamino]-[4,5']bipyrimidinyl-4'-ylamino}-5-methoxy-benzamide, N4'-(2-Chloro-3,5-dimethoxy-phenyl)-N6-(5-morpholin-4-ylmethyl-pyridin-2-yl)-[4,5']bipyrimidinyl-6,4'-diamine, N4'-(2-Chloro-3,5-dimethoxy-phenyl)-N6-[5-(4-ethyl-piperazin-1-ylmethyl)-pyridin-2-yl]-[4,5']bipyrimidinyl-6,4'-diamine, N4'-(2-Chloro-3,5-dimethoxy-phenyl)-N6-[4-(4- methyl-piperazin-1-ylmethyl)-pyridin-2-yl]-[4,5']bipyrimidinyl-6,4'-diamine, N4'-(2,6-Dichloro-3,5-dimethoxy-phenyl)-N6-[5-(4-ethyl-piperazin-1-yl)-pyridin-2-yl]-[4,5']bipyrimidinyl-6,4'-diamine, 2,4-Dichloro-3-{6-[5-(4-ethyl-piperazin-1-yl)-pyridin-2-ylamino]-[4,5']bipyrimidinyl-4'-ylamino}-5-methoxy-benzoic acid methyl ester, 2,4-Dichloro-N-ethyl-3-{6-[5-(4-ethyl-piperazin-1-yl)-pyridin-2-ylamino]-[4,5']bipyrimidinyl-4'-ylamino}-5-methoxy-benzamide, N4'-(2-Chloro-6-fluoro-3,5-dimethoxy-phenyl)-N6-[5-(4-ethyl-piperazin-1-yl)-pyridin-2-yl]-[4,5']bipyrimidinyl-6,4'-diamine, N4'-(2-Chloro-6-fluoro-3,5-dimethoxy-phenyl)-N6-(5-morpholin-4-ylmethyl-pyridin-2-yl)-[4,5']bipyrimidinyl-6,4'-diamine, N4'-(2-Chloro-6-fluoro-3,5-dimethoxy-phenyl)-N6-[5-(4-ethyl-piperazin-1-ylmethyl)-pyridin-2-yl]-[4,5']bipyrimidinyl-6,4'-diamine, N4'-(2-Chloro-6-fluoro-3,5-dimethoxy-phenyl)-N6-(4-morpholin-4-ylmethyl-pyridin-2-yl)-[4,5']bipyrimidinyl-6,4'-diamine, N4'-(2-Bromo-6-chloro-3,5-dimethoxy-phenyl)-N6-[5-(4-ethyl-piperazin-1-yl)-pyridin-2-yl]-[4,5']bipyrimidinyl-6,4'-diamine, N4'-(2-Chloro-3,5-di-methoxy-6-methyl-phenyl)-N6-[5-(4-ethyl-piperazin-1-yl)-pyridin-2-yl]-[4,5']bipyrimidinyl-6,4'-diamine, N4'-(2-Bromo-6-chloro-3,5-dimethoxy-phenyl)-N6-(5-morpholin-4-ylmethyl-pyridin-2-yl)-[4,5']bipyrimidinyl-6,4'-diamine, N4'-(2-Bromo-6-chloro-3,5-dimethoxy-phenyl)-N6-[5-(4-ethyl-piperazin-1-ylmethyl)-pyridin-2-yl]-[4,5']bipyrimidinyl-6,4'-diamine, N4'-(2-Bromo-6-chloro-3,5-dimethoxy-phenyl)-N6-(4-morpholin-4-ylmethyl-pyridin-2-yl)-[4,5']bipyrimidinyl-6,4'-diamine, N4'-(2-Chloro-3,5-dimethoxy-6-methyl-phenyl)-N6-(5-morpholin-4-ylmethyl-pyridin-2-yl)-[4,5']bipyrimidinyl-6,4'-diamine, N4'-(2-Chloro-3,5-dimethoxy-6-methyl-phenyl)-N6-[5-(4-ethyl-piperazin-1-ylmethyl)-pyridin-2-yl]-[4,5']bipyrimidinyl-6,4'-diamine, N4'-(2-Chloro-3,5-dimethoxy-6-methyl-phenyl)-N6-(4-morpholin-4-ylmethyl-pyridin-2-yl)-[4,5']bipyrimidinyl-6,4'-diamine, 2,4-Dichloro-N-cyclopropyl-3-{6-[5-(4-ethyl-piperazin-1-yl)-pyridin-2-ylamino]-[4,5']bipyrimidinyl-4'-ylamino}-5-methoxy-benzamide, N4'-(2-Chloro-6-fluoro-3,5-dimethoxy-phenyl)-N6-[4-(2-morpholin-4-yl-ethyl)-pyridin-2-yl]-[4,5']bipyrimidinyl-6,4'-diamine, 2,4-Dichloro-N-cyclopropyl-5-methoxy-3-[6-(5-morpholin-4-ylmethyl-pyridin-2-ylamino)-[4,5']bipyrimidinyl-4'-ylamino]-benzamide, 2,4-Dichloro-N-cyclopropyl-3-{6-[5-(4-ethyl-piperazin-1-ylmethyl)-pyridin-2-ylamino]-[4,5']bipyrimidinyl-4'-ylamino}-5-methoxy-benzamide, N4'-(2-Chloro-6-fluoro-3,5-di-methoxy-phenyl)-N6-[4-(4-ethyl-piperazin-1-yl)-phenyl]-[4,5']bipyrimidinyl-6,4'-diamine, N4'-(2-Chloro-6-fluoro-3,5-dimethoxy-phenyl)-N6-(4-pyrrolidin-1-ylmethyl-pyridin-2-yl)-[4,5']bipyrimidinyl-6,4'-diamine, 1-(4-{6-[4'-(2-Chloro-6-fluoro-3,5-dimethoxy-phenylamino)-[4,5']bipyrimidinyl-6-ylamino]-pyridin-3-ylmethyl}-piperazin-1-yl)-ethanone, N4'-(2,6-Difluoro-3,5-dimethoxy-phenyl)-N6-[5-(4-ethyl-piperazin-1-yl)-pyridin-2-yl]-[4,5']bipyrimidinyl-6,4'-diamine, N4'-(2,6-Difluoro-3,5-dimethoxy-phenyl)-N6-(5-morpholin-4-ylmethyl-pyridin-2-yl)-[4,5']bipyrimidinyl-6,4'-diamine, N4'-(2,6-Difluoro-3,5-dimethoxy-phenyl)-N6-[5-(4-ethyl-piperazin-1-ylmethyl)-pyridin-2-yl]-[4,5']bipyrimidinyl-6,4'-diamine, N4'-(2,6-Difluoro-3,5-dimethoxy-phenyl)-N6-(4-morpholin-4-ylmethyl-pyridin-2-yl)-[4,5']bipyrimidinyl-6,4'-diamine, 1-(4-{6-[4'-(2,6-Difluoro-3,5-dimethoxy-phenylamino)-[4,5']bipyrimidinyl-6-ylamino]-pyridin-3-ylmethyl}-piperazin-1-yl)-ethanone, 3-{6-[5-(4-Acetyl-piperazin-1-ylmethyl)-pyridin-2-ylamino]-[4,5']bipyrimidinyl-4'-ylamino}-2,4-dichloro-N-cyclopropyl-5-methoxy-benzamide, N4'-(2-Fluoro-3,5-dimethoxy-phenyl)-N6-(5-morpholin-4-ylmethyl-pyridin-2-yl)-[4,5']bipyrimidinyl-6,4'-diamine, N6-[5-(4-Ethyl-piperazin-1-ylmethyl)-pyridin-2-yl]-N4'-(2-fluoro-3,5-dimethoxy-phenyl)-[4,5']bipyrimidinyl-6,4'-diamine, 2-(4-{6-[4'-(2-Fluoro-3,5-dimethoxy-phenylamino)-[4,5']bipyrimidinyl-6-ylamino]-pyridin-3-ylmethyl}-piperazin-1-yl)-ethanol, N4'-(2-Fluoro-3,5-dimethoxy-phenyl)-N6-(4-morpholin-4-ylmethyl-pyridin-2-yl)-[4,5']bipyrimidinyl-6,4'-diamine, N6-[5-(4-Ethyl-piperazin-1-yl)-pyridin-2-yl]-N4'-(2-fluoro-3,5-dimethoxy-phenyl)-[4,5']bipyrimidinyl-6,4'-diamine, 2-(4-{6-[4'-(2-Chloro-6-fluoro-3,5-dimethoxy-phenylamino)-[4,5']bipyrimidinyl-6-ylamino]-pyridin-3-ylmethyl}-piperazin-1-yl)-ethanol, 2-(4-{6-[4'-(2,6-Difluoro-3,5-dimethoxy-phenylamino)-[4,5']bipyrimidinyl-6-ylamino]-pyridin-3-ylmethyl}-piperazin-1-yl)-ethanol, 2-(4-{6-[4'-(2,6-Dichloro-3,5-dimethoxy-phenylamino)-[4,5']bipyrimidinyl-6-yl-amino]-pyridin-3-ylmethyl}-piperazin-1-yl)-ethanol, 2-(4-{6-[4'-(2-Chloro-3,5-dimethoxy-6-methyl-phenylamino)-[4,5']bipyrimidinyl-6-ylamino]-pyridin-3-ylmethyl}-piperazin-1-yl)-ethanol, 1-{3-[4'-(2-Chloro-6-fluoro-3,5-dimethoxy-phenylamino)-[4,5']bipyrimidinyl-6-yl-amino]-phenyl}-ethanol, 1-{3-[4'-(2,6-Difluoro-3,5-dimethoxy-phenylamino)-[4,5']bipyrimidinyl-6-ylamino]-phenyl}-ethanol, 1-{6-[4'-(2-Chloro-6-fluoro-3,5-dimethoxy-phenylamino)-[4,5']bipyrimidinyl-6-ylamino]-pyridin-3-yl}-ethanol, 1-{6-[4'-(2,6-Difluoro-3,5-dimethoxy-phenylamino)-[4,5']bipyrimidinyl-6-ylamino]-pyridin-3-yl}-ethanol, 1-{6-[4'-(2-Chloro-3,5-dimethoxy-6-methyl-phenylamino)-[4,5']bipyrimidinyl-6-ylamino]-pyridin-3-yl}-ethanol, 1-{6-[4'-(2,6-Dichloro-3,5-dimethoxy-phenylamino)-[4,5']bipyrimidinyl-6-ylamino]-pyridin-3-yl}-ethanol, 1-{6-[4'-(2-Fluoro-3,5-dimethoxy-phenylamino)-[4,5']bipyrimidinyl-6-ylamino]-pyridin-3-yl}-ethanol, N4'-(2-Fluoro-3,5-dimethoxy-phenyl)-N6-[5-(2-morpholin-4-yl-ethyl)-pyridin-2-yl]-[4,5']bipyrimidinyl-6,4'-diamine, N4'-(2,6-Difluoro-3,5-dimethoxy-phenyl)-N6-[5-(2-morpholin-4-yl-ethyl)-pyridin-2-yl]-[4,5']bipyrimidinyl-6,4'-diamine, N4'-(2-Chloro-3,5-dimethoxy-6-methyl-phenyl)-N6-[5-(2-morpholin-4-yl-ethyl)-pyridin-2-yl]-[4,5']bipyrimidinyl-6,4'-diamine, 1-(4-{6-[4'-(2,6-Dichloro-3,5-dimethoxy-phenylamino)-[4,5']bipyrimidinyl-6-ylamino]-pyridin-3-ylmethyl}-piperazin-1-yl)-2-hydroxy-ethanone, 1-(4-{6-[4'-(2-Chloro-6-fluoro-3,5-dimethoxy-phenylamino)-[4,5']bipyrimidinyl-6-ylamino]-pyridin-3-ylmethyl}-piperazin-1-yl)-2-hydroxy-ethanone, and N4'-(2-Chloro-6-fluoro-3,5-dimethoxy-phenyl)-2'-methyl-N6-(5-morpholin-4-ylmethyl-pyridin-2-yl)-[4,5']bipyrimidinyl-6,4'-diamine.

Further preferred compounds according to the invention are selected from the group consisting of 2,4-dichloro-5-methoxy-3-(6-(5-(morpholinomethyl)pyridin-2-ylamino)-4,5'-bipyrimidin-4'-ylamino)-N-(3-(trifluoromethyl)phenyl)benzamide, 2,4-dichloro-N-(4-((4-ethylpiperazin-1-yl)methyl)-3-(trifluoromethyl)phenyl)-5-methoxy-3-(6-(5-(morpholinomethyl)pyridin-2-ylamino)-4,5'-bipyrimidin-4'-ylamino)benzamide, {6-[3-(2,6-Dichloro-3,5-dimethoxy-phenylamino)-pyrazin-2-yl]-pyrimidin-4-yl}-(5-morpholin-4-ylmethyl-pyridin-2-yl)-amine, {6-[3-(2-chloro-3,5-dimethoxy-6-fluoro phenylamino)-pyrazin-2-yl]-pyrimidin-4-yl}-(5-morpholin-4-ylmethyl-pyridin-2-yl)-amine, {6-[3-(2,6-Dichloro-3,5-dimethoxy-phenylamino)-pyrazin-2-yl]-pyrimidin-4-yl}-(4-morpholin-4-ylmethyl-pyridin-2-yl)-amine, {6-[3-(2-chloro-3,5-dimethoxy-6-fluoro phenylamino)-pyrazin-2-yl]-pyrimidin-4-yl}-(4-morpholin-4-ylmethyl-pyridin-2-yl)-amine, {6-[3-(2,6-Dichloro-3,5-dimethoxy-phenylamino)-pyrazin-2-yl]-pyrimidin-4-yl}-(4-[2-(morpholin-4-yl)-ethyl]-pyridin-2-yl)-amine, {6-[3-(2- chloro-3,5-dimethoxy-6-fluoro phenylamino)-pyrazin-2-yl]-pyrimidin-4-yl}-(4-[2-(morpholin-4-yl)-ethyl]-pyridin-2-yl)-amine, {6-[3-(2,6-Dichloro-3,5-dimethoxy-phenylamino)-pyrazin-2-yl]-pyrimidin-4-yl}-(5-[1-(2-hydroxyethyl)-piperazin-4-yl]-pyrimidin-2-yl)-amine, {6-[3-(2,6-Dichloro-3,5-dimethoxy-phenylamino)-pyrazin-2-yl]-pyrimidin-4-yl}-(5-[1-(2-hydroxy-1-oxo-ethyl)-piperazin-4-yl]-pyridin-2-yl)-amine, {6-[3-(2,6-Dichloro-3,5-dimethoxy-phenylamino)-pyrazin-2-yl]-pyrimidin-4-yl}-(5-[1-hydroxyethyl]-pyridin-2-yl)-amine, {6-[3-(2,6-Difluoro-3-methoxy-phenylamino)-pyrazin-2-yl]-pyrimidin-4-yl}-amine, {6-[3-(2,6-Difluoro-3-methoxy-phenylamino)-pyrazin-2-yl]-pyrimidin-4-yl}-N-(5-(morpholin-4-ylmethyl)-pyridin-2-yl)-amine, {6-[3-(2,6-Difluoro-3-methoxy-phenylamino)-pyrazin-2-yl]-pyrimidin-4-yl}-(4-(morpholin-4-ylmethyl)-pyridin-2-yl)-amine, 6-(3-(2,6-dichlorophenylamino)pyrazin-2-yl)pyrimidin-4-amine, 6-(3-(2,6-dichlorophenylamino)pyrazin-2-yl)-N-(5-(morpholinomethyl)pyridin-2-yl)pyrimidin-4-amine, 6-(3-(2,6-dichlorophenylamino)pyrazin-2-yl)-N-(5-(2-morpholinoethyl)pyridin-2-yl)pyrimidin-4-amine, 6-(3-(2,6-dichlorophenylamino)pyrazin-2-yl)-N-(4-(4-ethylpiperazin-1-yl)phenyl)pyrimidin-4-amine, and 6-(3-(2,6-dichlorophenylamino)pyrazin-2-yl)-N-(4-(2-(diethylamino)ethoxy)phenyl)pyrimidin-4-amine.

Further preferred compounds of the invention are detailed in the Examples and in Table I and Table II, infra.

Where a compound of the Formula I or a compound of the invention (and also a precursor thereof) is mentioned generally or specifically, this is intended to include also an N-oxide derivative, an individual isomer, a mixture of isomers; and/or a pharmaceutically acceptable salt thereof, including a solvate, e.g. hydrate, respectively. Where the plural (e.g. compounds, salts, isomers or the like) is used, this is intended also to include the corresponding singular (e.g. one compound, one salt, one isomer or the like). A pure compound of the formula I, or a pharmaceutically acceptable salt thereof, are especially preferred according to all embodiments of the invention Pharmacology and Utility Compounds of the invention modulate the activity of kinases and, as such, are useful for treating diseases or disorders in which kinases, contribute to the pathology and/or symptomology of the disease. Examples of kinases that are inhibited by the compounds and compositions described herein and against which the methods described herein are useful include, but are not limited to, FGFR3, Fms, c-RAF, KDR and Tie2, and further B-Raf, LCK and (especially Bcr-) Abl.

The Ras-Raf-MEK-ERK signaling pathway mediates cellular response to growth signals. Ras is mutated to an oncogenic form in approximately 15% of human cancer. The Raf family belongs to the serine/threonine protein kinase and it includes three members, A-Raf, B-Raf and C-Raf (or Raf-1). The focus on Raf being a drug target has centered on the relationship of Raf as a downstream effector of Ras. However, B-Raf may have a prominent role in the formation of certain tumors with no requirement for an activated Ras allele (Nature 417:949-954 (2002). In particular, B-Raf mutations have been detected in a large percentage of malignant melanomas. Existing medical treatments for melanoma are limited in their effectiveness, especially for late stage melanomas. The compounds of the present invention also inhibit cellular processes involving B-Raf kinase, providing a new therapeutic opportunity for treatment of human cancers, such as melanoma.

Certain abnormal proliferative conditions are believed to be associated with Raf expression and are, therefore, believed to be responsive to inhibition of Raf expression. Abnormally high levels of expression of the Raf protein are also implicated in transformation and abnormal cell proliferation. These abnormal proliferative conditions are also believed to be responsive to inhibition of Raf expression. For example, expression of the c-Raf protein is believed to play a role in abnormal cell proliferation since it has been reported that 60% of all lung carcinoma cell lines express unusually high levels of c-Raf mRNA and protein. Further examples of abnormal proliferative conditions are hyper-proliferative disorders such as cancers, tumors, hyperplasia, pulmonary fibrosis, angiogenesis, psoriasis, atherosclerosis and smooth muscle cell proliferation in the blood vessels, such as stenosis or restenosis following angioplasty. The cellular signaling pathway of which Raf is a part has also been implicated in inflammatory disorders characterized by T-cell proliferation (T-cell activation and growth), such as tissue graft rejection, endotoxin shock, and glomerular nephritis, for example.

The compounds of the present invention may also inhibit cellular processes involving c-Raf kinase. c-Raf is activated by the Ras oncogene, which is mutated in a wide number of human cancers. Therefore inhibition of the kinase activity of c-Raf may provide a way to prevent Ras mediated tumor growth [Campbell, S. L., Oncogene, 17, 1395 (1998)].

Fibroblast growth factor receptor 3 (FGFR3) is a member of the FGF receptor tyrosine kinase family. Activating mutations of FGFR3 are found in 74% of superficial bladder cancer (38-46% of total bladder cancer), 5% cervical cancer and about 10% of multiple myeloma patients with t(4;14)(p16.3; q32.3) chromosomal translocation. The t(4;14) chromosomal translocation, founding about 15% of multiple myeloma patients, results in elevated expression of FGFR3 in plasma cells. When expressed in hematopoietic cells; the active mutant and wild-type FGFR3 are tumorigenic. Therefore, inhibitors of FGFR3, such as compounds of the invention, can provide a new and effective therapeutic treatment for bladder cancer and others such as t(4;14) multiple myeloma.

FGFR3 has also been shown to exert a negative regulatory effect on bone growth and an inhibition of chondrocyte proliferation. Thanatophoric dysplasia is caused by different mutations in fibroblast growth factor receptor 3, and one mutation, TDII FGFR3, has a constitutive tyrosine kinase activity which activates the transcription factor Stat1, leading to expression of a cell-cycle inhibitor, growth arrest and abnormal bone development (Su et al., Nature, 1997, 386, 288-292). FGFR3 is also often expressed in multiple myeloma-type cancers. Inhibitors of FGFR3 activity are useful in the treatment of T-cell mediated inflammatory or autoimmune diseases including but not limited to rheumatoid arthritis (RA), collagen II arthritis, multiple sclerosis (MS), systemic lupus erythematosus (SLE), psoriasis, juvenile onset diabetes, Sjogren's disease; thyroid disease, sarcoidosis, autoimmune uveitis, inflammatory bowel disease (Crohn's and ulcerative colitis), celiac disease and myasthenia gravis.

Abelson tyrosine kinase (i.e. Abl, c-Abl) is involved in the regulation of the cell cycle, in the cellular response to genotoxic stress, and in the transmission of information about the cellular environment through integrin signaling. The Abl protein appears to serve a complex role as a cellular module that integrates signals from various extracellular and intracellular sources and that influences decisions in regard to cell cycle and apoptosis. Abelson tyrosine kinase includes sub-types derivatives such as the chimeric fusion (oncoprotein) Bcr-Abl with deregulated tyrosine kinase activity or the v-Abl. Bcr- Abl is important in the pathogenesis of 95% of chronic myelogenous leukemia (CML) and 10% of acute lymphocytic leukemia.

Compounds of the present invention may inhibit Abl kinase, for example, v-Abl kinase. The compounds of the present invention may also inhibit wild-type Bcr-Abl kinase and mutations of Bcr-Abl kinase, and thus may be suitable for the treatment of Bcr-Abl-positive cancer and tumor diseases, such as leukemias (e.g., chronic myeloid leukemia and acute lymphoblastic leukemia) and other proliferation disorders related to Bcr-Abl. Compounds of the present invention may also be effective against leukemic stem cells, and may be potentially useful for the purification of these cells in vitro after removal of said cells (for example, bone marrow removal), and reimplantation of the cells once they have been cleared of cancer cells (for example, reimplantation of purified bone marrow cells).

The Src family of kinases is implicated in cancer, immune system dysfunction and bone remodeling diseases. Members of the Src family include the following eight kinases in mammals: Src, Fyn, Yes, Fgr, Lyn, Hck, Lck, and Blk. For general reviews, see Thomas and Brugge, Annu. Rev. Cell Dev. Biol. (1997) 13, 513; Lawrence and Niu, Pharmacol. Ther. (1998) 77, 81; Tatosyan and Mizenina, Biochemistry (Moscow) (2000) 65, 49; Boschelli et al., Drugs of the Future 2000, 25(7), 717.

Lck plays a role in T-cell signaling. Mice that lack the Lck gene have a poor ability to develop thymocytes. The function of Lck as a positive activator of T-cell signaling suggests that Lck inhibitors may be useful for treating autoimmune disease such as rheumatoid arthritis. Molina et al., Nature, 357, 161 (1992). Hck, Fgr and Lyn have been identified as important mediators of integrin signaling in myeloid leukocytes. Lowell et al., J. Leukoc. Diol., 65, 313 (1999). Inhibition of these kinase mediators may therefore be useful for treating inflammation. Boschelli et al., Drugs of the Future 2000, 25(7), 717.

Lyn, a member of the Src family, plays a role in the regulation of B-cell immune responses. Lyn-deficient mice display disrupted B-cell function, leading to autoimmunity and defective mast cell degranulation. Studies have also suggested that Lyn is a negative regulator of apoptosis in various cell systems. In leukemic cells, Lyn is constitutively activated, and the inhibition of Lyn expression reversed proliferation. In addition, Lyn has been shown to be expressed in colon and PC cells, and that overexpression of a dominant active Lyn in colon cancer cell lines induced chemoresistance. (Goldenberg-Furmanov et al., Cancer Res. 64:1058-1066 (2004)).

The kinase, c-Src transmits oncogenic signals of many receptors. For example, over-expression of EGFR or HER2/neu in tumors leads to the constitutive activation of c-Src, which is characteristic for the malignant cell but absent from the normal cell. On the other hand, mice deficient in the expression of c-Src exhibit an osteopetrotic phenotype, indicating a key participation of c-Src in osteoclast function and a possible involvement in related disorders. c-Src tyrosine kinase (CSK) influences the metastatic potential of cancer cells, particularly colon cancer.

c-Kit has a substantial homology to the PDGF receptor and to the CSF-1 receptor (c-Fms). Investigations on various erythroid and myeloid cell lines indicate an expression of the c-Kit gene in early stages of differentiation (Andre et al., Oncogene 4 (1989), 1047-1049). Certain tumors such as glioblastoma cells likewise exhibit a pronounced expression of the c-Kit gene.

Kinase insert domain-containing receptor (referred to as "KDR" hereinafter) [WO 92/14748; Proc. Natl. Acad. Sci. USA, 88: 9026 (1991)]; Biochem. Biophys. Res. Comm., 187: 1579 (1992); WO 94/11499) and Fms-like tyrosine kinase (referred to as "Flt1" hereinafter) [Oncogene, 5: 519 (1990); Science, 255: 989 (1992)] belong to the receptor type tyrosine kinase family. It has been reported that VEGF specifically binds to Flt-1 and KDR at Kd values of 20 pM and 75 pM and that Flt1 and KDR are expressed in vascular endothelial cells in a specific manner [Proc. Natl. Acad. Sci. USA, 90: 7533 (1993); Proc. Natl. Acad. Sci. USA, 90: 8915 (1993)]. With regard to Flt-1 in various diseases, it has been reported that, in comparison with vascular endothelial cells in normal tissues, expression of Flt-1 mRNA increases in tumor vascular endothelial cells, of human glioblastoma tissues [Nature, 359: 845 (1992)] and tumor vascular endothelial cells of human digestive organ cancer tissues [Cancer Research, 53: 4727 (1993)]. Additionally, it has been reported that expression of Flt-1 mRNA is observed by in situ hybridization in vascular endothelial cells of joints of patients with rheumatoid arthritis [J. Experimental Medicine, 180: 341 (1994)]. Studies also suggest that Flt-1 plays an important role in tumor angiogenesis.

Flt3 is a member of the type III receptor tyrosine kinase (RTK) family. Flt3 (Fms-like tyrosine kinase) is also known as Flk-2 (fetal liver kinase 2). Aberrant expression of the Flt3 gene has been documented in both adult and childhood leukemias including acute myeloid leukemia (AML), AML with trilineage myelodysplasia (AML/TMDS), acute lymphoblastic leukemia (ALL), and myelodysplastic syndrome (MDS). In approximately 25% of AML, the leukemia cells express a constitutively active form of auto-phosphorylated (p) FLT3 tyrosine kinase on the cell surface. The activity of p-FLT3 confers growth and survival advantage on the leukemic cells. Inhibition of p-FLT3 kinase activity induces apoptosis (programmed cell death) of the leukemic cells.

Breast tumor kinase (Brk) is a soluble protein-tyrosine kinase overexpressed in the majority of breast cancers and also in normal skin and gut epithelium, but not in normal breast epithelial cells. (Zhang et al., J. Biol. Chem. 280:1982-1991 (2005)).

The Janus kinases (JAK) are a family of tyrosine kinases consisting of JAK1, JAK2, JAK3 and TYK2. The JAKs play an important role in cytokine signaling. The down-stream substrates of the JAK family of kinases include the signal transducer and activator of transcription (STAT) proteins. JAK/STAT signaling has been implicated in the mediation of many abnormal immune responses such as allergies, asthma, autoimmune diseases such as transplant rejection, rheumatoid arthritis, amyotrophic lateral sclerosis and multiple sclerosis, as well as in solid and hematologic malignancies such as leukemias and lymphomas.

An important factor in the tumor angiogenesis is vascular endothelium growth factor (VEGF). VEGF can promote and maintain the establishment of tumor vascular system, and can also promote the tumor growth directly. VEGF can induce the mitogenesis and chemotaxis of vascular endothelial cell (VEC) and tumor cell (TC). Almost all types of TC and tumor VEC can secret VEGF, but the expression of VEGF in the normal tissue is very low. In the four VEGF receptors, KDR is the main receptor which gives play to VEGF functions. KDR is highly expressed on the TC and tumor VEC while lowly expressed on the normal tissues. (Ren et al., World J. Gastroentrol. 8:596-601 (2002)).

Mitogen-activated protein kinases (MAPKs) are members of conserved signal transduction pathways that activate transcription factors, translation factors and other target molecules in response to a variety of extracellular signals. MAPKs are activated by phosphorylation at a dual phosphorylation motif having the sequence Thr-X-Tyr by mitogen-activated protein kinase kinases (MKKs). In higher eukaryotes, the physiological role of MAPK signaling has been correlated with cellular events such as proliferation, oncogenesis, development and differentiation. Accordingly, the ability to regulate signal transduction via these pathways (particularly via MKK4 and MKK6) could lead to the development of treatments and preventive therapies for human diseases associated with MAPK signaling, such as inflammatory diseases, autoimmune diseases and cancer.

Multiple forms of p38 MAPK (α, β, γ, δ), each encoded by a separate gene, form part of a kinase cascade involved in the response of cells to a variety of stimuli, including osmotic stress, UV light and cytokine mediated events. These four isoforms of p38 are thought to regulate different aspects of intracellular signaling. Its activation is part of a cascade of signaling events that lead to the synthesis and production of pro-inflammatory cytokines like TNFα. P38 functions by phosphorylating downstream substrates that include other kinases and transcription factors. Agents that inhibit p38 kinase have been shown to block the production of cytokines, including but not limited to TNFα, IL-6, IL-8 and IL-1β. Peripheral blood monocytes (PBMCs) have been shown to express and secrete pro-inflammatory cytokines when stimulated with lipopolysaccharide (LPS) in vitro. P38 inhibitors efficiently block this effect when PBMCs are pretreated with such compounds prior to stimulation with LPS. P38 inhibitors are efficacious in animal models of inflammatory disease. The destructive effects of many disease states are caused by the over production of pro-inflammatory cytokines. The ability of p38 inhibitors to regulate this overproduction makes them useful as disease modifying agents.

Molecules that block p38's function have been shown to be effective in inhibiting bone resorption, inflammation, and other immune and inflammation-based pathologies. Thus, a safe and effective p38 inhibitor would provide a means to treat debilitating diseases that can be regulated by modulation of p38 signaling like. Therefore, compounds of the invention that inhibit p38 activity are useful for the treatment of inflammation, osteoarthritis, rheumatoid arthritis, cancer, autoimmune diseases, and for the treatment of other cytokine mediated diseases.

PDGF (Platelet-derived Growth Factor) is a commonly occurring growth factor, which plays an important role both in normal growth and also in pathological cell proliferation, such as is seen in carcinogenesis and in diseases of the smooth-muscle cells of blood vessels, for example in atherosclerosis and thrombosis. Compounds of the invention may inhibit PDGF receptor (PDGFR) activity, and may therefore be suitable for the treatment of tumor diseases, such as gliomas, sarcomas, prostate tumors, and tumors of the colon, breast, and ovary.

Compounds of the present invention, may be used not only as a tumor-inhibiting substance, for example in small cell lung cancer, but also as an agent to treat non-malignant proliferative disorders; such as atherosclerosis, thrombosis, psoriasis, scleroderma and fibrosis. Compounds of the present invention may also be useful for the protection of stem cells, for example to combat the hemotoxic effect of chemotherapeutic agents, such as 5-fluoruracil, and in asthma. Compounds of the invention may especially be used for the treatment of diseases, which respond to an inhibition of the PDGF receptor kinase.

Compounds of the present invention may exhibit useful effects in the treatment of disorders arising as a result of transplantation, for example, allogenic transplantation, especially tissue rejection, such as obliterative bronchiolitis (OB), i.e. a chronic rejection of allogenic lung transplants. In contrast to patients without OB, those with OB often show an elevated PDGF concentration in bronchoalveolar lavage fluids.

Compounds of the present invention may also be effective against diseases associated with vascular smooth-muscle cell migration and proliferation (where PDGF and PDGFR often also play a role), such as restenosis and atherosclerosis. These effects and the consequences thereof for the proliferation or migration of vascular smooth-muscle cells in vitro and in vivo may be demonstrated by administration of the compounds of the present invention, and also by investigating its effect on the thickening of the vascular intima following mechanical injury in vivo.

Protein kinase C (PKC) functions in processes relevant to carcinogenesis, tumor cell metastasis, and apoptosis. PKCα is associated with a diverse range of cancers, and is previously shown to be overexpressed in three out of four antiestrogen resistant breast cancer cell lines. (Frankel et al., Breast Cancer Res Treat. 2006 Oct. 24 (ePub)).

The stress activated protein kinases (SAPKs) are a family of protein kinases that represent the penultimate step in signal transduction pathways that result in activation of the c-Jun transcription factor and expression of genes regulated by c-Jun. In particular, c-Jun is involved in the transcription of genes that encode proteins involved in the repair of DNA that is damaged due to genotoxic insults. Therefore, agents that inhibit SAPK activity in a cell prevent DNA repair and sensitize the cell to agents that induce DNA damage or inhibit DNA synthesis and induce apoptosis of a cell or that inhibit cell proliferation.

The region encompassing the SNF1LK locus (also known as SIK) has been implicated in congenital heart defects often observed in patients with Down syndrome. Snf1lk is also expressed in skeletal muscle progenitor cells of the somite beginning at 9.5 dpc, suggesting a more general role for snf1lk in the earliest stages of muscle growth and/or differentiation. (Genomics 83:1105-15 (2004)).

Syk is a tyrosine kinase that plays an important role in mast cell degranulation and eosinophil activation. Accordingly, Syk kinase is implicated in various allergic disorders, in particular asthma. It has been shown that Syk binds to the phosphorylated gamma chain of the FcεR1 receptor via N-terminal $SH_2$ domains, and is important for downstream signaling.

An inhibition of tumor growth and vascularization, and a decrease in lung metastases during adenoviral infections or during injections of the extracellular domain of Tie-2 (Tek) have been shown in breast tumor and melanoma xenograft models. Lin et al., J. Clin. Invest. 100, 8: 2072-2078 (1997) and P. Lin, PNAS 95, 8829-8834, (1998). Tie2 inhibitors can be used in situations where neovascularization takes place inappropriately (i.e. in diabetic retinopathy, chronic inflammation, psoriasis, Kaposi's sarcoma, chronic neovascularization due to macular degeneration, rheumatoid arthritis, infantile haemangioma and cancers).

The class III receptor tyrosine kinases (RTKs), which include c-FMS, c-KIT, FLT3, platelet-derived growth factor receptor α(PDGFRα) and β(PDGFRβ), have been reported to be associated with the pathogenesis of an increasing number of malignancies. (Blume-Jensen et al., Nature 411:355-565 (2001); Scheijin et al., Oncogene 21:3314-3333 (2002)).

In accordance with the foregoing, the present invention further provides a method for preventing or treating any of the diseases or disorders described above in a subject in need of such treatment, which method comprises administering to said subject a therapeutically effective amount (See, "*Administration and Pharmaceutical Compositions*", infra) of a compound of Formula I or a pharmaceutically acceptable salt thereof. For any of the above uses, the required dosage will vary depending on the mode of administration, the particular condition to be treated and the effect desired.

Administration and Pharmaceutical Compositions

In general, compounds of the invention will be administered in therapeutically effective amounts via any of the usual and acceptable modes known in the art, either singly or in combination with one or more therapeutic agents. A therapeutically effective amount may vary widely depending on the severity of the disease, the age and relative health of the subject, the potency of the compound used and other factors. In general, satisfactory results are indicated to be obtained systemically at daily dosages of from about 0.03 to 2.5 mg/kg per body weight. An indicated daily dosage in the larger mammal, e.g. humans, is in the range from about 0.5 mg to about 100 mg, conveniently administered, e.g. in divided doses up to four times a day or in retard form. Suitable unit dosage forms for oral administration comprise from ca. 1 to 50 mg active ingredient.

Compounds of the invention can be administered as pharmaceutical compositions by any conventional route, in particular enterally, e.g., orally, e.g., in the form of tablets or capsules, or parenterally, e.g., in the form of injectable solutions or suspensions, topically, e.g., in the form of lotions, gels, ointments or creams, or in a nasal or suppository form. Pharmaceutical compositions comprising a compound of the present invention in free form or in a pharmaceutically acceptable salt form in association with at least one pharmaceutically acceptable carrier or diluent can be manufactured in a conventional manner by mixing, granulating or coating methods. For example, oral compositions can be tablets or gelatin capsules comprising the active ingredient together with a) diluents, e.g., lactose, dextrose, sucrose, mannitol, sorbitol, cellulose and/or glycine; b) lubricants, e.g., silica, talcum, stearic acid, its magnesium or calcium salt and/or polyethyleneglycol; for tablets also c) binders, e.g., magnesium aluminum silicate, starch paste, gelatin, tragacanth, methylcellulose, sodium carboxymethylcellulose and or polyvinylpyrrolidone; if desired d) disintegrants, e.g., starches, agar, alginic acid or its sodium salt, or effervescent mixtures; and/or e) absorbents, colorants, flavors and sweeteners. Injectable compositions can be aqueous isotonic solutions or suspensions, and suppositories can be prepared from fatty emulsions or suspensions. The compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. Suitable formulations for transdermal applications include an effective amount of a compound of the present invention with a carrier. A carrier can include absorbable pharmacologically acceptable solvents to assist passage through the skin of the host. For example, transdermal devices are in the form of a bandage comprising a backing member, a reservoir containing the compound optionally with carriers, optionally a rate controlling barrier to deliver the compound to the skin of the host at a controlled and predetermined rate over a prolonged period of time, and means to secure the device to the skin. Matrix transdermal formulations may also be used. Suitable formulations for topical application, e.g., to the skin and eyes, are preferably aqueous solutions, ointments, creams or gels well-known in the art. Such may contain solubilizers, stabilizers, tonicity enhancing agents, buffers and preservatives.

Compounds of the invention can be administered in therapeutically effective amounts in combination with one or more therapeutic agents (pharmaceutical combinations). For example, synergistic effects can occur with other immunomodulatory or anti-inflammatory substances, for example when used in combination with cyclosporin, rapamycin, or ascomycin, or immunosuppressant analogues thereof, for example cyclosporin A (CsA), cyclosporin G, FK-506, rapamycin, or comparable compounds, corticosteroids, cyclophosphamide, azathioprine, methotrexate, brequinar, leflunomide, mizoribine, mycophenolic acid, mycophenolate mofetil, 15-deoxyspergualin, immunosuppressant antibodies, especially monoclonal antibodies for leukocyte receptors, for example MHC, CD2, CD3, CD4, CD7, CD25, CD28, B7, CD45, CD58 or their ligands, or other immunomodulatory compounds, such as CTLA4Ig. Where the compounds of the invention are administered in conjunction with other therapies, dosages of the co-administered compounds will of course vary depending on the type of co-drug employed, on the specific drug employed, on the condition being treated and so forth.

The invention also provides for a pharmaceutical combinations, e.g. a kit, comprising a) a first agent which is a compound of the invention as disclosed herein, in free form or in pharmaceutically acceptable salt form, and b) at least one co-agent. The kit can comprise instructions for its administration.

The terms "co-administration" or "combined administration" or the like as utilized herein are meant to encompass administration of the selected therapeutic agents to a single patient, and are intended to include treatment regimens in which the agents are not necessarily administered by the same route of administration or at the same time.

The term "pharmaceutical combination" as used herein means a product that results from the mixing or combining of more than one active ingredient and includes both fixed and non-fixed combinations of the active ingredients. The term "fixed combination" means that the active ingredients, e.g. a compound of Formula I and a co-agent, are both administered to a patient simultaneously in the form of a single entity or dosage. The term "non-fixed combination" means that the active ingredients, e.g. a compound of Formula I and a co-agent, are both administered to a patient as separate entities either simultaneously, concurrently or sequentially with no specific time limits, wherein such administration provides therapeutically effective levels of the 2 compounds in the body of the patient. The latter also applies to cocktail therapy, e.g. the administration of 3 or more active ingredients.

Processes for Making Compounds of the Invention

The present invention also includes processes for the preparation of compounds of the invention. In the reactions described, it can be necessary to protect reactive functional groups, for example hydroxy, amino, imino, thio or carboxy groups, where these are desired in the final product, to avoid their unwanted participation in the reactions. Conventional protecting groups can be used, and their introduction and their removal can be effected, in accordance with standard practice, for example, see T. W. Greene and P. G. M. Wuts in "Protective Groups in Organic Chemistry", John Wiley and Sons, 1991.

Compounds of Formula I wherein Y is CH and Z is N can be prepared by proceeding as in the following Reaction Scheme I:

Reaction Scheme I
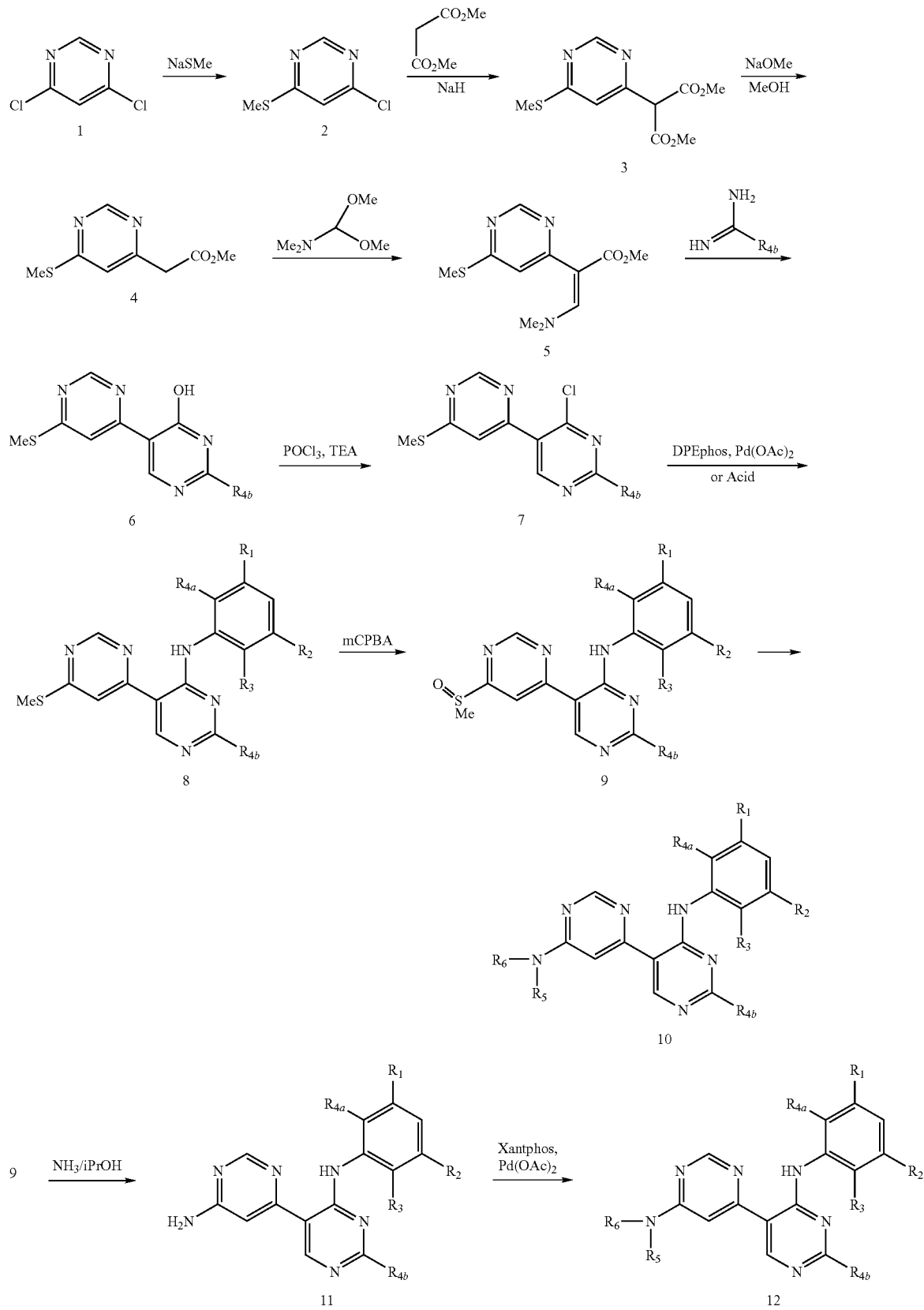

-continued

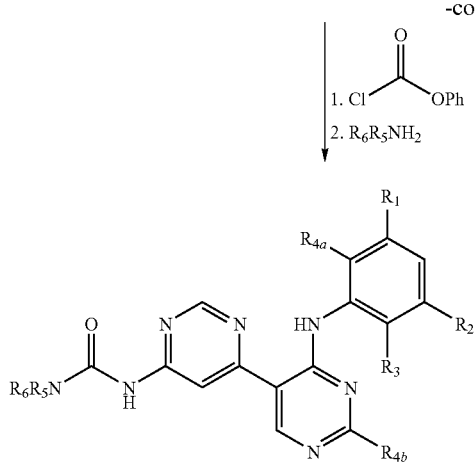

in which $R_1$, $R_2$, $R_3$, $R_{4a}$, $R_{4b}$, $R_5$ and $R_6$ are as defined in the Summary of the Invention or in the preferred embodiments.

A compound of Formula 2 can be prepared by reacting of a compound of formula 1 with NaSMe in the presence of a suitable solvent (e.g., THF). A compound of formula 3 can be prepared by reacting of a compound of formula 2 and dimethyl malonate in the presence of a solvent (e.g., DMSO, DMF and the like) using an appropriate base (e.g., sodium hydride (NaH)).

A compound of formula 4 can be prepared by decarboxylation of a compound of formula 3 with catalytic amount of base (e.g., NaOMe) in a suitable solvent (e.g., MeOH) and can take up to 4 hours to complete. Compounds of formula 4 can be converted to give compounds of formula 5 with a suitable eneamine formation reagent (e.g., N,N-dimethylformamide dimethyl acetal) and can take up to 24 hours to complete. The reaction of the resulting eneamine 5 with an appropriate amidine affords a compound of formula 6. Compounds of formula 7 can be prepared by reacting compounds of formula 6 with a suitable chloronation reagent (e.g., $POCl_3$ or the like) in the presence of base (e.g., triethyl amine). The reaction can be effected in an appropriate solvent (e.g., $CH_3CN$) and requires up to 24 hours to complete. Compounds of formula 8 can be prepared by reacting a compound of formula 7 with an appropriate aniline (e.g., 2,6-dichloro-3,5-dimethoxyaniline) by two methods. For the steric and less reactive aniline, the reaction proceeds in the presence of a suitable catalyst (e.g., Pd (II) salt, or the like), a suitable ligand (e.g., DPEphos, or the like) and a suitable solvent (e.g., 1,4-dioxane, or the like), in a temperature range of about 80 to about 150° C. and can take up to about 20 hours to complete. For condensations of formula 7 with more reactive or less hindered anilines, these are carried out with or without acid (e.g., TsOH, HOAc, HCl, or the like) in a suitable solvent (e.g., alcohol, DMSO, DMF, or the like). Compounds of formula 8 can be further oxidized to give compounds of formula 9 with a suitable oxidizing agent (e.g., m-chloroperoxybenzoic acid (mCPBA), or the like) and can take up to 6 hours to complete. Compounds of formula 10 can be prepared by reacting a compound of formula 9 with an appropriate amine or aniline. The reaction is carried out in a temperature range of 100-150° C. and can take up to 10 hours to complete. The reaction conditions for alkyl amine displacement involves heating a compound of formula 9 with 5-10 equivalents of amine in a suitable solvent (e.g. DMSO, DMF, or the like).

Compounds of formula 11 can be prepared by amination of compounds of formula 9 with $NH_3$ in an appropriate solvent (e.g., isopropanol or the like) in a temperature range of 100-150° C. and can take up to 20 hours to complete. Compounds of formula 12 can be prepared by reacting a compound of formula 11 with an appropriate bromide (e.g., 4-(6-bromopyridi-3-ylmethyl)-morpholine). The reaction proceeds in the presence of a suitable catalyst (e.g., Pd (II) salt, or the like), a suitable ligand (e.g., DPEphos, Xantphos or the like) and a suitable solvent (e.g., 1,4-dioxane, or the like), in a temperature range of about 80 to about 150° C. and can take up to about 20 hours to complete.

A compound of Formula 13 can be synthesized by reacting a compound of formula 11 in the presence of a suitable solvent (for example, THF, and the like), a suitable reactive chemical intermediate (for example, phenyl chloroformate, and the like) and a suitable base (for example, pyridine, and the like). The reaction proceeds in a temperature range of about 0° C. to about 40° C. and can take up to about 2 hours to complete. The resulting carbamate is further reacted with an appropriate amine (for example, 4-(2-aminoethyl)morpholine), proceeding at a temperature range of about 0° C. to about 40° C. and can take up to about 24 hours to complete.

Compounds of Formula I wherein Z is CH and Y is N can be prepared by proceeding as in the following Reaction Scheme II:

Scheme II:

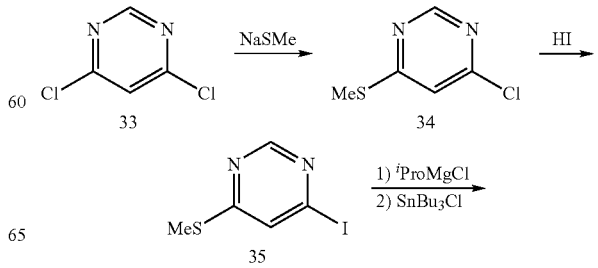

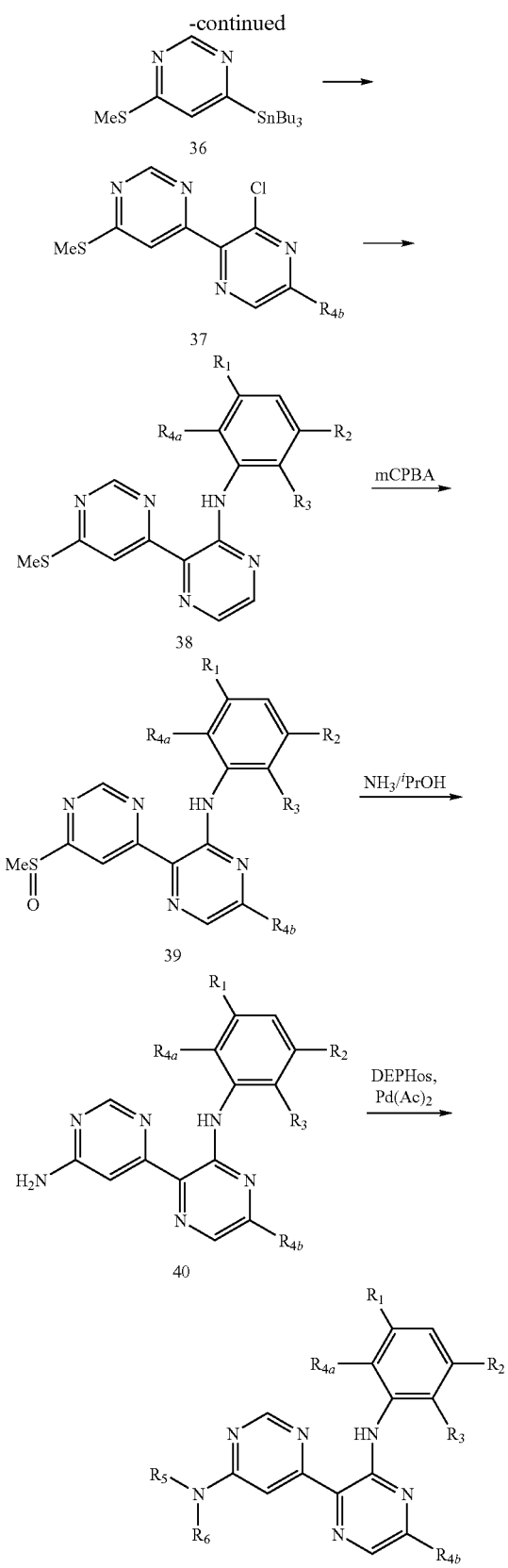

in which $R_1$, $R_2$, $R_3$, $R_{4a}$, $R_{4b}$ and $R_6$ are as defined in the Summary of the invention or for the preferred embodiments of compounds of the formula I.

The reaction of compound 33 to compound 34 can be prepared as described for compounds 1 and 2 in Scheme I. A compound of the formula 35 can be prepared in the presence of hydroidic acid (or an appropriate precursor) in an appropriate solvent, such as a halogenated hydrocarbon, e.g. dichloromethane, at appropriate temperatures, e.g. from 0 to 40° C. The compound of the formula 35 can then e converted to compound 36 in the presence of a Grignard reagent, such as an isopropyl-MgCl complex, followed by a reagent appropriate for the introduction of a trialkylated Sn-substituent, e.g. a trialkylated stannium halogenide, such as $SnBu_3Cl$, e.g. in an appropriate solvent, such as THF, with the reactions preferably taking place at lower temperatures, e.g. from −90 to 0° C. The compound of the formula 36 can then be converted to a compound of the formula 37 under conditions of Stille coupling with an appropriate catalyst, e.g. with triphenylphosphine in the presence of palladium(II) acetate, in an appropriate solvent, e.g. an ether, such as dioxane, e.g. at elevated temperatures in the range from 50 to 140° C. The compound of the formula 38 can e obtained by coupling a compound of the formula 37, with an aniline carrying the substituents $R_1$, $R_2$, $R_3$ and $R_{4b}$ at the positions derivable from formula I under conditions analogous to those mentioned above for the conversion of compound 7 to compound 8. A compound of the formula 39 can be obtained from a compound of the formula 38 by oxidation analogous to that described above for oxidation of compound 8. A compound of the formula 39 can be converted by reaction with a complementary amine or aniline $R_5R_6NH$ directly to a compound of the formula 41, e.g. as described above for conversion of compound 9 to 10, or first with ammonia in an appropriate solvent, e.g. an alcohol, such as propanol, to an amino compound of the formula 40, e.g. under conditions as described above for conversion of compound 11 to 12, or by acylation as described above for the conversion of compound 11 to 13.

Compounds of the formula I can, if not described otherwise, also be obtained in analogy to methods described in the Examples, as well as starting materials. The starting materials are commercially available, can be obtained according to methods known in the art and/or can be obtained by or in analogy to methods described in the examples.

Detailed examples of the synthesis of a compound of Formula I can be found in the Examples, infra.

Additional Processes for Making Compounds of the Invention

A compound of the invention can be prepared as a pharmaceutically acceptable acid addition salt by reacting the free base form of the compound with a pharmaceutically acceptable inorganic or organic acid. Alternatively, a pharmaceutically acceptable base addition salt of a compound of the invention can be prepared by reacting the free acid form of the compound with a pharmaceutically acceptable inorganic or organic base.

Alternatively, the salt forms of the compounds of the invention can be prepared using salts of the starting materials or intermediates.

The free acid or free base forms of the compounds of the invention can be prepared from the corresponding base addition salt or acid addition salt from, respectively. For example a compound of the invention in an acid addition salt form can be converted to the corresponding free base by treating with a suitable base (e.g., ammonium hydroxide solution, sodium hydroxide, and the like). A compound of the invention in a base addition salt form can be converted to the corresponding free acid by treating with a suitable acid (e.g., hydrochloric acid, etc.).

Compounds of the invention in unoxidized form can be prepared from N-oxides of compounds of the invention by treating with a reducing agent (e.g., sulfur, sulfur dioxide, triphenyl phosphine, lithium borohydride, sodium borohydride, phosphorus trichloride, tribromide, or the like) in a suitable inert organic solvent (e.g. acetonitrile, ethanol, aqueous dioxane, or the like) at 0 to 80° C.

Prodrug derivatives of the compounds of the invention can be prepared by methods known to those of ordinary skill in the art (e.g., for further details see Saulnier et al., (1994), Bioorganic and Medicinal Chemistry Letters, Vol. 4, p. 1985). For example, appropriate prodrugs, can be prepared by reacting a non-derivatized compound of the invention with a suitable carbamylating agent (e.g., 1,1-acyloxyalkylcarbanochloridate, para-nitrophenyl carbonate, or the like).

Protected derivatives of the compounds of the invention can be made by means known to those of ordinary skill in the art. A detailed description of techniques applicable to the creation of protecting groups and their removal can be found in T. W. Greene, "Protecting Groups in Organic Chemistry", 3$^{rd}$ edition, John Wiley and Sons, Inc., 1999.

Compounds of the present invention can be conveniently prepared, or formed during the process of the invention, as solvates (e.g., hydrates). Hydrates of compounds of the present invention can be conveniently prepared by recrystallization from an aqueous/organic solvent mixture, using organic solvents such as dioxin, tetrahydrofuran or methanol.

Compounds of the invention can be prepared as their individual stereoisomers by reacting a racemic mixture of the compound with an optically active resolving agent to form a pair of diastereoisomeric compounds, separating the diastereomers and recovering the optically pure enantiomers. While resolution of enantiomers can be carried out using covalent diastereomeric derivatives of the compounds of the invention, dissociable complexes are preferred (e.g., crystalline diastereomeric salts). Diastereomers have distinct physical properties (e.g., melting points, boiling points, solubilities, reactivity, etc.) and can be readily separated by taking advantage of these dissimilarities. The diastereomers can be separated by chromatography, or preferably, by separation/resolution techniques based upon differences in solubility. The optically pure enantiomer is then recovered, along with the resolving agent, by any practical means that would not result in racemization. A more detailed description of the techniques applicable to the resolution of stereoisomers of compounds from their racemic mixture can be found in Jean Jacques, Andre Collet, Samuel H. Wilen, "Enantiomers, Racemates and Resolutions", John Wiley And Sons, Inc., 1981.

In summary, the compounds of Formula I can be made by a process, which involves:

(a) that of reaction scheme I; and (b) optionally converting a compound of the invention into a pharmaceutically acceptable salt;

(c) optionally converting a salt form of a compound of the invention to a non-salt form;

(d) optionally converting an unoxidized form of a compound of the invention into a pharmaceutically acceptable N-oxide;

(e) optionally converting an N-oxide form of a compound of the invention to its unoxidized form;

(f) optionally resolving an individual isomer of a compound of the invention from a mixture of isomers;

(g) optionally converting a non-derivatized compound of the invention into a pharmaceutically acceptable prodrug derivative; and (h) optionally converting a prodrug derivative of a compound of the invention to its non-derivatized form.

Insofar as the production of the starting materials is not particularly described, the compounds are known or can be prepared analogously to methods known in the art or as disclosed in the Examples hereinafter.

One of skill in the art will appreciate that the above transformations are only representative of methods for preparation of the compounds of the present invention, and that other well known methods can similarly be used.

EXAMPLES

The present invention is further exemplified, but not limited, by the following examples that illustrate the preparation of compounds of Formula I according to the invention.

In the examples, as well as in the remaining Specification, the following abbreviations are used:

| | |
|---|---|
| Bu | butyl |
| DCM | dichloromethane |
| DMF | N,N-dimethylformamide |
| DMSO | dimethylsulfoxide |
| DPEPhos | |
| Et | ethyl |
| mCPBA | meta-chloroperbenzoic acid |
| Me | methyl |
| Ph | phenyl |
| Pr | propyl |
| $^i$Pr | isopropyl |
| iPrOH | isopropanol |
| TEA | triethylamine |
| THF | tetrahydrofurane |
| Xanthphos | |

Example 1

Synthesis of N4'-(2,6-Dichloro-3,5-dimethoxy-phenyl)-N6-(5-morpholin-4-ylmethyl-pyridin-2-yl)-[4,5']bipyrimidinyl-6,4'-diamine

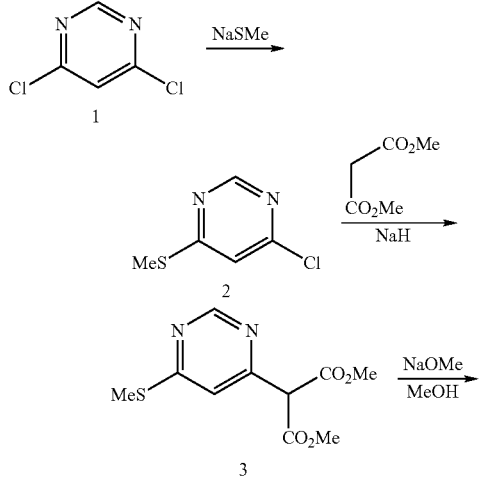

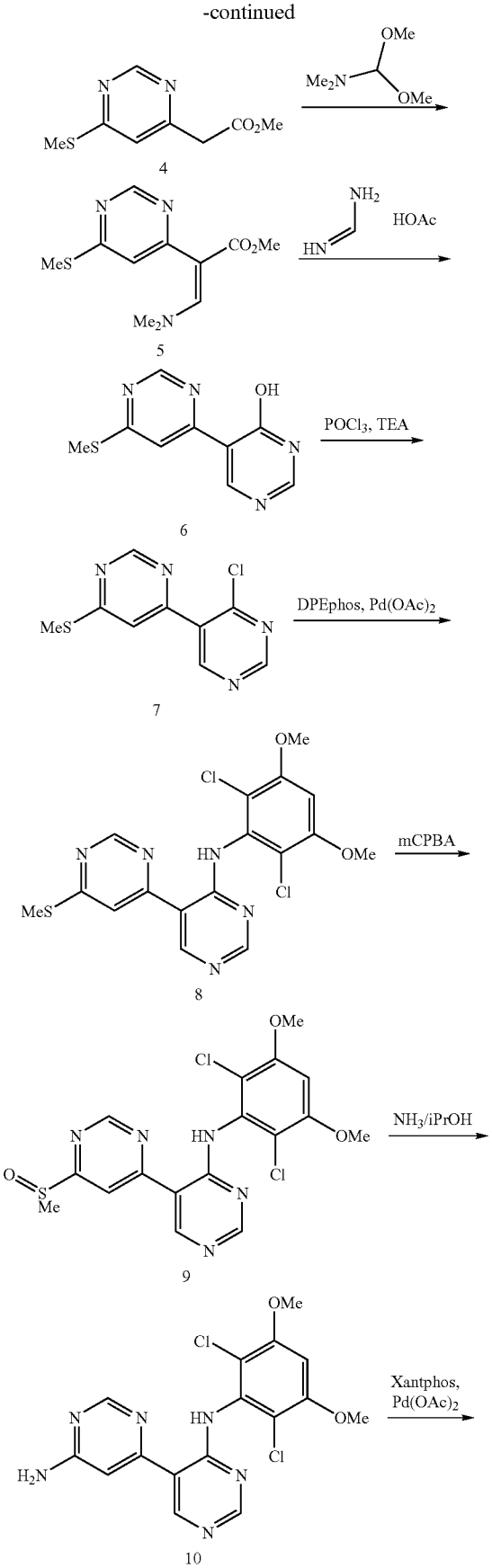

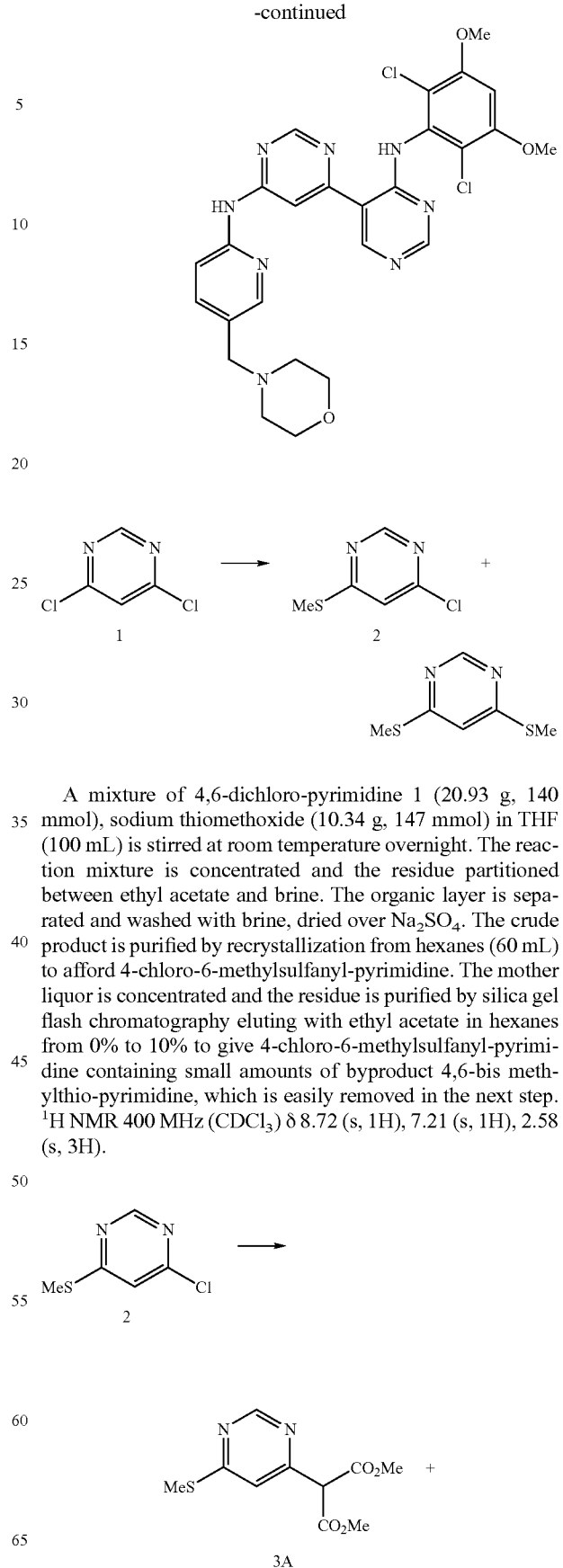

A mixture of 4,6-dichloro-pyrimidine 1 (20.93 g, 140 mmol), sodium thiomethoxide (10.34 g, 147 mmol) in THF (100 mL) is stirred at room temperature overnight. The reaction mixture is concentrated and the residue partitioned between ethyl acetate and brine. The organic layer is separated and washed with brine, dried over $Na_2SO_4$. The crude product is purified by recrystallization from hexanes (60 mL) to afford 4-chloro-6-methylsulfanyl-pyrimidine. The mother liquor is concentrated and the residue is purified by silica gel flash chromatography eluting with ethyl acetate in hexanes from 0% to 10% to give 4-chloro-6-methylsulfanyl-pyrimidine containing small amounts of byproduct 4,6-bis methylthio-pyrimidine, which is easily removed in the next step. $^1$H NMR 400 MHz ($CDCl_3$) δ 8.72 (s, 1H), 7.21 (s, 1H), 2.58 (s, 3H).

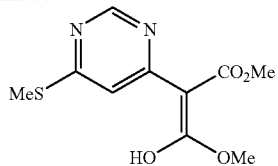

3B (structure was tentatively assigned)

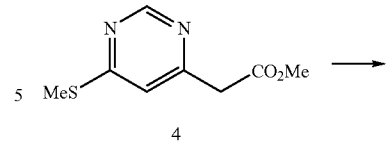

To a suspension of NaH (1.98 g, 50 mmol, 60% in oil) in DMSO (20 mL) is added dimethyl malonate (5.67 mL, 50 mmol) at 23° C. (cooled by ice-water if necessary). After the evolution of hydrogen has ceased, 4-chloro-6-methylsulfanyl-pyrimidine 2 (3.22 g, 20 mmol) is added. The reaction is further heated at 80° C. for 5 hours. The reaction mixture is then cooled to room temperature, and quenched with saturated NH$_4$Cl solution (50 mL). The organics are extracted with ethyl acetate (3×60 mL). The combined organic layers are washed with brine (2×) and dried over Na$_2$SO$_4$, filtered and concentrated. 50 mL of hexanes are added to the residue and heated at 60° C. for half hour and then cooled to room temperature. The solid is filtered and washed with hexanes to afford 2-(6-methylsulfanyl-pyrimidin-4-yl)-malonic acid dimethyl ester. (If necessary, the hexanes washing can be concentrated and purified by silica gel flash chromatography eluting with ethyl acetate in hexanes from 0% to 40% to afford additional product). $^1$H NMR 400 MHz (DMSO-d$_6$) Compound A δ 8.92 (s, 1H), 7.53 (s, 1H), 5.20 (s, 1H) 3.70 (s, 6H), 2.56 (s, 3H); Compound B (tautomer of A, the structure is tentatively assigned) 8.37 (s, 1H), 7.34 (s, 1H), 3.66 (s, 6H), 2.48 (s, 3H).

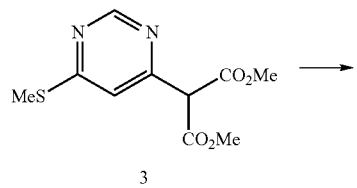

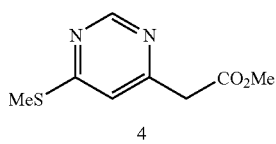

A mixture of 2-(6-methylsulfanyl-pyrimidin-4-yl)-malonic acid dimethyl ester 3 (3.35 g, 13 mmol) and sodium methoxide (0.300 ml of 25% w/v solution, 1.30 mmol, 0.1 eq.) in MeOH (100 ml) is heated at 60° C. for 3 hours. The reaction mixture is cooled to room temperature, neutralized with 1N HCl solution (1.30 mL) and concentrated. The residue, is extracted with ethyl acetate. The organic layer is washed with brine and dried over Na$_2$SO$_4$, filtered and concentrated. The crude product is purified by silica gel flash chromatography eluting with ethyl acetate in hexanes from 0% to 50% to afford (6-methylsulfanyl-pyrimidin-4-yl)-acetic acid methyl ester as a yellow oil. $^1$H NMR 400 MHz (CDCl$_3$) δ 8.86 (s, 1H), 7.18 (s, 1H), 3.73 (s, 3H), 3.70 (s, 2H), 2.55 (s, 3H).

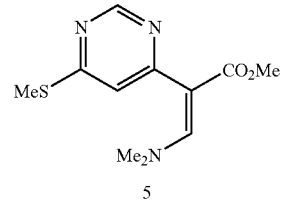

A mixture of (6-methylsulfanyl-pyrimidin-4-yl)-acetic acid methyl ester 4 (4.83 g, 24 mmol) and N,N-dimethylformamide dimethyl acetal (35 mL, 263 mmol.) is heated at 110° C., overnight. The reaction mixture is cooled to room temperature and concentrated and used for next reaction without further purification.

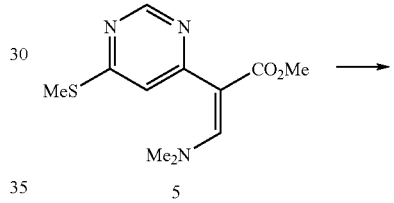

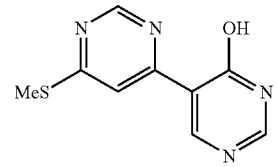

A mixture of crude 5 (1.36 g) and formamidine acetate (2.79 g, 26.8 mmol, 5.0 eq.) in 2-methoxyethanol (20 ml) is heated at 110° C. in a sealed tube for 24 hours. The reaction mixture is cooled to room temperature, concentrated and the solid is filtered and washed with water, dried to give 6-methylsulfanyl-[4,5']bipyrimidinyl-4'-ol as brown solid. $^1$H NMR 400 MHz (DMSO-d$^6$) δ 8.98 (s, 1H), 8.96 (s, 1H), 8.48 (s, 1H), 8.39 (s, 1H), 2.57 (s, 3H).

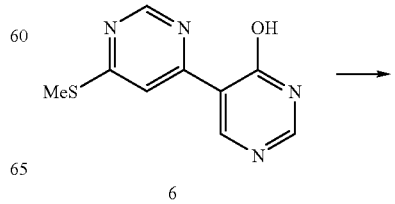

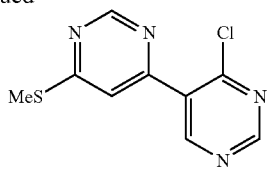

POCl$_3$ (1.51 mL, 16.2 mmol, 3.0 eq.) is added slowly to a suspension of 6-methylsulfanyl-[4,5']bipyrimidinyl-4'-ol 6 (1.20 g, 5.44 mmol) and triethyl amine (0.76 mL, 5.44 mmol, 1.0 eq.) in acetonitrile (30 ml). After heating at 85° C. for 2 hours, the reaction mixture is cooled to room temperature, poured into ice-water, neutralized by saturated NaHCO$_3$ solution, and then extracted with ethyl acetate. The organic layer is washed with brine and dried over Na$_2$SO$_4$, filtered and concentrated. The crude product is purified by silica gel flash chromatography eluting with ethyl acetate in hexanes from 0% to 40% to give 4'-chloro-6-methylsulfanyl-[4,5']bipyrimidinyl as a white solid. $^1$H NMR 400 MHz (DMSO-d$_6$) δ 9.19 (s, 1H), 9.12 (d, 1H, J=1.2 Hz), 9.07 (s, 1H), 7.91 (d, 1H, J=1.6 Hz), 2.62 (s, 3H).

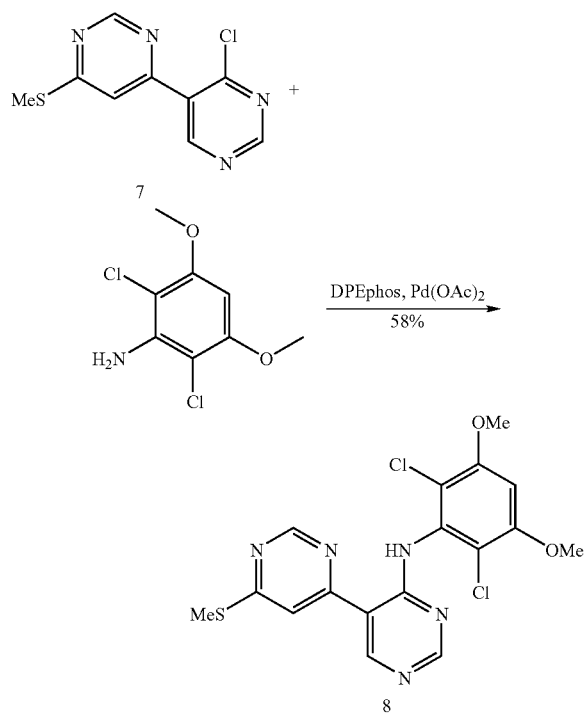

A suspension of chloropyrimidopyrimidine 7 ((10.00 g, 41.9 mmol), 2,6-dichloro-3,5-dimethoxyaniline (10.70 g, 48.2 mmol), DPEphos (4.52 g, 8.39 mmol), palladium (II) acetate (940 mg, 4.19 mmol) and cesium carbonate (27.36, 84.0 mmol) in dioxane (150 mL) is degassed, sealed in a pressure tube. After stirring at 150° C. for 1.5 hours, the reaction mixture is cooled and quenched with 5% diethyldithiocarbamic acid sodium salt solution (200 mL) and water (100 mL). After stirring at room temperature for 30 minutes a brown solid is collected by filtration and washed with water. The crude product is triturated by successively stirring/filtering in hot or cold methanol (3×100 mL) to remove excess aniline, and in CH$_2$Cl$_2$ (100 mL) to remove the ligand. The product is obtained as a brown solid; More product can be obtained by further chromatographic purification of filtrates from trituration. $^1$H NMR 400 MHz (DMSO-d$_6$) δ 11.22 (s, 1H), 9.17 (s, 1H), 9.06 (s, 1H), 8.53 (s, 1H), 8.18 (s, 1H), 6.94 (s, 1H), 3.96 (s, 6H), 2.64 (s, 3H); MS m/z 424.0 (M+1).

To a suspension of the sulfide 8 (3.346 g, 7.88 mmol) in CH$_2$Cl$_2$ (250 mL) is added mCPBA (1.766 g, 7.88 mmol) portion wise over 3 minutes at 0° C. After stirring at 0° C. for 1.5 hours, additional mCPBA (0.34 g, 1.5 mmol) is added and stirred for a further 3.5 hours. More mCPBA (0.17 g, 0.76 mmol) is added and stirred for another hour. The reaction is then quenched with 5% Na$_2$S$_2$O$_3$ (60 mL) and saturated NaHCO$_3$ (40 mL). The aqueous is separated and extracted with EtOAc (2×100 mL). The organics are washed with brine (40 mL), dried over MgSO$_4$, and evaporated to give a yellow solid. The solid is stirred in EtOAc (about 30 mL) for 30 minutes and collected by filtration: MS m/z 440.0 (M+1).

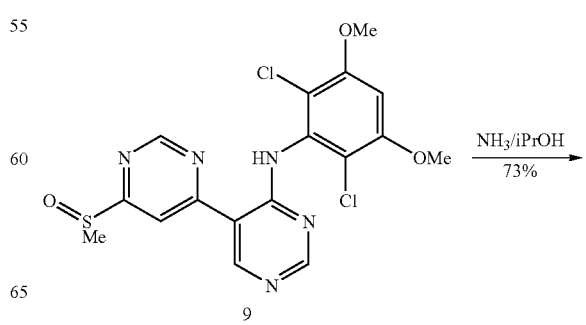

-continued

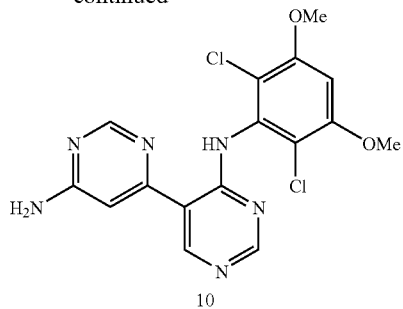

The sulfoxide 9 (3.01 g, 7.27 mmol) is suspended in ammonia/2-propanol solution (2M, 30 mL) in a sealed tube. After stirring at 100° C. overnight, the reaction is cooled to room temperature. The light brown solid is collected by filtration, washed with ether, and dried. The crude is stirred in EtOAc (30 mL) for 30 minutes and filtered to give a light brown solid: $^1$H NMR 400 MHz (DMSO-$d_6$) δ 11.60 (s, 1H), 8.82 (s, 1H), 8.51 (s, 1H), 8.48 (s, 1H), 7.21 (s, 2H), 7.05 (s, 1H), 6.93 (s, 1H), 3.96 (s, 6H); MS m/z 393.1 (M+1).

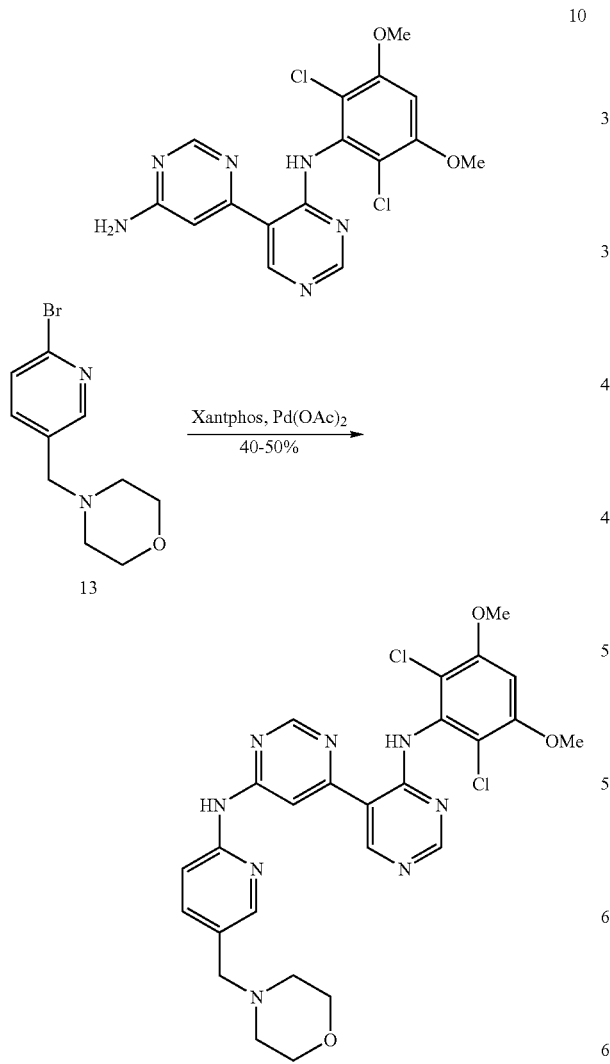

A suspension of aminopyrimidopyrimidine 10 (2.50 g, 6.36 mmol), 4-(6-bromo-pyridin-3-ylmethyl)-morpholine 13 (2.45 g, 9.54 mmol), Xantphos (736 mg, 1.27 mmol), palladium (II) acetate (142 mg, 0.64 mmol) and cesium carbonate (4.14, 12.72 mmol) in dioxane (30 mL) is degassed, sealed in a pressure tube. After stirring at 150° C. for 1.5 hours, the reaction is cooled and quenched with diethyldithiocarbamic acid sodium salt solution (30 mL) and water (30 mL). A brown solid is collected by filtration, washed with water and dried. The crude product triturated by stirring/filtering successively in ether (300 mL) and $CH_2Cl_2$. A light brown solid is collected and the brown color is removed by flash chromatographic purification (SiO$_2$, 1% NH$_3$ in CH$_3$OH/EtOAc from 0 to 10%) to give a white powder: $^1$H NMR 400 MHz (DMSO-$d_6$) δ 11.30 (s, 1H), 10.47 (s, 1H), 8.87 (s, 2H), 8.53 (s, 1H), 8.43 (s, 1H), 8.30 (s, 1H), 7.72 (s, 2H), 6.95 (s, 1H), 3.97 (s, 6H), 3.59 (m, 4H), 3.46 (s, 2H), 2.37 (s, 4H); MS m/z 569.1 (M+1).

Scheme 2

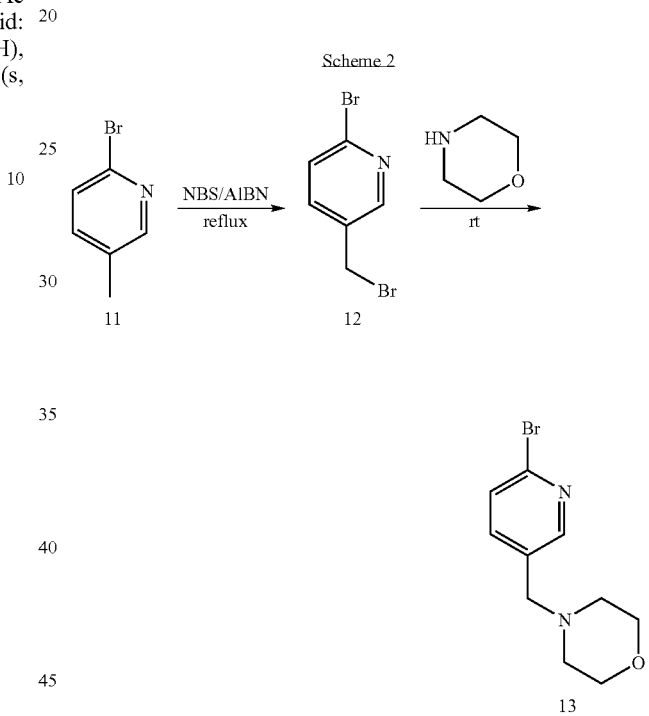

To a suspension of 2-bromo-5-methyl-pyridine 11 (5.00 g, 29 mmol) and NBS (5.162 g, 29 mmol) in CCl$_4$ (40 mL) is added AIBN (0.477 g, 2.9 mmol). The reaction is stirred at 75° C. for 5 hours and filtered. The filter cake is washed with CCl$_4$, and the filtrate is evaporated to give a light yellow residue.

The crude is dissolved in anhydrous THF (40 mL). DIEA (5.03 mL, 29 mmol) is added, followed by addition of morpholine (3.0 mL, 34.3 mmol). After stirring at room temperature for 1 hour, the reaction is partitioned between saturated NaHCO$_3$ (30 mL) and EtOAc (100 mL) and separated. EtOAc is washed with brine (30 mL), dried and evaporated. The crude is purified by flash column chromatography (SiO$_2$, 1% NH$_3$ in CH$_3$OH/CH$_2$Cl$_2$ from 0 to 10%) to give a light tan colored solid: $^1$H NMR 400 MHz (DMSO-$d_6$) δ 8.31 (d, J=2.4 Hz, 1H), 7.69 (dd, J=2.4, 8.4 Hz, 1H), 7.62 (d, J=8.0 Hz, 1H), 3.57 (t, J=4.8 Hz, 4H), 3.48 (s, 2H), 2.35 (t, J=4.4 Hz, 4H); MS m/z 257.1 (M+1).

Scheme 3

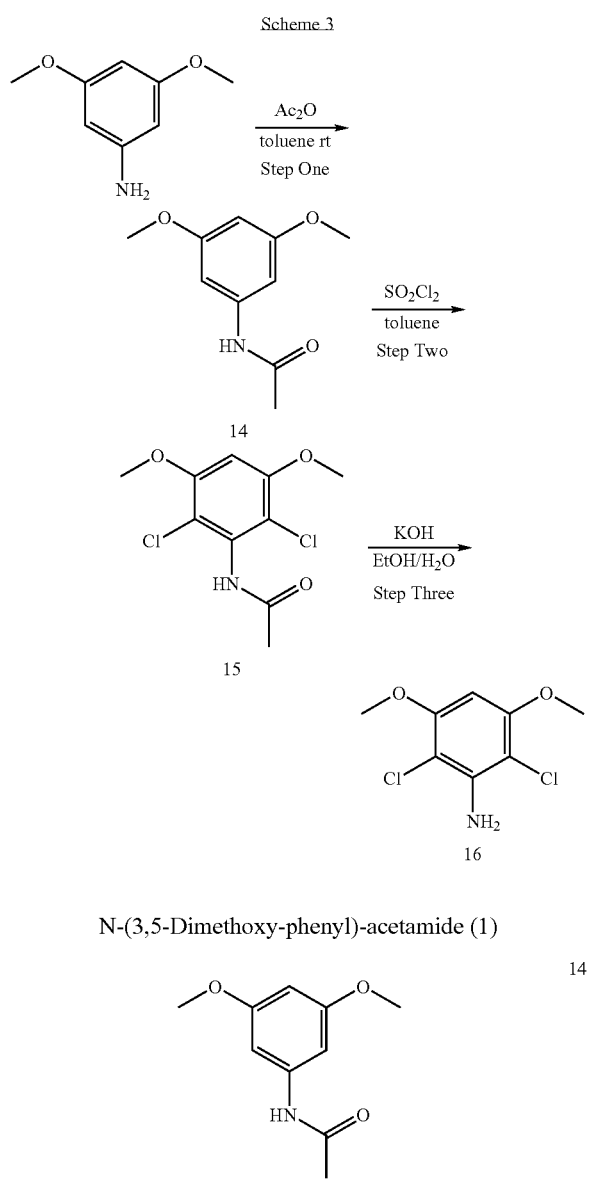

N-(3,5-Dimethoxy-phenyl)-acetamide (1)

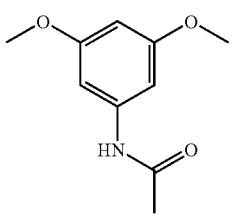

To a solution of 3,5-dimethoxy-phenylamine (22.0 g, 143.6 mmol) in toluene (100 mL), is added slowly Ac₂O (14 mL) at room temperature. After stirring 30 minutes, hexane (50 mL) is added with stirring at room temperature. The resulting solid is filtered and washed with hexane (50 mL) to offer designed product as a white solid 14.

N-(2,6-Dichloro-3,5-dimethoxy-phenyl)-acetamide

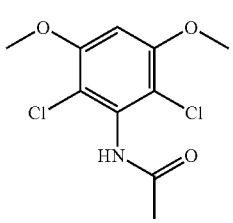

To a suspension of N-(3,5-dimethoxy-phenyl)-acetamide 14 (10.0 g, 51.22 mmol) in MeCN (150 mL), cooled at 0° C., is added slowly sulfuryl chloride (8.23 mL, 101.53 mmol). After stirring for 30 minutes, the solution is warmed to room temperature and stirred overnight. After the solvent (MeCN) is removed on vacuum, NaHCO₃ (Sat., 200 mL) and ethyl acetate (250 mL) are added and stirred for 30 minutes. The white solid is obtained by filtration of above mixture, washed with water and dried to give the product 15: (Rf=0.3: hexane/ethyl acetate, 1:1): MS m/z 264.00 (M+1). The remaining three by-products stay in the solution phase.

2,6-Dichloro-3,5-dimethoxy-phenylamine (16)

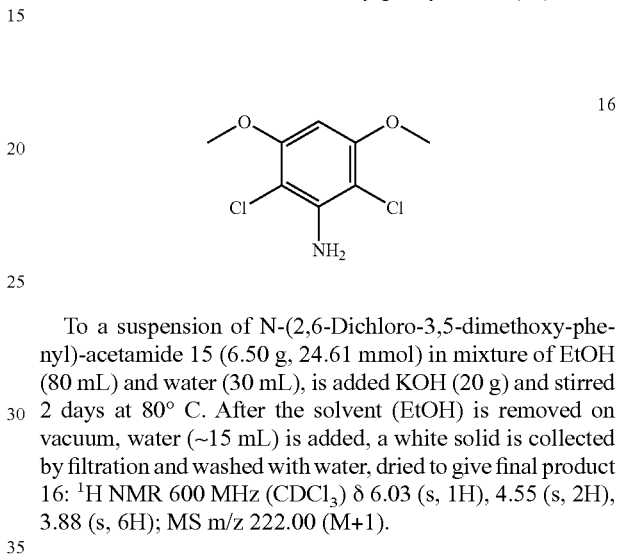

To a suspension of N-(2,6-Dichloro-3,5-dimethoxy-phenyl)-acetamide 15 (6.50 g, 24.61 mmol) in mixture of EtOH (80 mL) and water (30 mL), is added KOH (20 g) and stirred 2 days at 80° C. After the solvent (EtOH) is removed on vacuum, water (~15 mL) is added, a white solid is collected by filtration and washed with water, dried to give final product 16: ¹H NMR 600 MHz (CDCl₃) δ 6.03 (s, 1H), 4.55 (s, 2H), 3.88 (s, 6H); MS m/z 222.00 (M+1).

Scheme 4

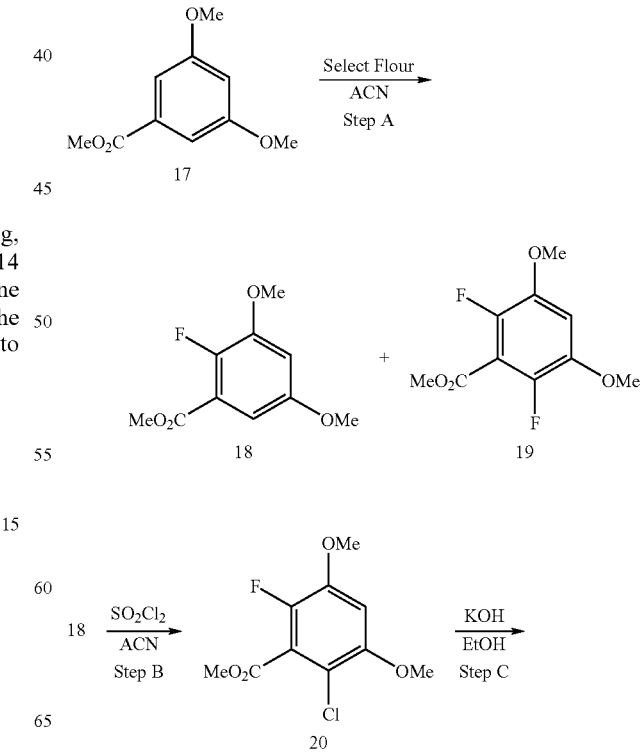

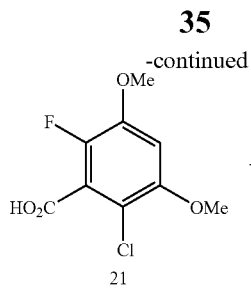

Preparation of Chloro-6-fluoro-3,5-dimethoxy-phenylamine 22

Step A: A solution of methyl 3,5-dimethoxy benzoate 17 (27.6 g, 0.14 mol) in 70 mL acetonitrile is cooled to 0° C. Under nitrogen atmosphere a suspension of Selectfluor (75.0 g, 0.21 mol) in 1.3 L acetonitrile is added keeping the temperature closed to 0° C. The reaction is warmed to room temperature and stirred overnight. The solvent is evaporated and 200 mL saturated sodium carbonate solution is added. It is extracted with EtOAc three times. The organic layer is washed with brine, dried with MgSO$_4$ and concentrated. The crude mixture is separated by silica gel column chromatography eluting with a gradient of hexane to hexane/ether (30/1; 10/1; 7/1; 4/1) to obtain 2-fluoro-3,5-dimethoxy-benzoic acid methyl ester (18); $^1$H NMR 400 MHz (CDCl$_3$) δ 6.91-6.89 (m, 1H), 6.71-6.68 (m, 1H), 3.93 (s, 3H), 3.87 (s, 3H), 3.81 (s, 3H); MS m/z 215.0 (M+1) and 2,6-difluoro-3,5-dimethoxy-benzoic acid methyl ester (19); $^1$H NMR 400 MHz (CDCl$_3$) δ 6.73 (t, 1H), 3.96 (s, 3H), 3.89 (s, 6H); MS m/z 233.0 (M+1).

Step B: Solution of 2-fluoro-3,5-dimethoxy-benzoic acid methyl ester (8.3 g, 38.7 mmol) in 330 mL of acetonitrile is cooled to 0° C. Under nitrogen atmosphere SO$_2$Cl$_2$ (5.2 g, 38.7 mmol) is added dropwise. The reaction mixture is warmed to room temperature slowly. After 1 hour, the reaction is completed. The reaction is quenched with saturated sodium bicarbonate, and extracted with EtOAc three times. The organic layer is washed with brine, dried with MgSO$_4$ and concentrated. The crude mixture is separated by silica gel column chromatography eluting with a gradient of hexane/ether (20:1 to 10:1 and 5:1) to obtain 2-chloro-6-fluoro-3,5-dimethoxy-benzoic acid methyl ester (20); $^1$H NMR 400 MHz (CDCl$_3$) δ 6.64 (d, 1H), 3.97 (s, 3H), 3.91 (s, 3H), 3.89 (s, 3H); MS m/z 249.0 (M+1).

Step C: A suspension of 2-chloro-6-fluoro-3,5-dimethoxy-benzoic acid methyl ester (7.9 g, 31.9 mmol) and sodium hydroxide (3.2 g, 79.6 mmol) in 96 mL of anhydrous ethanol is refluxed for 24 hours. The ethanol is concentrated in vacuo and solid residue is dissolved in water and extracted twice with ether. The aqueous layer is acidified with Conc. HCl and a white precipitate is filtered, washed with cold water and dried in vacuo to afford 2-chloro-6-fluoro-3,5-dimethoxy-benzoic acid (21); $^1$H NMR 400 MHz (CDCl$_3$) δ 6.61 (d, 1H), 3.87 (s, 3H), 3.84 (s, 3H); MS m/z 235.0 (M+1).

Step D: A suspension of 2-chloro-6-fluoro-3,5-dimethoxy-benzoic acid (2.5 g, 10.7 mmol) and triethyl amine (1.29 g, 12.8 mmol) in 60 mL of tert-butanol is stirred for 5 minutes. To the reaction mixture diphenyl phosphoryl azide (3.52 g, 12.8 mmol) is added. The reaction is heated up to 82° C. and kept at this temperature for overnight. The reaction solution is concentrated in vacuo and residue is dissolved in CH$_2$Cl$_2$ (25 mL). TFA (5 mL) is added to the above solution at 0° C. and stirred for 2 hours at room temperature. The solvent is removed in vacuo. Then, ethyl acetate (40 mL) is added and resulting solution is washed twice with saturated potassium carbonate solution, dried, filtered and evaporated. The crude product is purified by column chromatography eluting with a gradient of hexane to hexane/ether (100 to 65/35) to offer product as a solid 22. $^1$H NMR 400 MHz (CDCl$_3$) δ 6.03 (d, 1H), 4.15 (bs, 2H), 3.88 (s, 3H), 3.85 (s, 3H); MS m/z 206.0 (M+1).

Scheme 5

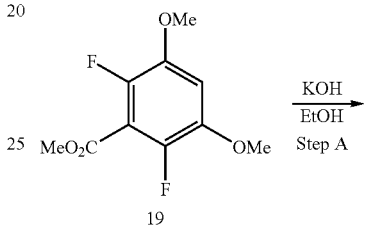

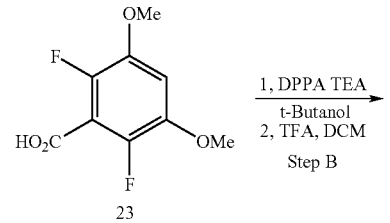

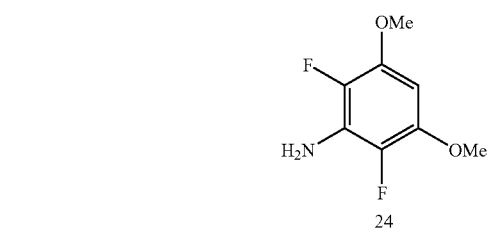

Preparation of 2,6-Difluoro-3,5-dimethoxy-phenylamine 24

Step A: The compound 19 (1.35 g, 5.82 mmol) as a starting material, using the same procedure of Step C (Scheme 4), 2,6-difluoro-3,5-dimethoxy-benzoic acid (23) is obtained (1.21 g, 95.3%) as a solid.

Step B: The compound 23 (0.6 g, 2.75 mmol) as a starting material, using the same procedure of Step D (Scheme 4), 2,6-difluoro-3,5-dimethoxy-phenylamine (24) is obtained as a solid.

37

Scheme 6

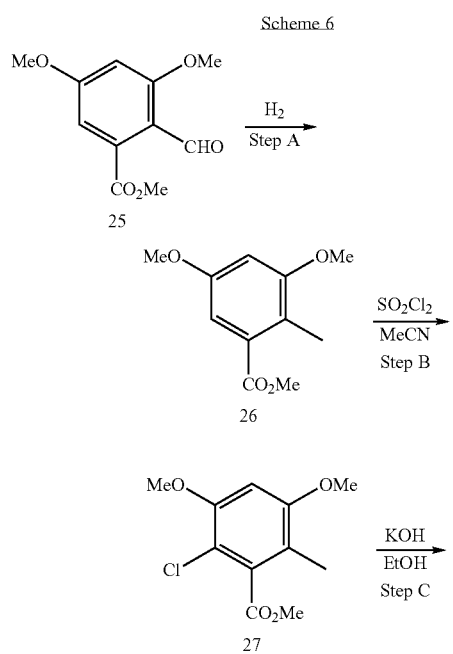

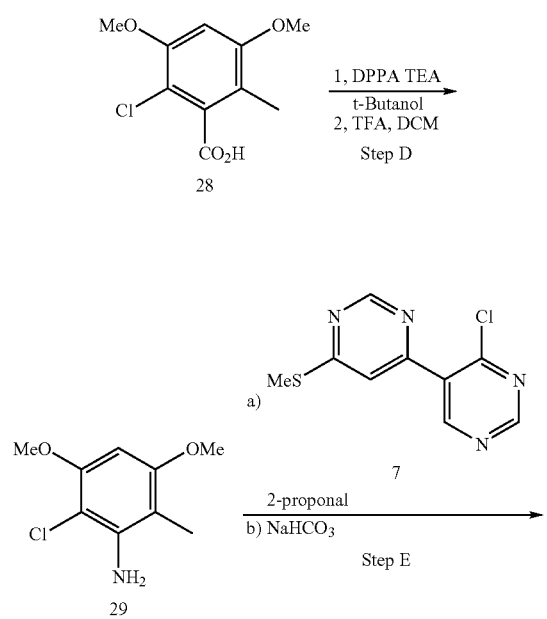

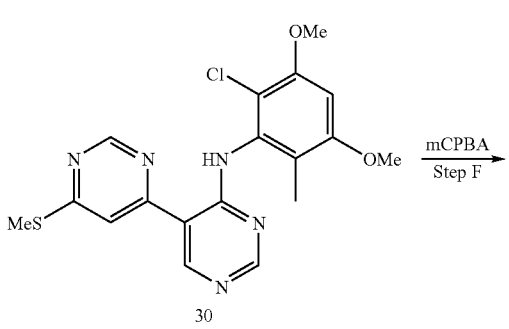

38

-continued

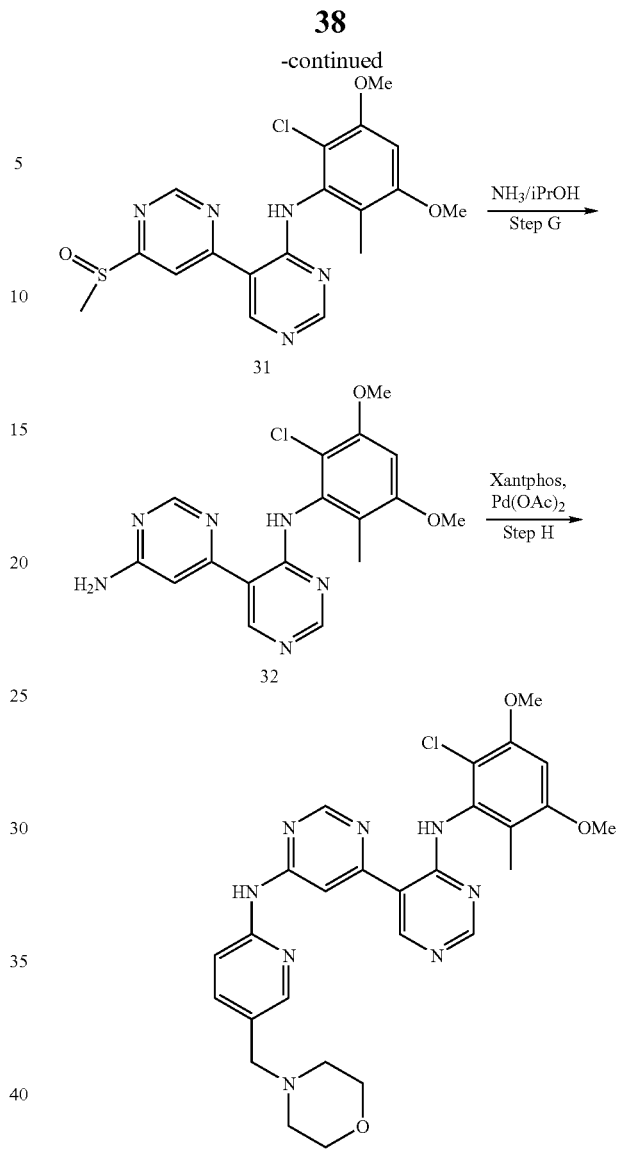

Preparation of N4'-(2-Chloro-3,5-dimethoxy-6-methyl-phenyl)-N6-(5-morpholin-4-ylmethyl-pyridin-2-yl)-[4,5']bipyrimidinyl-6,4'-diamine Step A: A solution of 2-formyl-3,5-dimethoxy-benzoic acid methyl ester 25 (10.0 g, 44.6 mol) in 250 mL ethyl acetate is hydrogenated in the presence of Pd/C (4.5 g, 10%) under the balloon. After the mixture is stirred overnight, the catalyst is filtered off. The solvent is removed to give crude product 26.

Step B: Solution of crude 2-formyl-3,5-dimethoxy-benzoic acid methyl ester 26 (6.0 g, 28.54 mmol) in 60 mL of acetonitrile is carried out the same reaction as in Step B of Scheme 4. The reaction mixture is separated by silica gel column chromatography to obtain 2-Chloro-3,5-dimethoxy-6-methyl-benzoic acid methyl ester 27.

Step C: 2-Chloro-3,5-dimethoxy-6-methyl-benzoic acid methyl ester 27 (3.6 g, 17.75 mmol) is carried out the same reaction as in Step C of Scheme 4 to afford 2-Chloro-3,5-dimethoxy-6-methyl-benzoic acid 28.

Step D: 2-Chloro-3,5-dimethoxy-6-methyl-benzoic acid 28 (3.1 g, 13.47 mmol) is carried out the same reaction as in Step D of Scheme 4 to afford 2-Chloro-3,5-dimethoxy-6-methyl-phenylamine 29.

Step E: A solution of chloro pyrimido pyrimidine 7 ((2.38 g, 9.92 mmol) and 2-Chloro-3,5-dimethoxy-6-methyl-phenylamine 29 (2.0 g, 9.92 mmol) in 2-proponal (250 mL) is heated at 85° C. for 14 hours. After the mixture is cooled to room temperature, the salt is collected by filtration. The solid is suspended in ethyl acetate and neutralized with sat. NaHCO₃ to offer (2-Chloro-3,5-dimethoxy-6-methyl-phenyl)-(6-methylsulfanyl-[4,5']bipyrimidinyl-4'-yl)-amine 30 as pure product.

Step F: Compound 30 (0.8 g, 1.98 mmol) is carried out the same reaction as in Scheme 1 for compound 8 to afford (2-Chloro-3,5-dimethoxy-6-methyl-phenyl)-(6-methanesulfinyl-[4,5']bipyrimidinyl-4'-yl)-amine 31.

Step G: Compound 31 (0.6 g, 1.43 mmol) is carried out the same reaction as in Scheme 1 for compound 9 to afford N4'-(2-Chloro-3,5-dimethoxy-6-methyl-phenyl)-[4,5']bipyrimidinyl-6,4'-diamine 32.

Step H: Compound 32 is carried out the same reaction as in Scheme 1 for compound 10 to afford N4'-(2-Chloro-3,5-dimethoxy-6-methyl-phenyl)-N6-(5-morpholin-4-ylmethyl-pyridin-2-yl)-[4,5']bipyrimidinyl-6,4'-diamine as final product.

By repeating the procedures described in the above examples, using appropriate starting materials, the following compounds of Formula I, as identified in Table 1, are obtained.

TABLE 1

| Compound Number | Structure | Physical Data ¹H NMR 400 MHz (DMSO-d₆) and/or MS (m/z) |
|---|---|---|
| 1 | 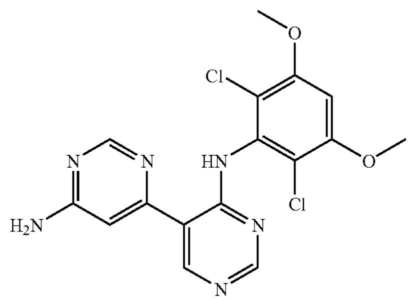 | MS m/z 393.1 (M + 1) |
| 2 | 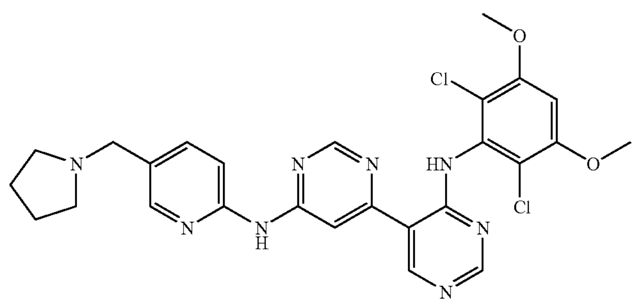 | MS m/z 553.2 (M + 1) |
| 3 | 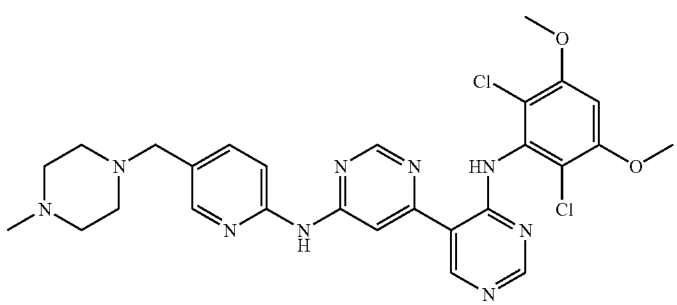 | MS m/z 582.2 (M + 1) |
| 4 | 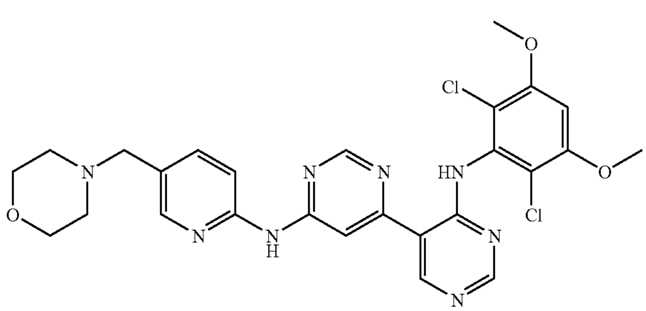 | MS m/z 569.2 (M + 1) |

TABLE 1-continued

| Compound Number | Structure | Physical Data<br>$^1$H NMR 400 MHz<br>(DMSO-$d_6$) and/or MS (m/z) |
|---|---|---|
| 5 | 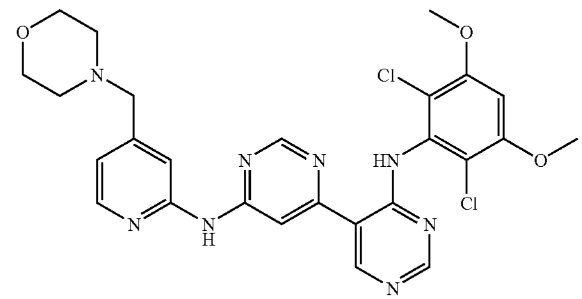 | MS m/z 569.0 (M + 1) |
| 6 | 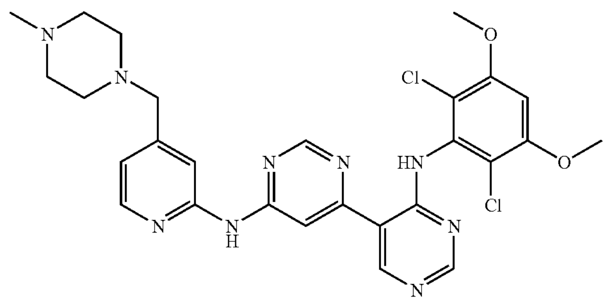 | MS m/z 582.2 (M + 1) |
| 7 | 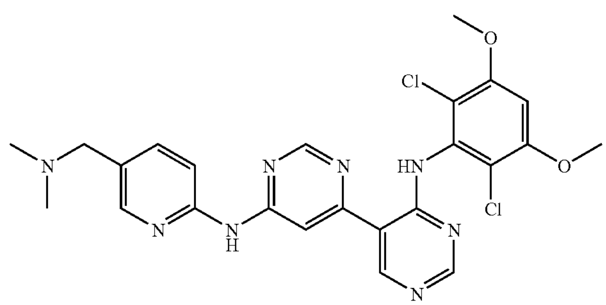 | MS m/z 527.2 (M + 1) |
| 8 | 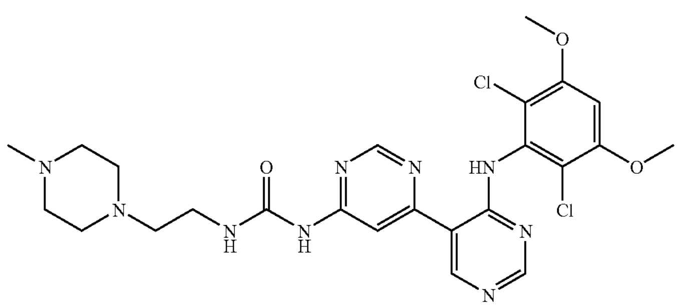 | MS m/z 562.0 (M + 1) |
| 9 | 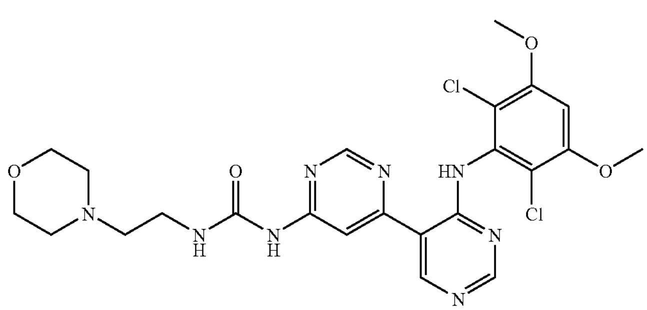 | MS m/z 548.9 (M + 1) |

TABLE 1-continued
| Compound Number | Structure | Physical Data $^1$H NMR 400 MHz (DMSO-$d_6$) and/or MS (m/z) |
|---|---|---|
| 10 | 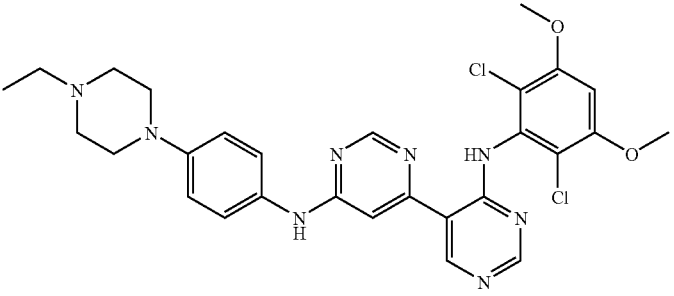 | MS m/z 581.0 (M + 1) |
| 11 | 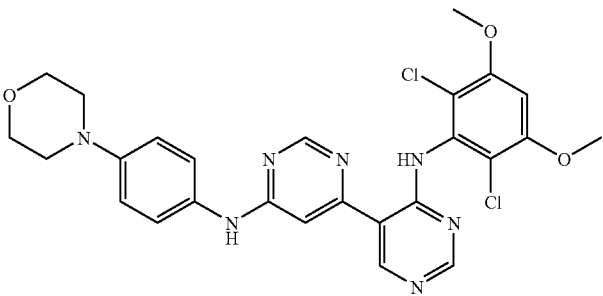 | MS m/z 554.1 (M + 1) |
| 12 | 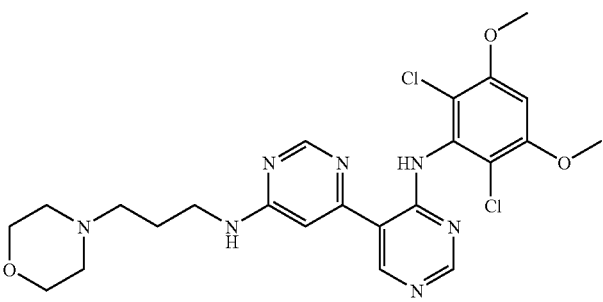 | MS m/z 520.2 (M + 1) |
| 13 | 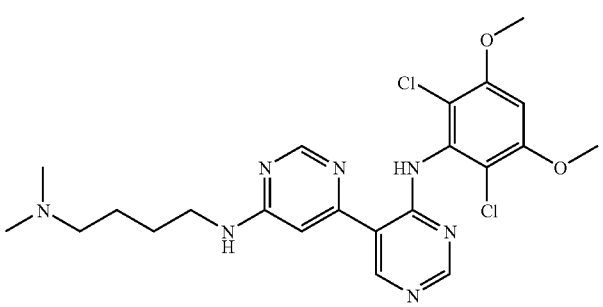 | $^1$H NMR 400 MHz (CD$_3$OD) δ 8.88 (s, 1H), 8.63 (s, 2H), 7.10 (s, 1H), 6.89 (s, 1H), 3.98 (s, 6H), 3.56 (bs, 2H), 3.19 (t, 2H), 2.89 (s, 6H), 1.85-1.72 (m, 4H); MS m/z 492.1 (M + 1) |
| 14 | 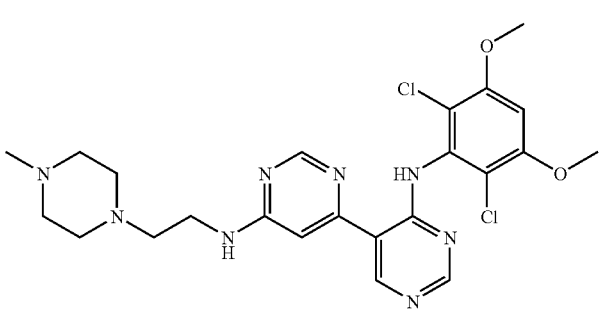 | $^1$H NMR 400 MHz (CD$_3$OD) δ 8.90 (s, 1H), 8.65 (s, 2H), 7.13 (s, 1H), 6.90 (s, 1H), 3.98 (s, 6H), 3.72 (bs, 2H), 2.88 (s, 3H), 3.55-2.64 (m, 10H); MS m/z 519.2 (M + 1) |

TABLE 1-continued

| Compound Number | Structure | Physical Data ¹H NMR 400 MHz (DMSO-d$_6$) and/or MS (m/z) |
|---|---|---|
| 15 | 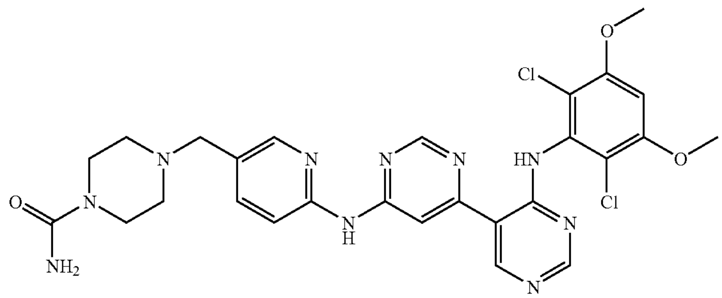 | ¹H NMR 400 MHz (CD$_3$OD) δ 9.02 (s, 1H), 8.93 (s, 1H), 8.62 (s, 1H), 8.50 (s, 1H), 8.43 (s, 1H), 7.94 (d, 1H), 7.88 (d, 1H), 6.90 (s, 1H), 4.40 (s, 2H), 3.98 (s, 6H), 4.29-2.96 (m, 8H); MS m/z 611.2 (M + 1) |
| 16 | 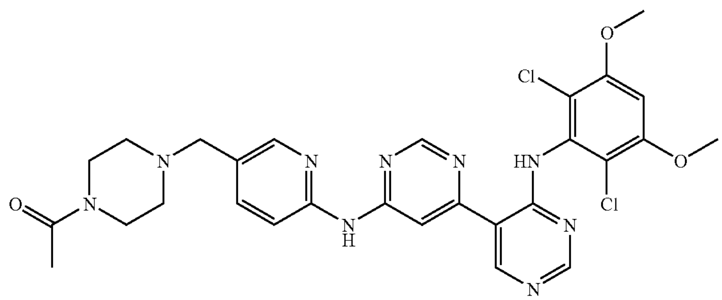 | ¹H NMR 400 MHz (CD$_3$OD) δ 9.05 (s, 1H), 8.94 (s, 1H), 8.68 (s, 1H), 8.50 (s, 1H), 8.42 (s, 1H), 7.95 (d, 1H), 7.89 (d, 1H), 6.91 (s, 1H), 4.40 (s, 2H), 3.99 (s, 6H), 4.08-3.61 (m, 4H), 3.45-3.19 (m, 4H), 2.15 (s, 3H); MS m/z 610.2 (M + 1) |
| 17 | 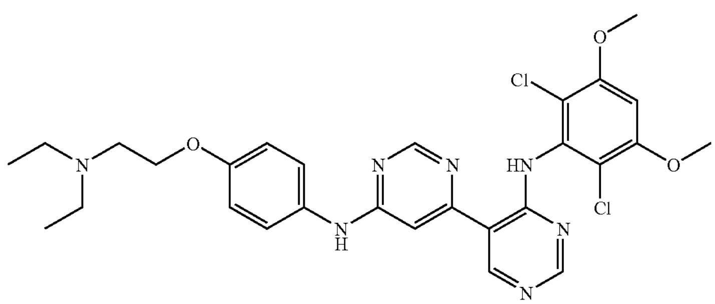 | ¹H NMR 400 MHz (CD$_3$OD) δ 8.89 (s, 1H), 8.71 (s, 1H), 8.60 (s, 1H), 7.61 (d, 2H), 7.24 (s, 1H), 7.08 (d, 2H), 6.89 (s, 1H), 4.37 (t, 2H), 3.98 (s, 6H), 3.63 (t, 2H), 3.38 (q, 4H), 1.38 (t, 6H); MS m/z 584.1 (M + 1) |
| 18 | 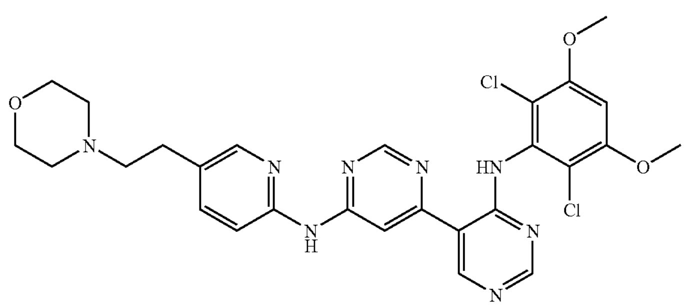 | ¹H NMR 400 MHz (CD$_3$OD) δ 9.04 (s, 1H), 8.95 (s, 1H), 8.64 (s, 1H), 8.36 (d, 1H), 8.24 (s, 1H), 7.93 (d, 1H), 7.71 (d, 1H), 6.91 (s, 1H), 4.09 (bs, 2H), 3.98 (s, 6H), 3.80 (bs, 2H), 3.58 (bs, 2H), 3.46 (t, 2H), 3.24 (bs, 2H), 3.14 (t, 2H); MS m/z 583.1 (M + 1) |
| 19 | 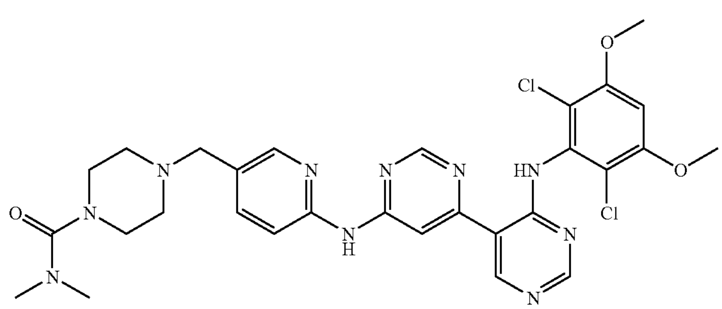 | ¹H NMR 400 MHz (CD$_3$OD) δ 9.02 (s, 1H), 8.93 (s, 1H), 8.63 (s, 1H), 8.50 (s, 1H), 8.44 (s, 1H), 7.94 (d, 1H), 7.88 (d, 1H), 6.90 (s, 1H), 4.40 (s, 2H), 3.98 (s, 6H), 3.92-3.33 (m, 8H), 2.89 (s, 6H); MS m/z 639.1 (M + 1). |

TABLE 1-continued

| Compound Number | Structure | Physical Data ¹H NMR 400 MHz (DMSO-d$_6$) and/or MS (m/z) |
|---|---|---|
| 20 | 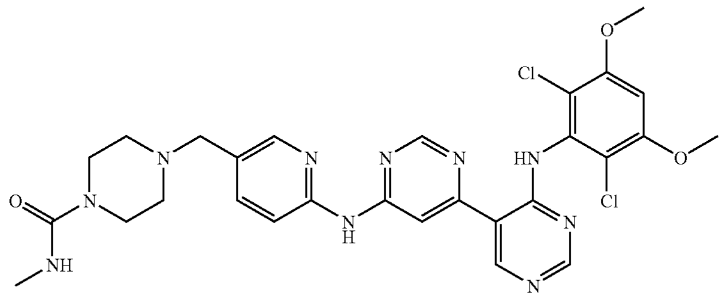 | ¹H NMR 400 MHz (CD$_3$OD) δ 9.04 (s, 1H), 8.93 (s, 1H), 8.66 (s, 1H), 8.50 (s, 1H), 8.44 (s, 1H), 7.94 (d, 1H), 7.87 (d, 1H), 6.91 (s, 1H), 4.40 (s, 2H), 3.99 (s, 6H), 3.93-3.09 (m, 8H), 2.73 (s, 3H); MS m/z 625.1 (M + 1). |
| 21 | 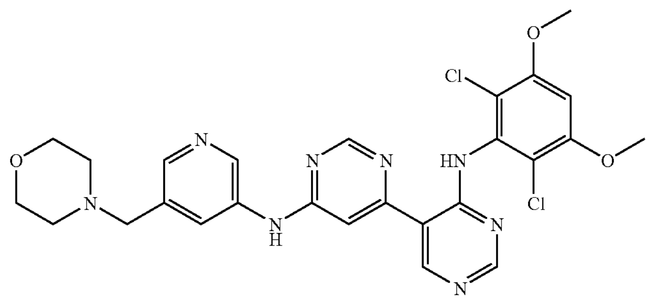 | ¹H NMR 400 MHz (CD$_3$OD) δ 9.81 (s, 1H), 9.30 (s, 1H), 9.11 (s, 1H), 9.06 (s, 1H), 8.85 (s, 1H), 8.80 (s, 1H), 7.76 (s, 1H), 6.95 (s, 1H), 4.70 (s, 2H), 4.00 (s, 6H), 4.14-3.87 (m, 4H), 3.52-3.16 (m, 4H); MS m/z 569.1 (M + 1). |
| 22 | 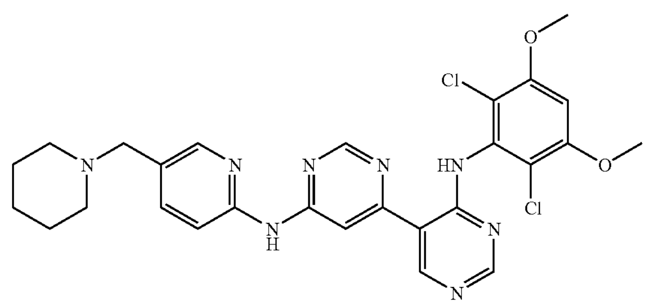 | ¹H NMR 400 MHz (CD$_3$OD) δ 9.04 (bs, 1H), 8.92 (s, 1H), 8.65 (s, 1H), 8.49 (s, 1H), 8.45 (s, 1H), 7.92 (d, 1H), 7.88 (d, 1H), 6.90 (s, 1H), 4.33 (s, 2H), 3.98 (s, 6H), 3.53-3.50 (m, 2H), 3.03-2.96 (m, 2H), 2.03-1.42 (m, 6H); MS m/z 567.2 (M + 1). |
| 23 | 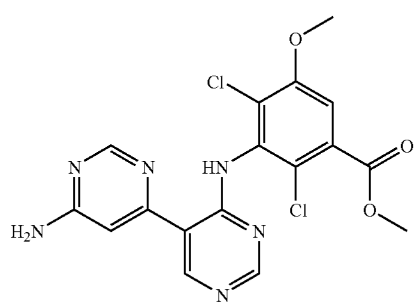 | MS m/z 421.0 (M + 1). |
| 24 | 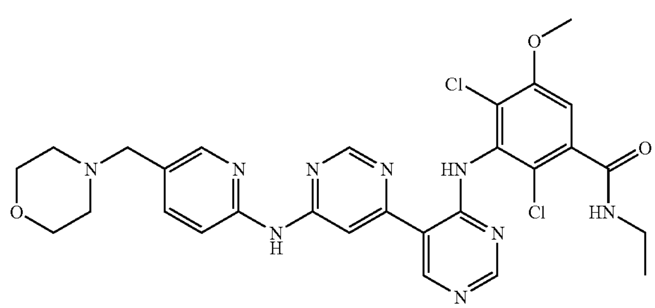 | ¹H NMR 400 MHz (CD$_3$OD) δ 9.03 (s, 1H), 8.93 (s, 1H), 8.62 (s, 1H), 8.52 (s, 1H), 8.46 (s, 1H), 7.92 (d, 1H), 7.89 (d, 1H), 7.23 (s, 1H), 4.41 (s, 2H), 3.99 (s, 3H), 4.26-3.60 (m, 4H), (m, 6H), 1.25 (t, 3H); MS m/z 610.2 (M + 1). |

TABLE 1-continued

| Compound Number | Structure | Physical Data<br>¹H NMR 400 MHz<br>(DMSO-d₆) and/or MS (m/z) |
|---|---|---|
| 25 | 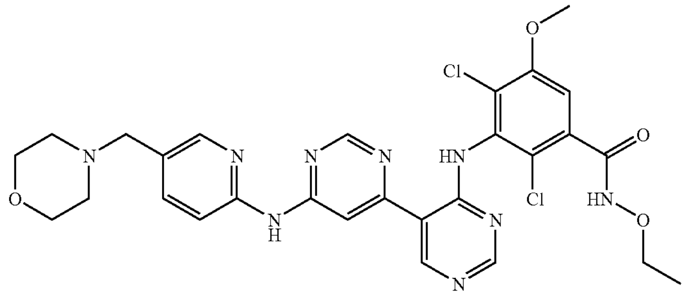 | ¹H NMR 400 MHz (CD₃OD) δ 8.94 (s, 1H), 8.83 (s, 1H), 8.51 (s, 1H), 8.41 (s, 1H), 8.37 (s, 1H), 7.85 (d, 1H), 7.76 (d, 1H), 7.16 (s, 1H), 4.30 (s, 2H), 3.98 (q, 2H), 3.89 (s, 3H), 4.18-3.49 (m, 4H), 3.48-2.99 (m, 4H), 1.23 (t, 3H); MS m/z 626.2 (M + 1). |
| 26 | 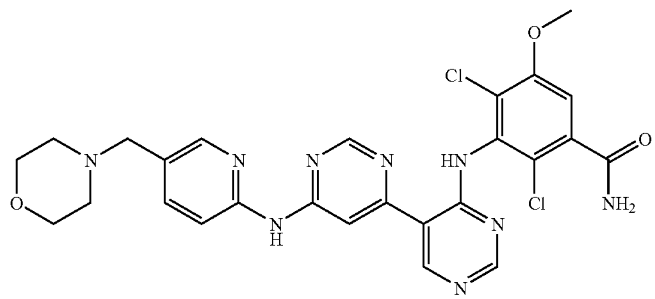 | ¹H NMR 400 MHz (CD₃OD) δ 8.96 (s, 1H), 8.84 (s, 1H), 8.54 (s, 1H), 8.42 (s, 1H), 8.37 (s, 1H), 7.85 (d, 1H), 7.76 (d, 1H), 7.20 (s, 1H), 4.31 (s, 2H), 3.89 (s, 3H), 4.18-3.50 (m, 4H), 3.50-3.00 (m, 4H); MS m/z 582.2 (M + 1). |
| 27 | 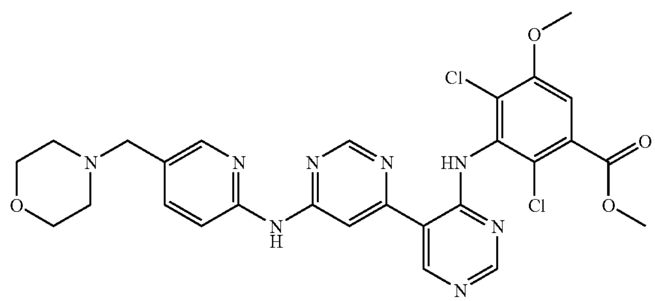 | ¹H NMR 400 MHz (CD₃OD) δ 8.96 (s, 1H), 8.84 (s, 1H), 8.56 (s, 1H), 8.42 (s, 1H), 8.35 (s, 1H), 7.85 (d, 1H), 7.77 (d, 1H), 7.46 (s, 1H), 4.31 (s, 2H), 3.90 (s, 3H), 3.85 (s, 3H), 4.19-3.51 (m, 4H), 3.51-3.00 (m, 4H); MS m/z 597.1 (M + 1). |
| 28 | 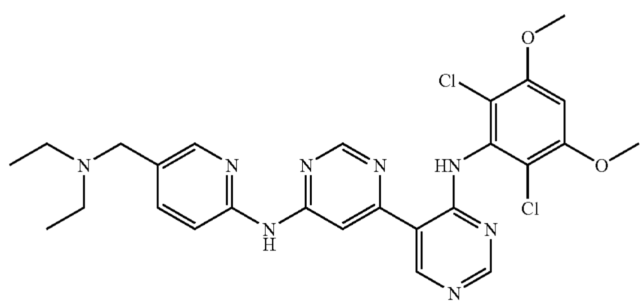 | ¹H NMR 400 MHz (CD₃OD) δ 8.90 (s, 1H), 8.81 (s, 1H), 8.47 (s, 1H), 8.41 (s, 1H), 8.37 (s, 1H), 7.83 (d, 1H), 7.77 (d, 1H), 6.79 (s, 1H), 4.29 (s, 2H), 3.88 (s, 6H), 3.22-3.09 (m, 4H), 1.29 (t, 6H); MS m/z 555.2 (M + 1). |
| 29 | 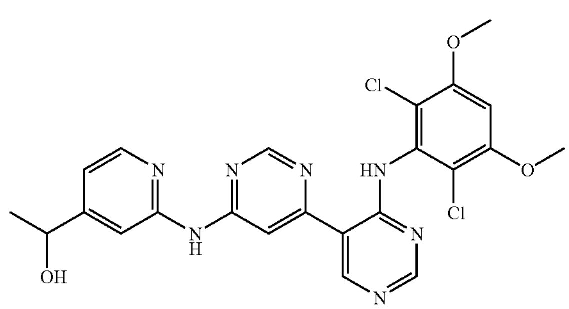 | ¹H NMR 400 MHz (CD₃OD) δ 8.80 (s, 1H), 8.66 (s, 1H), 8.50 (s, 1H), 7.56 (s, 1H), 7.47 (d, 1H), 7.26 (t, 1H), 7.21 (s, 1H), 7.08 (d, 1H), 6.80 (s, 1H), 4.78 (m, 1H), 3.88 (s, 6H), 1.38 (d, 3H); MS m/z 513.1 (M + 1). |

TABLE 1-continued

| Compound Number | Structure | Physical Data ¹H NMR 400 MHz (DMSO-d₆) and/or MS (m/z) |
|---|---|---|
| 30 | 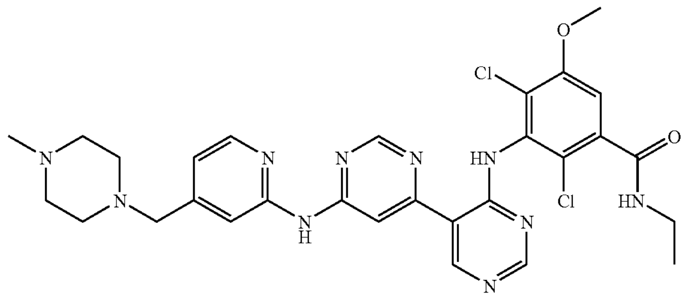 | ¹H NMR 400 MHz (CD₃OD) δ 9.06 (s, 2H), 8.59 (s, 1H), 8.34 (d, 1H), 8.05 (s, 1H), 7.68 (s, 1H), 7.37 (d, 1H), 7.21 (s, 1H), 3.99 (s, 3H), 3.83 (s, 2H), 3.49 (q, 2H), 3.49-3.01 (m, 6H), 2.93 (s, 3H), 2.72-2.44 (m, 2H), 1.24 (t, 3H); MS m/z 623.2 (M + 1). |
| 31 | 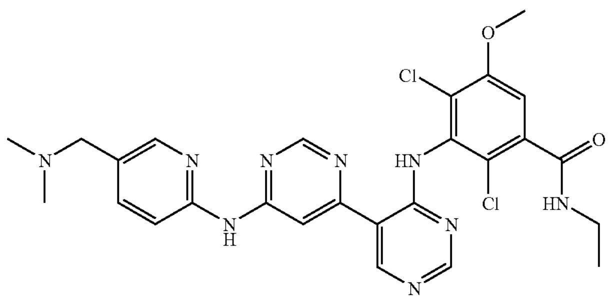 | ¹H NMR 400 MHz (CD₃OD) δ 8.92 (s, 1H), 8.82 (s, 1H), 8.48 (s, 1H), 8.42 (d, 1H), 8.17 (s, 1H), 7.92 (s, 1H), 7.12 (s, 1H), 7.09 (d, 1H), 4.30 (s, 2H), 3.89 (s, 3H), 3.32 (q, 2H), 2.85 (s, 6H), 1.15 (t, 3H); MS m/z 568.1 (M + 1). |
| 32 | 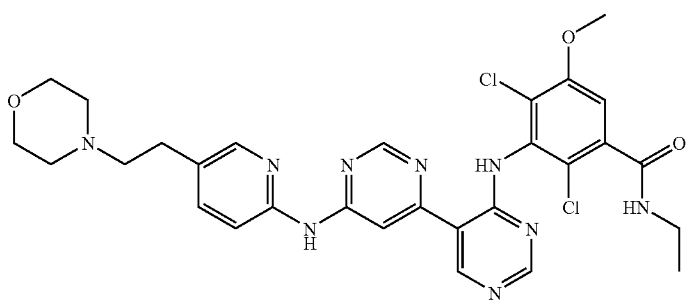 | ¹H NMR 400 MHz (CD₃OD) δ 8.89 (s, 1H), 8.81 (s, 1H), 8.45 (s, 1H), 8.25 (s, 1H), 8.22 (s, 1H), 7.75 (dd, 1H), 7.62 (d, 1H), 7.11 (s, 1H), 3.88 (s, 3H), 4.01 (bs, 2H), 3.70 (bs, 2H), 3.51 (bs, 2H), 3.39 (q, 2H), 3.37-3.30 (m, 4H), 3.07-3.01 (m, 2H), 1.14 (t, 3H); MS m/z 624.1 (M + 1). |
| 33 | 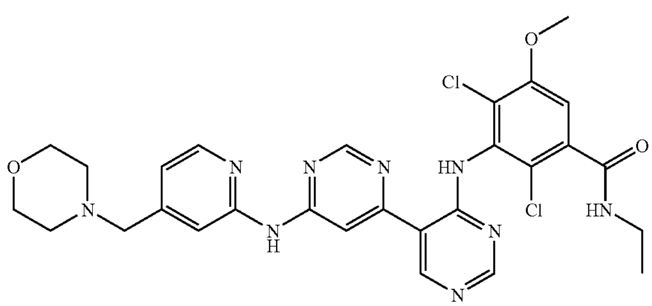 | ¹H NMR 400 MHz (CD₃OD) δ 8.96 (s, 1H), 8.86 (s, 1H), 8.54 (s, 1H), 8.41 (d, 1H), 8.14 (s, 1H), 7.92 (s, 1H), 7.15 (d, 1H), 7.13 (s, 1H), 4.29 (s, 2H), 3.89 (s, 3H), 3.87-3.72 (m, 4H), 3.33 (q, 2H), 3.28-3.12 (m, 4H), 1.15 (t, 3H); MS m/z 610.2 (M + 1). |
| 34 | 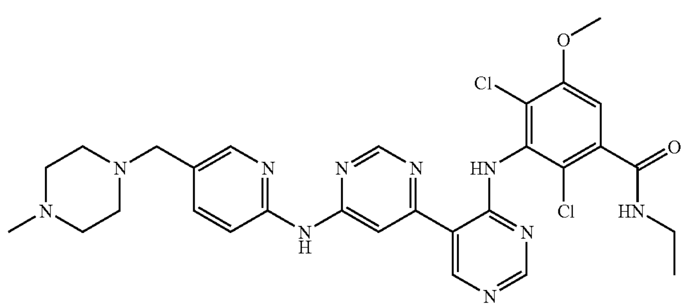 | ¹H NMR 400 MHz (CD₃OD) δ 9.04 (s, 1H), 9.00 (s, 1H), 8.59 (s, 1H), 8.37 (s, 1H), 8.20 (s, 1H), 8.03 (dd, 1H), 7.68 (d, 1H), 7.23 (s, 1H), 3.99 (s, 3H), 3.73 (s, 2H), 3.43 (q, 2H), 3.67-2.18 (m, 8H), 1.25 (t, 3H); MS m/z 623.2 (M + 1). |

TABLE 1-continued

| Compound Number | Structure | Physical Data ¹H NMR 400 MHz (DMSO-$d_6$) and/or MS (m/z) |
|---|---|---|
| 35 | 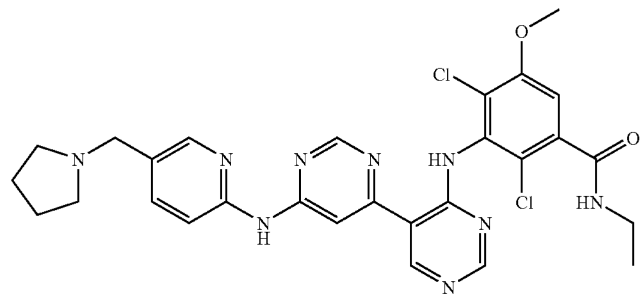 | ¹H NMR 400 MHz (CD$_3$OD) δ 8.93 (s, 1H), 8.82 (s, 1H), 8.50 (s, 1H), 8.42 (s, 1H), 8.35 (s, 1H), 7.85 (dd, 1H), 7.76 (d, 1H), 7.12 (s, 1H), 4.32 (s, 2H), 3.89 (s, 3H), 3.53-3.41 (m, 2H), 3.33 (q, 2H), 3.18-3.07 (m, 2H), 2.19-2.04 (m, 2H), 2.04-1.75 (m, 2H), 1.15 (t, 3H); MS m/z 594.1 (M + 1). |
| 36 | 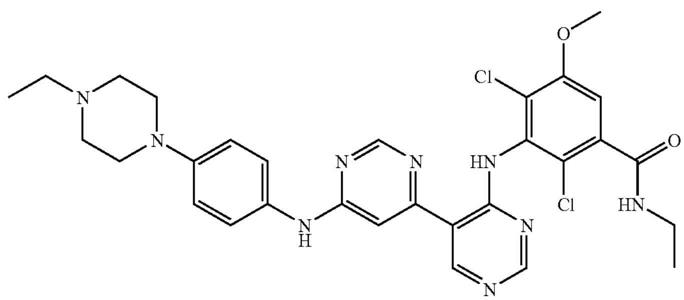 | ¹H NMR 400 MHz (CD$_3$OD) δ 8.79 (s, 1H), 8.60 (s, 1H), 8.47 (s, 1H), 7.49 (s, 1H), 7.47 (s, 1H), 7.14 (d, 2H), 7.00 (d, 2H), 3.88 (s, 3H), 3.82-3.71 (m, 2H), 3.32-3.28 (m, 2H), 3.28-3.10 (m, 4H), 3.06-2.90 (m, 2H), 1.31 (t, 3H), 1.14 (t, 3H); MS m/z 622.2 (M + 1). |
| 37 | 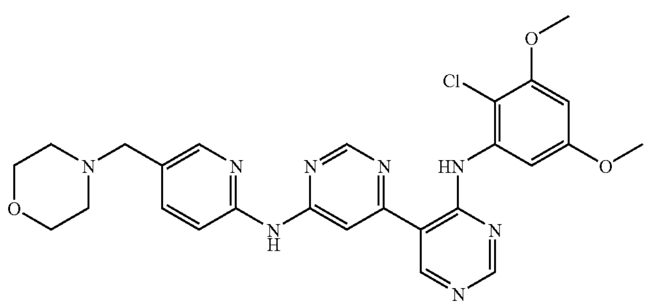 | ¹H NMR 400 MHz (CD$_3$OD) δ 8.94 (s, 1H), 8.86 (s, 1H), 8.74 (s, 1H), 8.41 (s, 1H), 8.30 (s, 1H), 7.85 (d, 1H), 7.79 (d, 1H), 7.64 (s, 1H), 3.82 (s, 3H), 3.75 (s, 3H), 4.17-3.49 (m, 4H), 3.48-2.92 (m, 4H), 3.40-2.87 (m, 6H), 1.31 (t, 3H); MS m/z 535.2 (M + 1). |
| 38 | 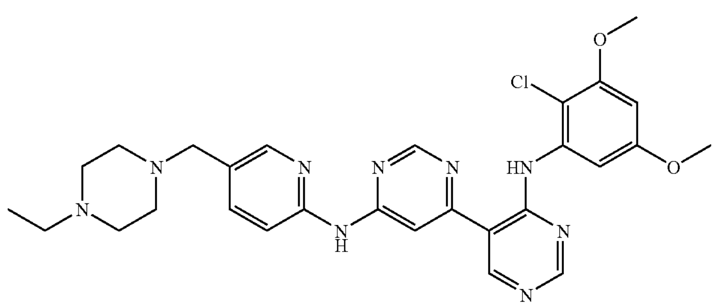 | MS m/z 562.2 (M + 1). |
| 39 | 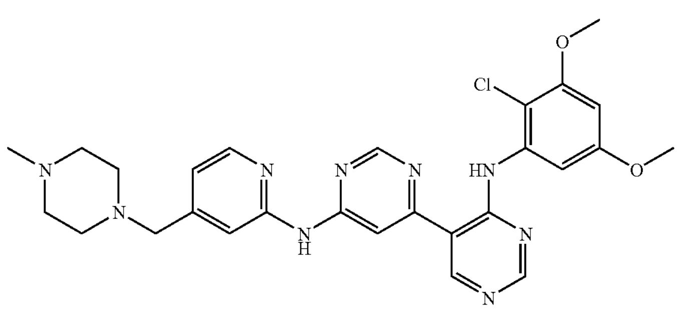 | ¹H NMR 400 MHz (CD$_3$OD) δ 8.97 (s, 1H), 8.94 (s, 1H), 8.71 (s, 1H), 8.28 (d, 1H), 7.95 (s, 1H), 7.76 (s, 1H), 7.59 (s, 1H), 7.25 (d, 1H), 6.43 (s, 1H), 3.81 (s, 3H), 3.75 (s, 3H), 3.72 (s, 2H), 3.53-2.91 (m, 6H), 2.84 (s, 3H), 2.62-2.34 (m, 2H), MS m/z 548.2 (M + 1). |

TABLE 1-continued

| Compound Number | Structure | Physical Data<br>¹H NMR 400 MHz<br>(DMSO-d₆) and/or MS (m/z) |
|---|---|---|
| 40 | 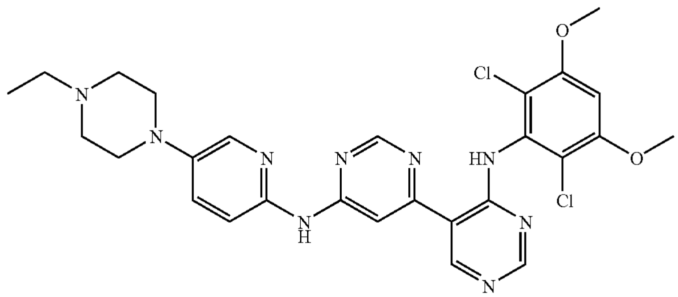 | ¹H NMR 400 MHz (CD₃OD)<br>δ 8.81 (s, 1H), 8.72 (s, 1H),<br>8.37 (s, 1H), 8.11 (s, 1H),<br>8.05 (s, 1H), 7.58 (d, 1H),<br>7.52 (d, 1H), 6.77 (s, 1H),<br>3.88 (s, 6H), 3.90-3.68 (m, 2H), 3.68-3.42<br>(m, 2H), 3.40-2.87<br>(m, 6H), 1.31 (t, 3H);<br>MS m/z 582.1 (M + 1). |
| 41 | 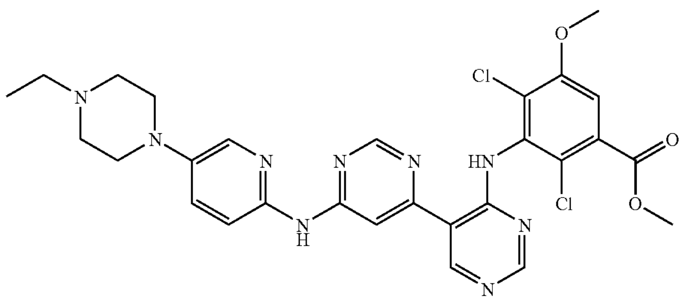 | ¹H NMR 400 MHz (CD₃OD)<br>δ 8.89 (s, 1H), 8.81 (s, 1H),<br>8.48 (s, 1H), 8.02 (s, 1H),<br>8.01 (s, 1H), 7.68 (d, 1H),<br>7.56 (d, 1H), 7.44 (s, 1H),<br>3.90 (s, 3H), 3.85 (s, 3H),<br>3.96-3.72 (m, 2H), 3.71-3.48<br>(m, 2H), 3.32-2.94 (m, 6H),<br>1.32 (t, 3H); MS m/z 610.1<br>(M + 1). |
| 42 | 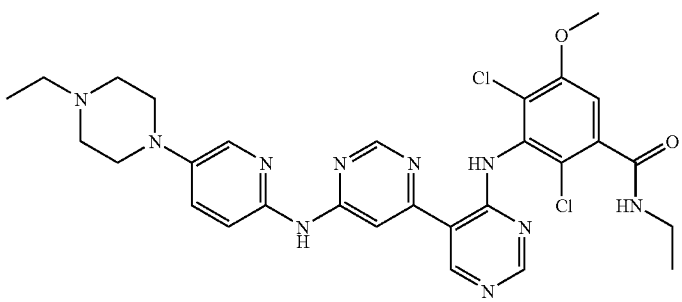 | ¹H NMR 400 MHz (CD₃OD)<br>δ 8.90 (s, 1H), 8.82 (s, 1H),<br>8.47 (s, 1H), 8.01 (s, 1H),<br>7.97 (s, 1H), 7.73 (d, 1H),<br>7.55 (d, 1H), 7.11 (s, 1H),<br>3.88 (s, 3H), 3.86-3.71 (m, 2H), 3.71-3.51 (m, 2H)<br>3.37-3.28 (m, 2H),<br>3.28-2.95 (m,<br>6H), 1.32 (t, 3H), 1.15 (t, 3H); MS m/z 623.1 (M + 1). |
| 43 | 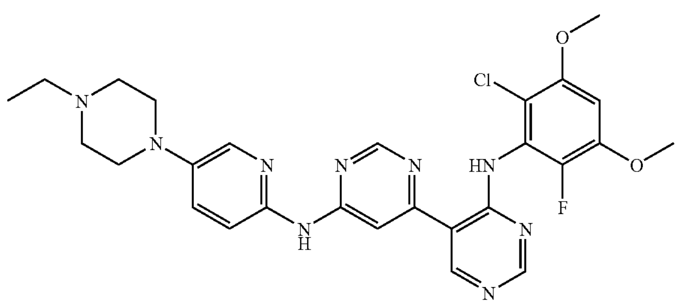 | ¹H NMR 400 MHz (CD₃OD)<br>δ 8.99 (s, 1H), 8.92 (s, 1H),<br>8.62 (s, 1H), 8.11 (s, 1H),<br>8.07 (s, 1H), 7.81 (d, 1H),<br>7.66 (d, 1H), 6.91 (d, 1H),<br>3.96 (s, 3H), 3.95 (s, 3H),<br>4.07-3.610 (m, 4H),<br>3.43-3.01<br>(m, 4H), 1.42 (t, 3H);<br>MS m/z 566.1 (M + 1). |
| 44 | 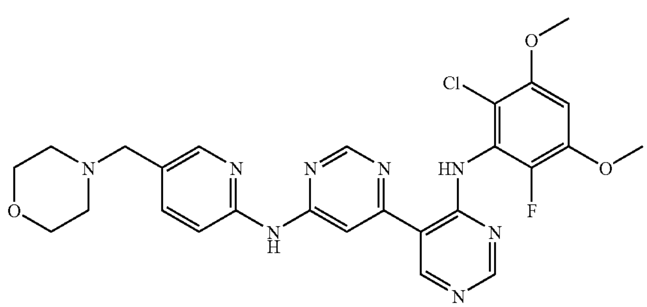 | ¹H NMR 400 MHz (CD₃OD)<br>δ 8.96 (s, 1H), 8.84 (s, 1H),<br>8.61 (s, 1H), 8.42 (s, 1H),<br>8.33 (s, 1H), 7.86 (dd, 1H),<br>7.78 (d, 1H), 6.84 (d, 1H),<br>4.31 (s, 2H), 3.87 (s, 3H),<br>3.85 (s, 3H), 4.11-3.50 (m, 4H), 3.49-2.94 (m, 4H); MS<br>m/z 553.0 (M + 1). |

TABLE 1-continued

| Compound Number | Structure | Physical Data $^1$H NMR 400 MHz (DMSO-$d_6$) and/or MS (m/z) |
|---|---|---|
| 45 | 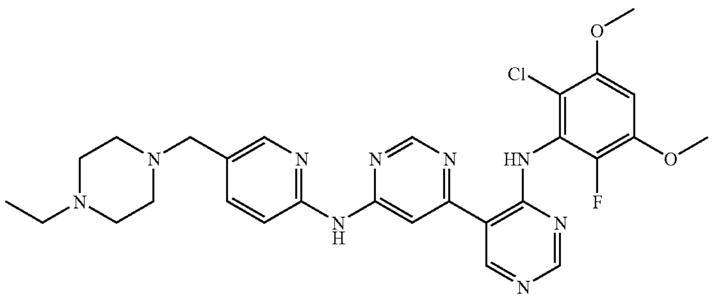 | $^1$H NMR 400 MHz (CD$_3$OD) δ 9.02 (s, 1H), 8.61 (s, 1H), 8.30 (d, 1H), 7.96 (s, 1H), 7.64 (s, 1H), 7.34 (d, 1H), 6.84 (d, 1H), 3.87 (s, 3H), 3.85 (s, 3H), 3.77 (s, 2H), 3.49 (bs, 2H), 3.18 (q, 2H), 3.21-2.89 (m, 4H), 2.52 (bs, 2H), 1.27 (t, 3H); MS m/z 580.1 (M + 1). |
| 46 | 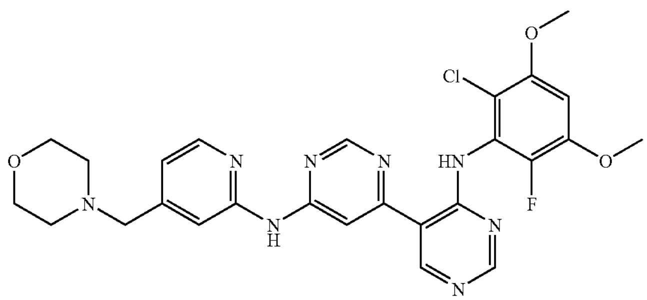 | $^1$H NMR 400 MHz (CD$_3$OD) δ 8.94 (s, 1H), 8.85 (s,1H), 8.58 (s, 1H), 8.40 (d, 1H), 8.13 (s, 1H), 7.91 (s, 1H), 7.15 (d, 1H), 6.83 (d, 1H), 4.28 (s, 2H), 3.86 (s, 3H), 3.85 (s, 3H), 3.82 (bs, 4H), 3.21 (bs, 4H); MS m/z 553.0 (M + 1). |
| 47 | 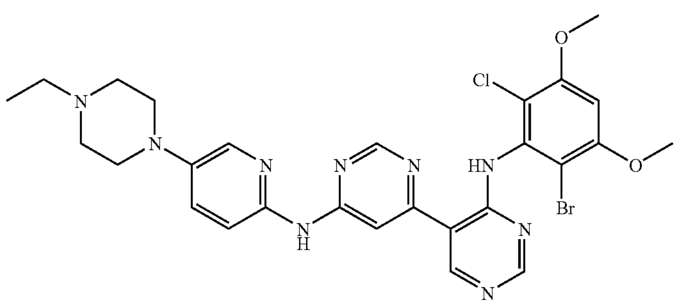 | $^1$H NMR 400 MHz (CD$_3$OD) δ 8.88 (s, 1H), 8.80 (s, 1H), 8.46 (s, 1H), 8.01 (s, 1H), 8.00 (s, 1H), 7.67 (d, 1H), 7.55 (d, 1H), 6.77 (s, 1H), 3.88 (s, 6H), 3.86-3.50 (m, 4H), 3.48-2.90 (m, 4H), 1.31 (t, 3H); MS m/z 626.0 (M + 1). |
| 48 | 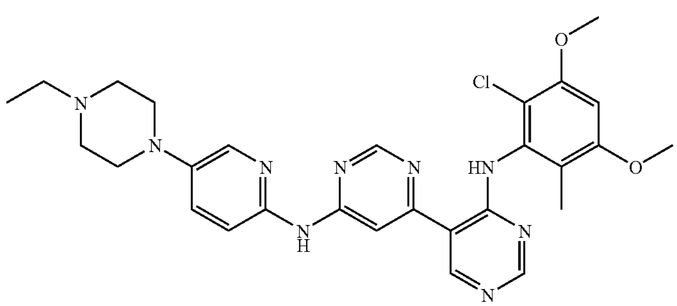 | $^1$H NMR 400 MHz (CD$_3$OD) δ 8.87 (s, 1H), 8.81 (s, 1H), 8.50 (s, 1H), 8.01 (s, 1H), 7.99 (s, 1H), 7.68 (d, 1H), 7.57 (d, 1H), 6.69 (s, 1H), 3.84 (s, 3H), 3.82 (s, 3H), 3.94-3.47 (m, 4H), 3.41-2.95 (m, 4H), 1.95 (s, 3H), 1.31 (t, 3H); MS m/z 562.1 (M + 1). |
| 49 | 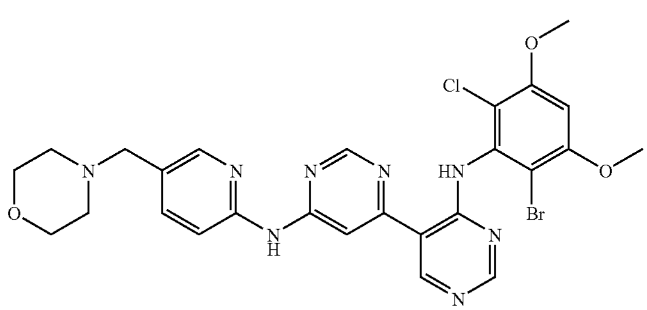 | $^1$H NMR 400 MHz (CD$_3$OD) δ 8.93 (s, 1H), 8.83 (s, 1H), 8.53 (s, 1H), 8.41 (s, 1H), 8.35 (s, 1H), 7.85 (dd, 1H), 7.78 (d, 1H), 6.79 (s, 1H), 4.30 (s, 2H), 3.89 (s, 3H), 3.88 (s, 3H), 4.10-3.51 (m, 4H), 3.48-2.92 (m, 4H); MS m/z 613.0 (M + 1). |

TABLE 1-continued

| Compound Number | Structure | Physical Data ¹H NMR 400 MHz (DMSO-d$_6$) and/or MS (m/z) |
|---|---|---|
| 50 | 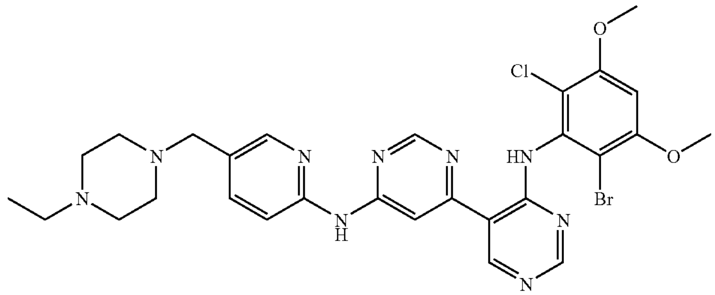 | ¹H NMR 400 MHz (CD$_3$OD) δ 8.97 (s, 1H), 8.52 (s, 1H), 8.28 (d, 1H), 8.01 (s, 1H), 7.59 (s, 1H), 7.28 (d, 1H), 6.79 (s, 1H), 3.89 (s, 3H), 3.88 (s, 3H), 3.73 (s, 2H), 3.50 (bs, 2H), 3.16 (q, 2H), 3.12-2.94 (m, 4H), 2.50 (bs, 2H), 1.27 (t, 3H); MS m/z 640.0 (M + 1). |
| 51 | 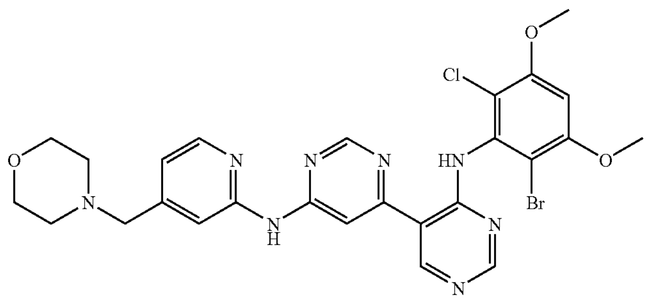 | ¹H NMR 400 MHz (CD$_3$OD) δ 8.94 (s, 1H), 8.85 (s, 1H), 8.52 (s, 1H), 8.40 (d, 1H), 8.14 (s, 1H), 7.92 (s, 1H), 7.15 (d, 1H), 6.79 (s, 1H), 4.28 (s, 2H), 3.89 (s, 3H), 3.88 (s, 3H), 3.82 (bs, 4H), 3.21 (bs, 4H); MS m/z 613.0 (M + 1). |
| 52 | 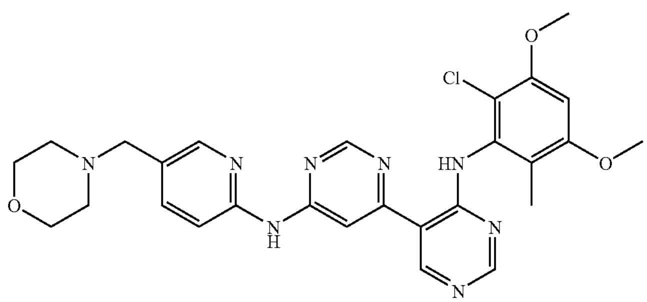 | ¹H NMR 400 MHz (CD$_3$OD) δ 8.90 (s, 1H), 8.83 (s, 1H), 8.54 (s, 1H), 8.41 (s, 1H), 8.33 (s, 1H), 7.85 (dd, 1H), 7.79 (d, 1H), 6.69 (s, 1H), 4.31 (s, 2H), 3.96 (bs, 2H), 3.85 (s, 3H), 3.83 (s, 3H), 3.65 (bs, 2H), 3.47-2.95 (m, 4H), 1.95 (s, 3H); MS m/z 549.1 (M + 1). |
| 53 | 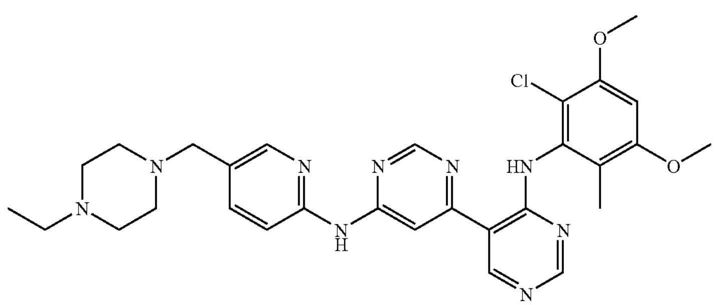 | ¹H NMR 400 MHz (CD$_3$OD) δ 8.97 (s, 1H), 8.54 (s, 1H), 8.29 (d, 1H), 8.04 (s, 1H), 7.61 (s, 1H), 7.28 (d, 1H), 6.69 (s, 1H), 3.85 (s, 3H), 3.83 (s, 3H), 3.73 (s, 2H), 3.48 (bs, 2H), 3.16 (q, 2H), 3.14-2.92 (m, 4H), 2.49 (bs, 2H), 1.95 (s, 3H), 1.27 (t, 3H); MS m/z 576.2 (M + 1). |
| 54 | 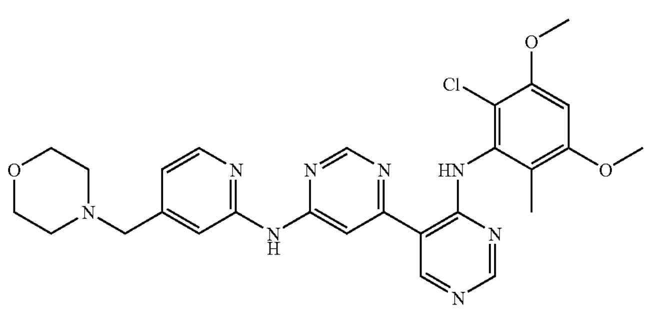 | ¹H NMR 400 MHz (CD$_3$OD) δ 8.93 (s, 1H), 8.86 (s, 1H), 8.56 (s, 1H), 8.41 (d, 1H), 8.18 (s, 1H), 7.90 (s, 1H), 7.15 (d, 1H), 6.70 (s, 1H), 4.30 (s, 2H), 3.85 (s, 3H), 3.83 (s, 3H), 3.82 (bs, 4H), 3.22 (bs, 4H), 1.96 (s, 3H); MS m/z 549.1 (M + 1). |

TABLE 1-continued

| Compound Number | Structure | Physical Data ¹H NMR 400 MHz (DMSO-d₆) and/or MS (m/z) |
|---|---|---|
| 55 | 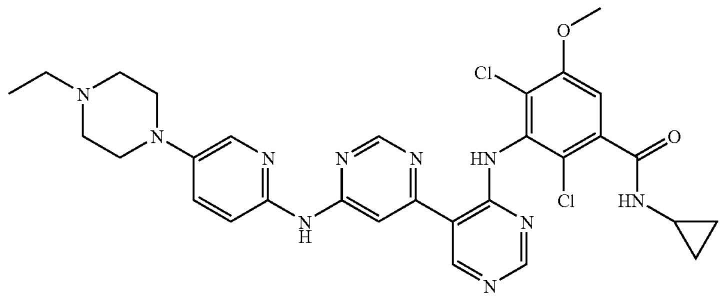 | ¹H NMR 400 MHz (CD₃OD) δ 9.01 (s, 2H), 8.93 (s, 1H), 8.57 (s, 1H), 8.10 (s, 1H), 8.06 (s, 1H), 7.84 (d, 1H), 7.65 (d, 1H), 7.21 (s, 1H), 3.98 (s, 3H), 4.12-3.60 (m, 4H), 3.55-3.02 (m, 4H), 2.94-2.81 (m, 1H), 1.42 (t, 3H), 0.91-0.76 (m, 2H), 0.72-0.60 (m, 2H); MS m/z 635.1 (M + 1). |
| 56 | 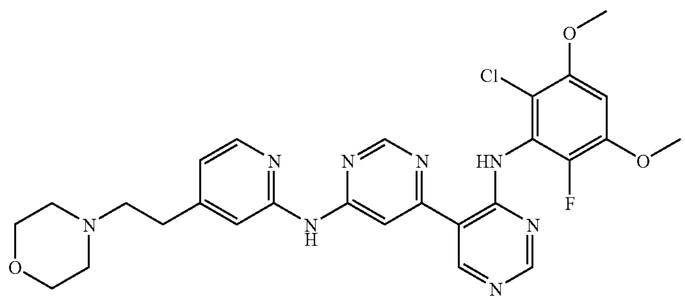 | ¹H NMR 400 MHz (CD₃OD) δ 8.94 (s, 1H), 8.87 (s, 1H), 8.58 (s, 1H), 8.27 (d, 1H), 8.12 (s, 1H), 7.85 (d, 1H), 7.61 (d, 1H), 6.83 (d, 1H), 4.00 (bs, 2H), 3.86 (s, 3H), 3.85 (s, 3H), 3.73 (bs, 4H), 3.50 (bs, 2H), 3.36 (t, 2H), 3.16 (bs, 2H), 3.05 (t, 2H); MS m/z 567.1 (M + 1). |
| 57 | 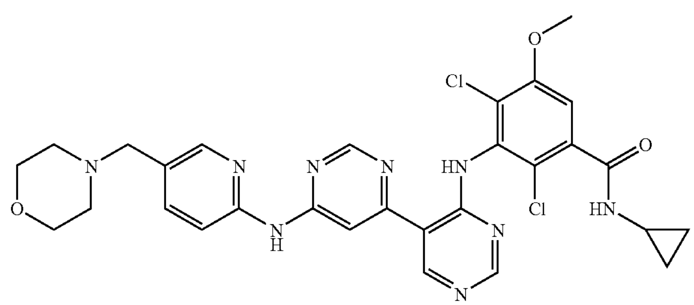 | ¹H NMR 400 MHz (CD₃OD) δ 8.95 (s, 1H), 8.83 (s, 1H), 8.52 (s, 1H), 8.42 (s, 1H), 8.36 (s, 1H), 7.85 (d, 1H), 7.77 (d, 1H), 7.12 (s, 1H), 4.31 (s, 2H), 3.88 (s, 3H), 4.18-3.49 (m, 4H), 3.43-3.00 (m, 4H), 2.80-2.76 (m, 1H), 0.78-0.69 (m, 2H), 0.59-0.49 (m, 2H); MS m/z 622.1 (M + 1). |
| 58 | 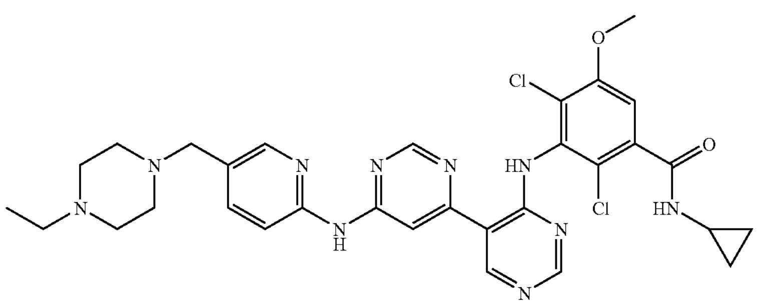 | ¹H NMR 400 MHz (CD₃OD) δ 8.95 (s, 2H), 8.48 (s, 1H), 8.29 (d, 1H), 7.98 (s, 1H), 7.58 (s, 1H), 7.26 (d, 1H), 7.10 (s, 1H), 3.88 (s, 3H), 3.72 (s, 2H), 3.50 (bs, 2H), 3.16 (q, 2H), 3.04 (bs, 4H), 2.80-2.77 (m, 1H), 2.49 (bs, 2H), 1.27 (t, 3H), 0.78-0.70 (m, 2H), 0.60-0.49 (m, 2H); MS m/z 649.1 (M + 1). |
| 59 | 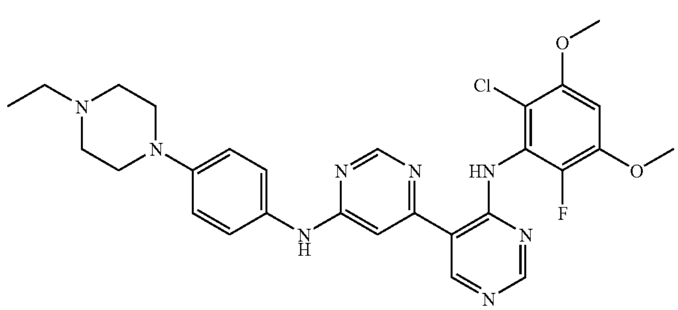 | ¹H NMR 400 MHz (CD₃OD) δ 8.77 (s, 1H), 8.60 (s, 1H), 8.51 (s, 1H), 8.48 (d, 2H), 7.12 (s, 1H), 6.96 (d, 2H), 6.80 (d, 1H), 3.85 (s, 3H), 3.84 (s, 3H), 3.82-3.69 (m, 2H), 3.66-3.53 (m, 2H), 3.37-3.08 (m, 4H), 3.07-2.89 (m, 2H), 1.31 (t, 3H); MS m/z 565.2 (M + 1). |

TABLE 1-continued

| Compound Number | Structure | Physical Data<br>¹H NMR 400 MHz<br>(DMSO-d₆) and/or MS (m/z) |
|---|---|---|
| 60 | 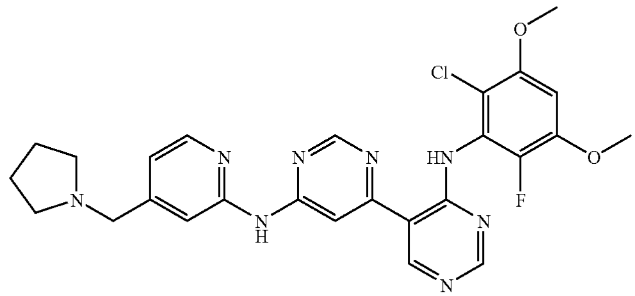 | ¹H NMR 400 MHz (CD₃OD) δ 8.93 (s, 1H), 8.83 (s, 1H), 8.58 (s, 1H), 8.42 (s, 1H), 8.33 (s, 1H), 7.85 (dd, 1H), 7.77 (d, 1H), 6.83 (d, 1H), 4.32 (s, 2H), 3.86 (s, 3H), 3.85 (s, 3H), 3.46 (bs, 2H), 3.14 (bs, 2H), 2.12 (bs, 2H), 1.94 (bs, 2H); MS m/z 537.1 (M + 1). |
| 61 | 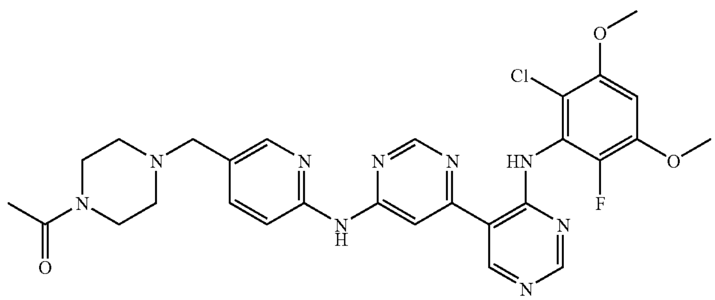 | ¹H NMR 400 MHz (CD₃OD) δ 8.95 (s, 1H), 8.90 (s, 1H), 8.58 (s, 1H), 8.38 (d, 1H), 8.04 (s, 1H), 7.84 (s, 1H), 7.20 (d, 1H), 6.83 (d, 1H), 4.15 (s, 2H), 3.87 (s, 3H), 3.85 (s, 3H) 3.69 (bs, 4H), 3.07 (bs, 2H), 3.00 (bs, 2H), 2.05 (s, 3H); MS m/z 594.2 (M + 1). |
| 62 | 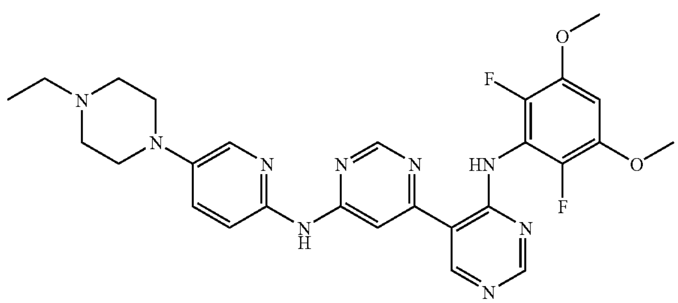 | MS m/z 550.2 (M + 1). |
| 63 | 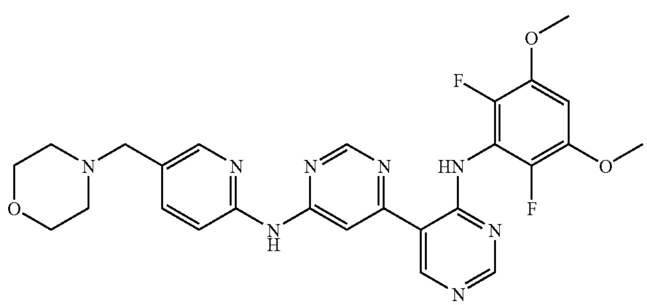 | MS m/z 537.2 (M + 1). |
| 64 | 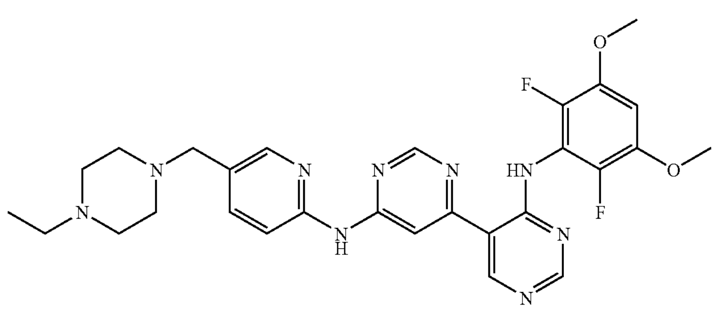 | MS m/z 564.2 (M + 1). |

TABLE 1-continued

| Compound Number | Structure | Physical Data ¹H NMR 400 MHz (DMSO-d$_6$) and/or MS (m/z) |
|---|---|---|
| 65 | 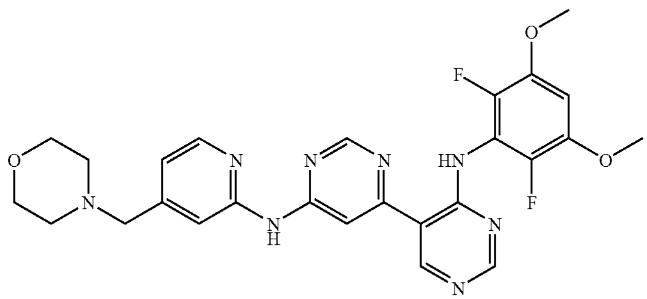 | MS m/z 537.2 (M + 1). |
| 66 | 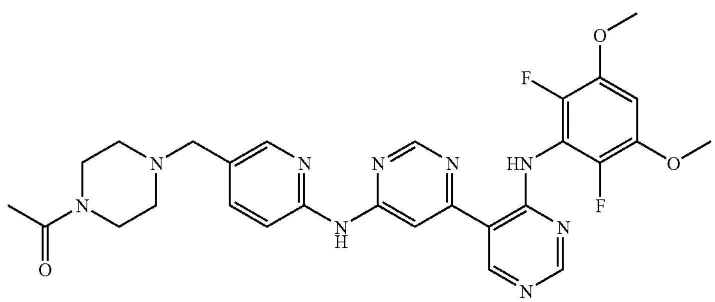 | MS m/z 578.2 (M + 1). |
| 67 | 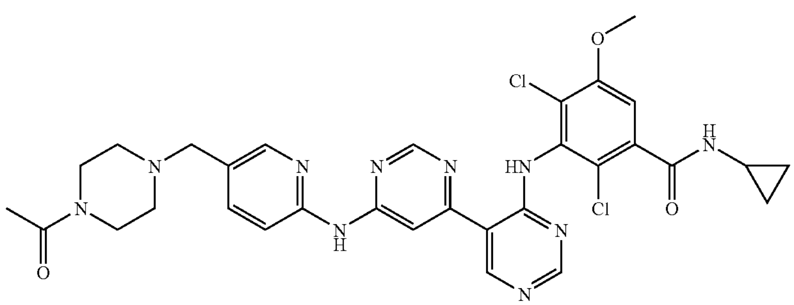 | MS m/z 663.2 (M + 1). |
| 68 | 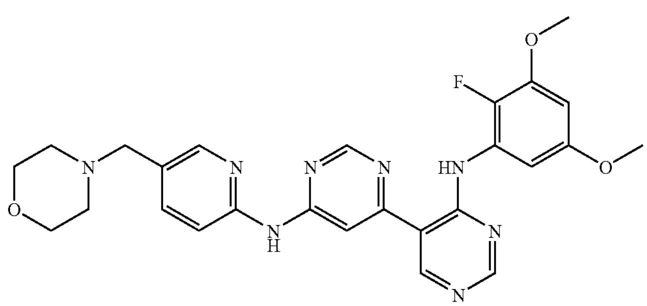 | MS m/z 519.2 (M + 1). |
| 69 | 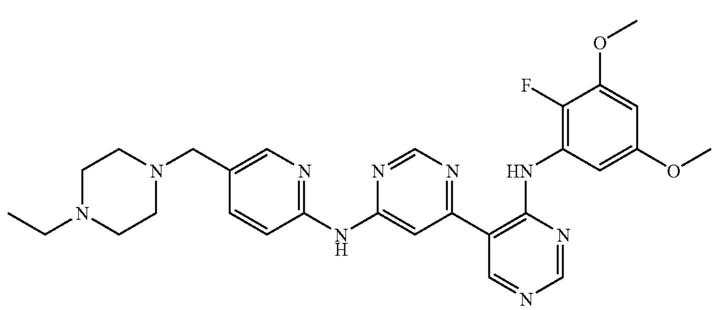 | MS m/z 546.2 (M + 1). |

TABLE 1-continued

| Compound Number | Structure | Physical Data ¹H NMR 400 MHz (DMSO-$d_6$) and/or MS (m/z) |
|---|---|---|
| 70 | 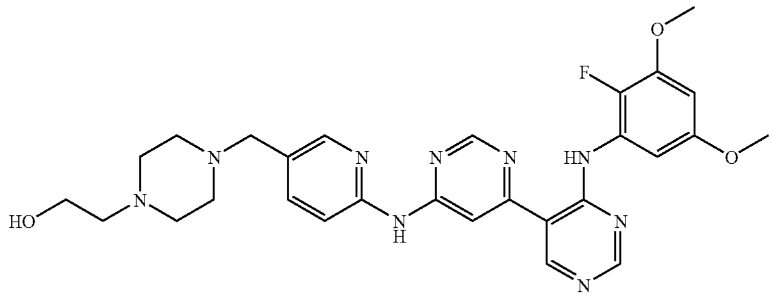 | MS m/z 562.2 (M + 1). |
| 71 | 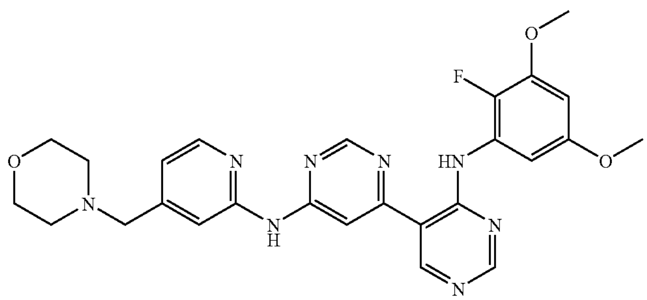 | MS m/z 519.2 (M + 1). |
| 72 | 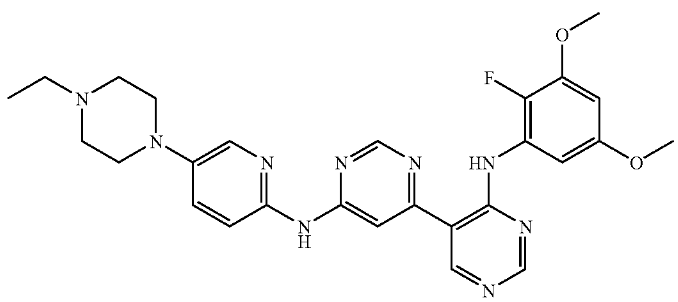 | MS m/z 532.2 (M + 1). |
| 73 | 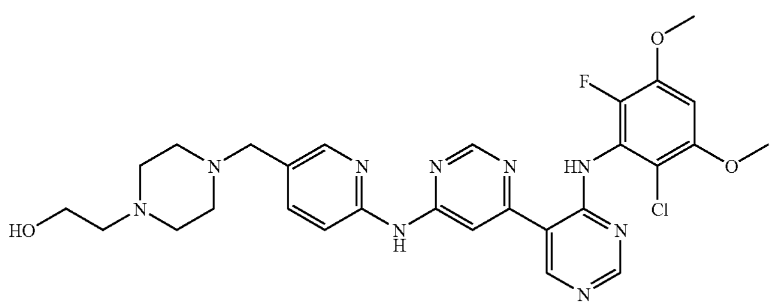 | MS m/z 596.2 (M + 1). |
| 74 | 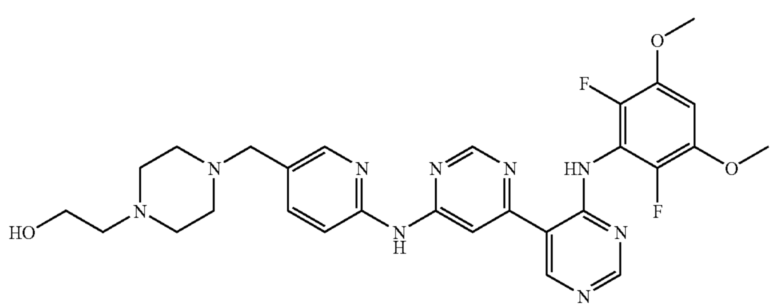 | MS m/z 580.2 (M + 1). |

TABLE 1-continued

| Compound Number | Structure | Physical Data <br> ¹H NMR 400 MHz (DMSO-d$_6$) and/or MS (m/z) |
|---|---|---|
| 75 | 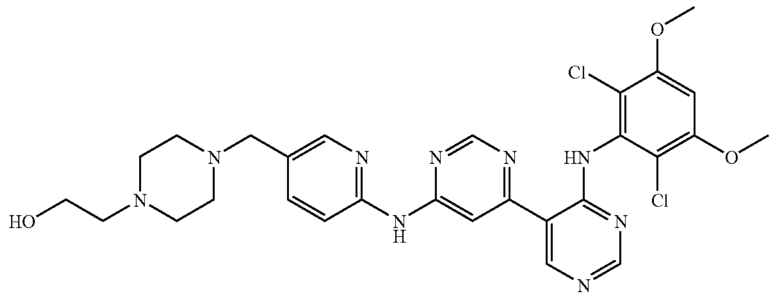 | MS m/z 612.2 (M + 1). |
| 76 | 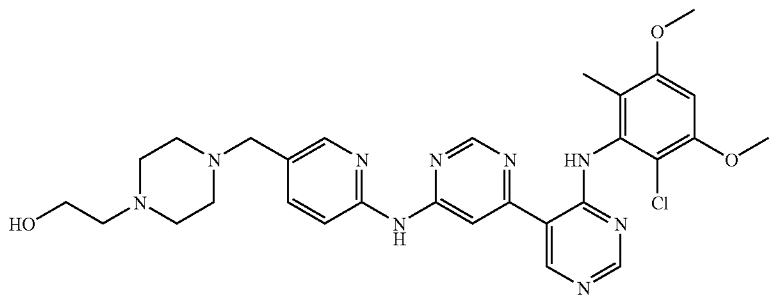 | MS m/z 592.2 (M + 1). |
| 77 | 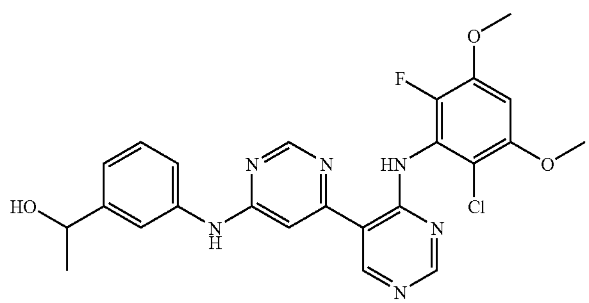 | MS m/z 496.1 (M + 1). |
| 78 | 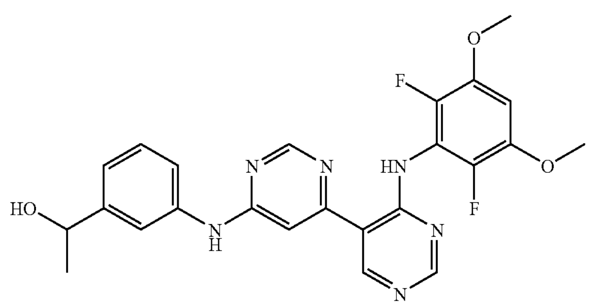 | MS m/z 481.1 (M + 1). |
| 79 | 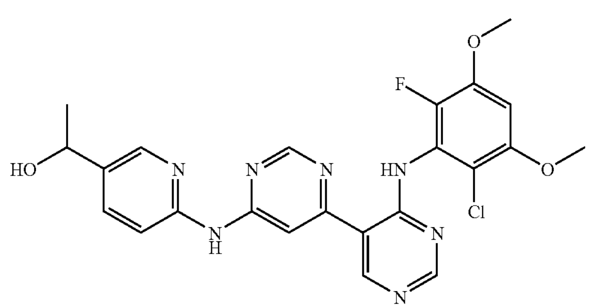 | MS m/z 498.1 (M + 1). |

TABLE 1-continued

| Compound Number | Structure | Physical Data ¹H NMR 400 MHz (DMSO-d₆) and/or MS (m/z) |
|---|---|---|
| 80 | 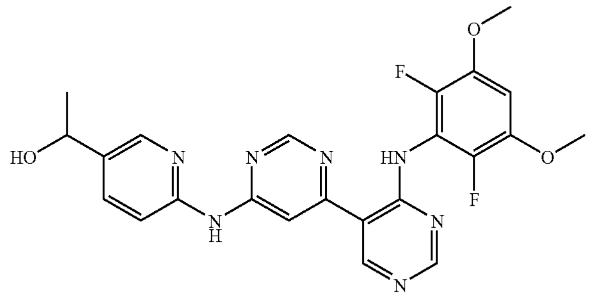 | MS m/z 482.1 (M + 1). |
| 81 | 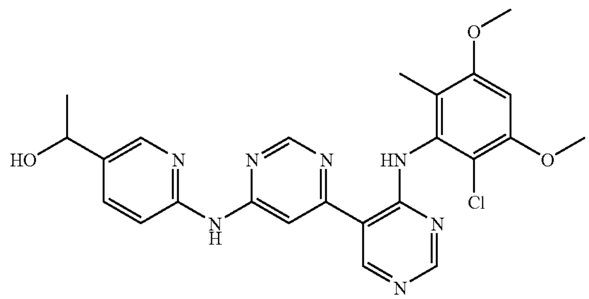 | MS m/z 494.1 (M + 1). |
| 82 | 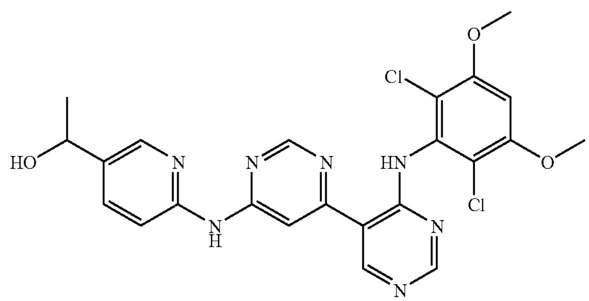 | MS m/z 514.1 (M + 1). |
| 83 | 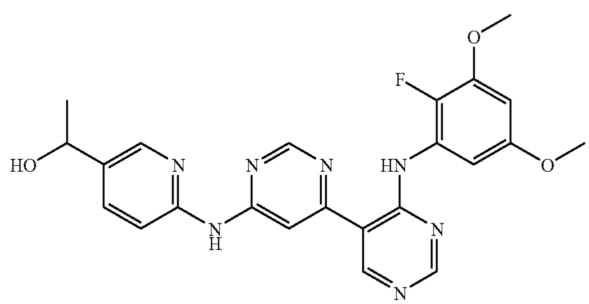 | MS m/z 464.1 (M + 1). |
| 84 | 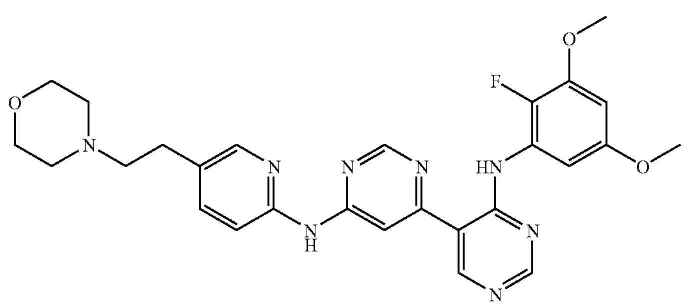 | MS m/z 533.2 (M + 1). |

TABLE 1-continued

| Compound Number | Structure | Physical Data<br>¹H NMR 400 MHz<br>(DMSO-d₆) and/or MS (m/z) |
|---|---|---|
| 85 | 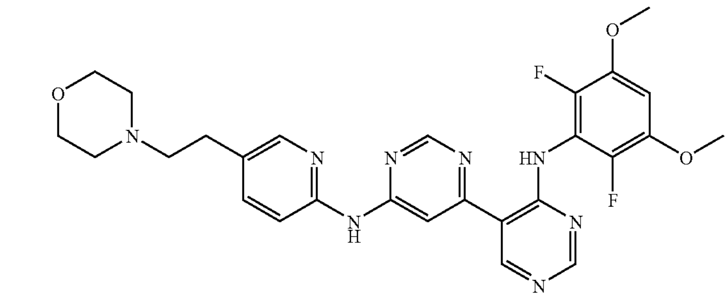 | MS m/z 551.2 (M + 1). |
| 86 | 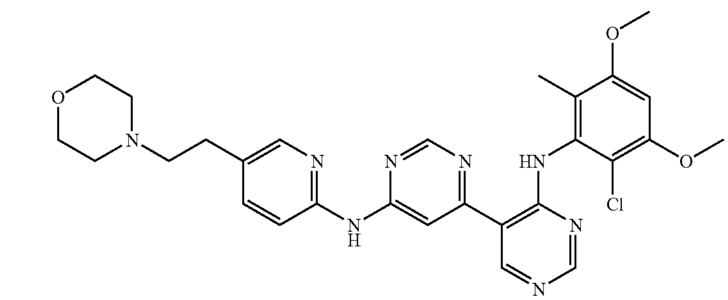 | MS m/z 563.2 (M + 1). |
| 87 | 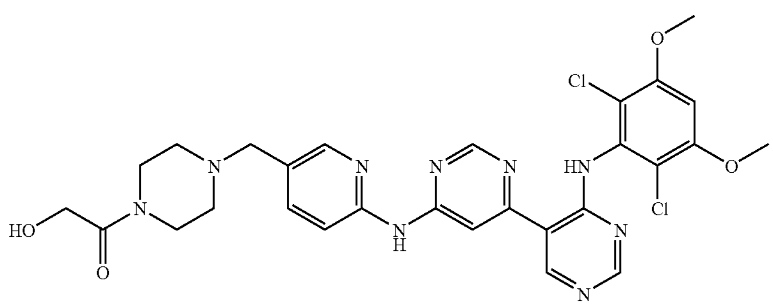 | MS m/z 626.2 (M + 1). |
| 88 | 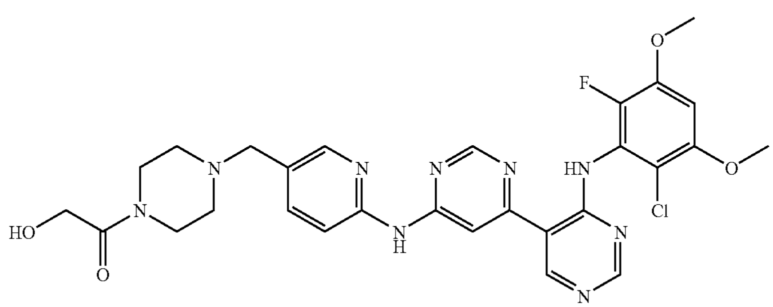 | MS m/z 610.2 (M + 1). |
| 89 | 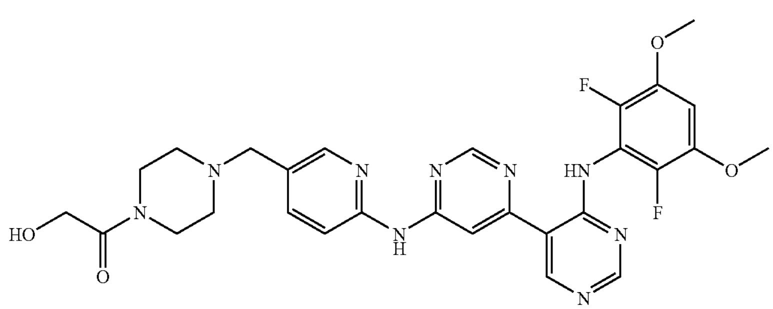 | MS m/z 594.2 (M + 1). |

TABLE 1-continued

| Compound Number | Structure | Physical Data<br>¹H NMR 400 MHz<br>(DMSO-d₆) and/or MS (m/z) |
|---|---|---|
| 90 | 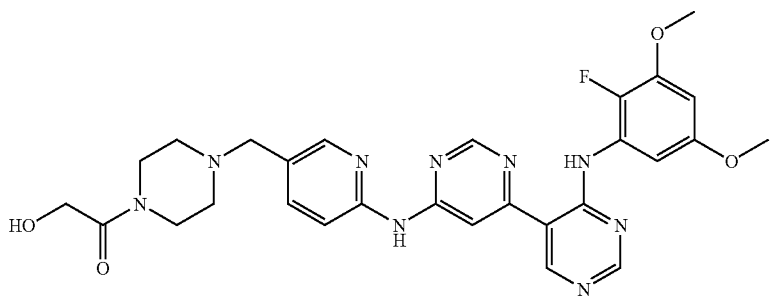 | MS m/z 576.2 (M + 1). |
| 91 | 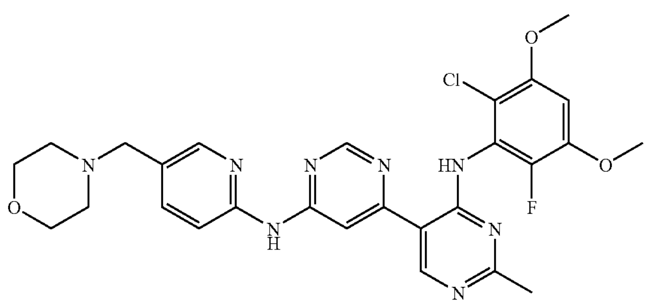 | MS m/z 567.2 (M + 1) |
| 92 | 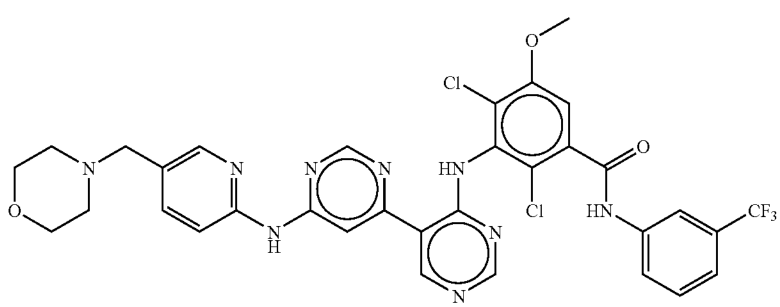 | MS m/z 726.1 (M + 1) |
| 93 | 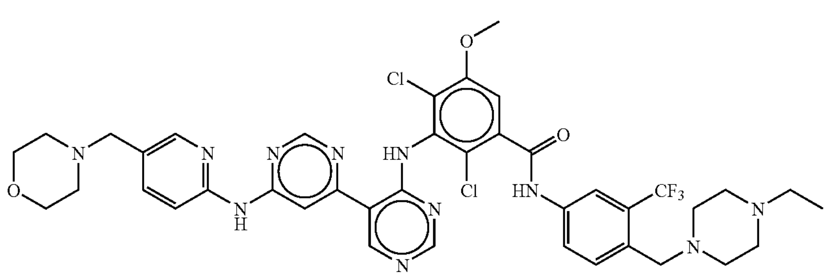 | MS m/z 852.3 (M + 1) |

Example 94

Synthesis of {6-[3-(2,6-Dichloro-3,5-dimethoxy-phenylamino)-pyrazin-2-yl]-pyrimidin-4-yl}-(5-morpholin-4-ylmethyl-pyridin-2-yl)-amine The synthesis is made as described in Scheme 7 and the subsequent description:

Scheme 7:

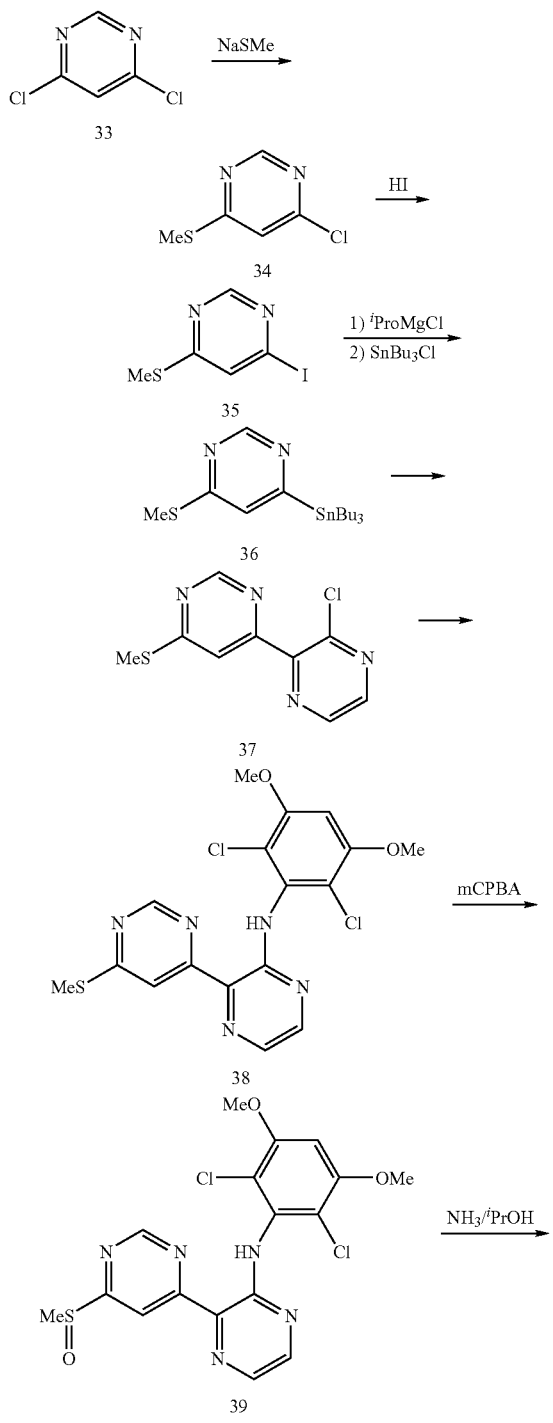

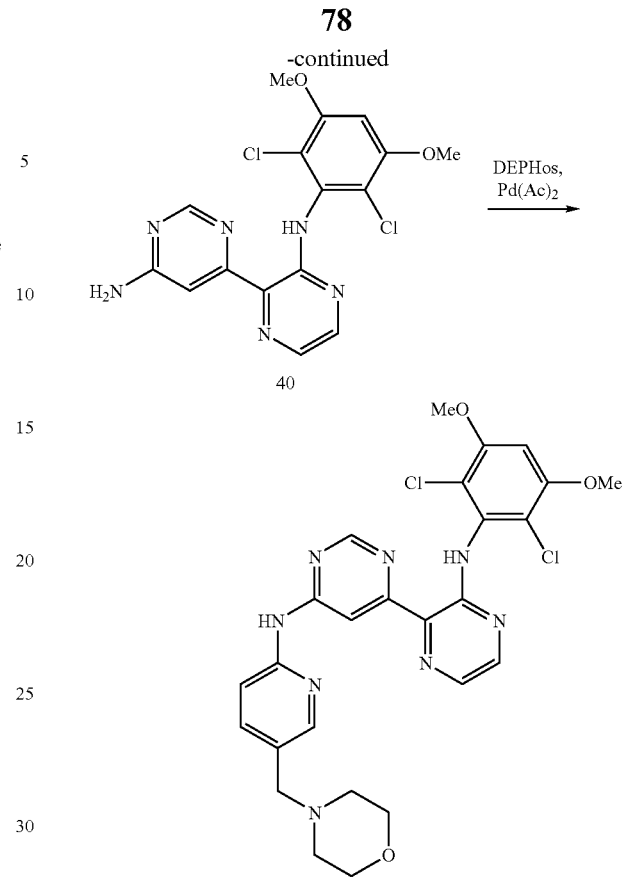

In the following detailed description, numbers of compounds correspond to those given in Scheme 7:

4-Chloro-6-methylsulfanyl-pyrimidine (34 in Scheme 7))

A mixture of 4,6-dichloro-pyrimidine 1 (20.93 g, 140 mmol) and sodium thiomethoxide (10.34 g, 147 mmol) in THF (100 mL) is stirred at room temperature. After reaction over-night, the reaction mixture is concentrated. The residue is partitioned between ethyl acetate and brine. The organic layer is separated and washed with brine, and dried over $Na_2SO_4$. The crude product is purified by recrystallization from hexanes (60 mL) to afford 4-chloro-6-methylsulfanyl-pyrimidine. The mother liquor is concentrated and the residue is purified by silica gel flash chromatography eluting with ethyl acetate in hexanes from 0% to 10% to afford 4-chloro-6-methylsulfanyl-pyrimidine containing small amount of byproduct 4,6-bis methylthio-pyrimidine, which can be easily removed in the next step. $^1$H NMR 400 MHz ($CDCl_3$) δ 8.72 (s, 1H), 7.21 (s, 1H), 2.58 (s, 3H).

4-Iodo-6-methylsulfanyl-pyrimidine (35)

A mixture of 4-chloro-6-methylsulfanyl-pyrimidine 34 (0.54 g, 3.36 mmol) and 57% hydriodic acid solution (2.50 mL, 18.95 mmol) in DCM (3 mL) is stirred at room temperature. After 5 h, the solid is collected by filtration and washed with DCM. The cake is dissolved in water (10 mL) and basified with saturated $NaHCO_3$ solution to pH=8. The aqueous layer is extracted with DCM (2×50 mL). The combined organic extracts are washed with brine, dried over $Na_2SO_4$, and concentrated to afford the desired product 4-iodo-6-methylsulfanyl-pyrimidine 35.

4-Methylsulfanyl-6-tributylstannanyl-pyrimidine (36)

A solution of $^i$PrMgCl (2M in THF solution, 5 mL, 10 mmol) is added slowly to a solution of 4-iodo-6-methylsulfanyl-pyrimidine 35 (2.53 g, 10 mol) in THF (50 mL) at −78° C. After 10 minutes, Bu$_3$SnCl (2.75 mL, 10 mmol) is added. After reaction overnight, the reaction mixture is concentrated. The crude product is purified by silica gel flash chromatography eluting with ethyl acetate in hexanes from 0% to 10% to afford 4-methylsulfanyl-6-tributylstannanyl-pyrimidine (36).

4-(3-Chloro-pyrazin-2-yl)-6-methylsulfanyl-pyrimidine (37)

A mixture of 4-methylsulfanyl-6-tributylstannanyl-pyrimidine (4) (1.80 g, 4.33 mmol), 2,3-dichloro-pyrazine (1.94 g, 13 mmol), PPh3 (0.907 g, 3.46 mmol) and palladium (II) acetate (194 mg, 0.866 mmol) in dioxane (15 mL) is degassed and sealed in a pressure tube. After stirring at 120° C. for 16 h, the reaction mixture is evaporated and purified by silica gel flash chromatography eluting with ethyl acetate in hexanes from 10% to 30% to afford the desired product 4-(3-chloro-pyrazin-2-yl)-6-methylsulfanyl-pyrimidine (37).

(2,6-Dichloro-3,5-dimethoxy-phenyl)-[3-(6-methylsulfanyl-pyrimidin-4-yl)-pyrazin-2-yl]-amine (38)

A suspension of 4-(3-chloro-pyrazin-2-yl)-6-methylsulfanyl-pyrimidine (37) (200 mg, 0.838 mmol), 2,6-dichloro-3,5-dimethoxyaniline (280 mg, 1.26 mmol), DPEphos (90 mg, 0.167 mmol), palladium (II) acetate (19 mg, 0.085 mmol) and cesium carbonate (546 mg, 1.68 mmol) in dioxane (8 mL) is degassed. After purging with Ar, the vial is sealed by the cap and irradiated at 150° C. for 30 minutes in Smith Synthesizer. The reaction mixture is evaporated and purified by silica gel flash chromatography eluting with ethyl acetate in hexanes from 10% to 30% to afford the desired product (2,6-dichloro-3,5-dimethoxy-phenyl)-[3-(6-methylsulfanyl-pyrimidin-4-yl)-pyrazin-2-yl]-amine (38).

(2,6-Dichloro-3,5-dimethoxy-phenyl)-[3-(6-methanesulfinyl-pyrimidin-4-yl)-pyrazin-2-yl]-amine (39)

To a suspension of (2,6-dichloro-3,5-dimethoxy-phenyl)-[3-(6-methylsulfanyl-pyrimidin-4-yl)-pyrazin-2-yl]-amine (6) (308 mg, 0.725 mmol) in CH$_2$Cl$_2$ (20 mL), mCPBA (250 mg, 1.02 mmol) is added portionwise during 3 min at 0° C. After stirring at 0° C. for 1.5 h, the reaction is then quenched with 5% Na$_2$S$_2$O$_3$ (10 mL) and saturated NaHCO$_3$ (5 mL). The aqueous phase is separated and extracted with EtOAc (2×40 mL). The organics are washed with brine (40 mL), dried over MgSO$_4$, and evaporated to give a yellow solid. This crude (39) is used for next reaction without further purification.

6-[3-(2,6-Dichloro-3,5-dimethoxy-phenylamino)-pyrazin-2-yl]-pyrimidin-4-ylamine (40)

(2,6-Dichloro-3,5-dimethoxy-phenyl)-[3-(6-methanesulfinyl-pyrimidin-4-yl)-pyrazin-2-yl]-amine 7 (200 mg, 0.414 mmol) is suspended in ammonia/2-propanol solution (2M, 3 mL, 6 mmol) in a sealed tube. After stirring at 100° C. overnight, the reaction is cooled to room temperature. The light yellow solid is collected by filtration, washed with water and 2-propanol, and dried to afford the desired product (6-[3-(2,6-dichloro-3,5-dimethoxy-phenylamino)-pyrazin-2-yl]-pyrimidin-4-ylamine (40). The filtrate can be used for further purification to give an additional product.

{6-[3-(2,6-Dichloro-3,5-dimethoxy-phenylamino)-pyrazin-2-yl]-pyrimidin-4-yl}-(5-morpholin-4-ylmethyl-pyridin-2-yl)-amine (41)

A suspension of (6-[3-(2,6-dichloro-3,5-dimethoxy-phenylamino)-pyrazin-2-yl]-pyrimidin-4-ylamine (41) (30 g, 0.076 mmol), 4-(6-bromo-pyridin-3-ylmethyl)-morpholine 12 (29 mg, 0.114 mmol), Xantphos (10 mg, 0.0178 mmol), palladium (II) acetate (2 mg, 0.0089 mmol) and cesium carbonate (50 mg, 0.152 mmol) in dioxane (1.5 mL) is degassed. After purging with Ar, the vial is sealed by the cap and irradiated at 150° C. for 20 minutes in Smith Synthesizer. The reaction mixture is treated with 4 ml of 5% diethyl dithiocabamyl acid sodium salt solution. The solid is collected by filtration and washed with water, then dried. The crude is purified by silica gel flash chromatography eluting with 1% NH$_3$ in CH$_3$OH/EtOAc from 0 to 10%) to afford the desired product {6-[3-(2,6-dichloro-3,5-dimethoxy-phenylamino)-pyrazin-2-yl]-pyrimidin-4-yl}-(5-morpholin-4-ylmethyl-pyridin-2-yl)-amine (41) (Example 94).

Specific intermediates useful in the synthesis of compounds of the formula I can be prepared as follows:

Starting material c (Scheme 8):

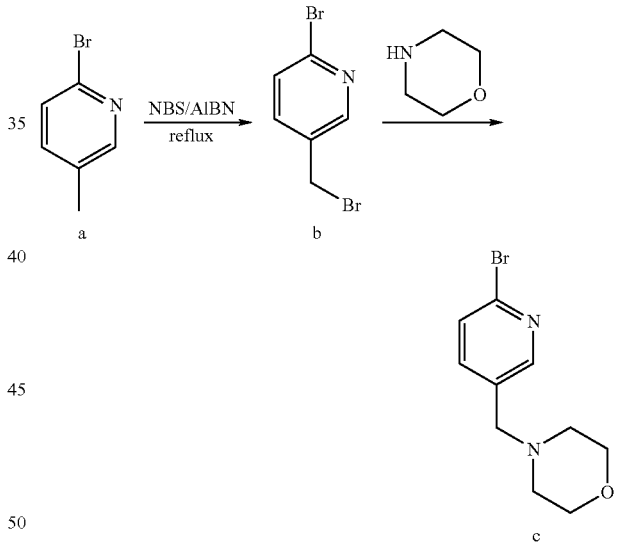

4-(6-Bromo-pyridin-3-ylmethyl)-morpholine (c)

To a suspension of 2-bromo-5-methyl-pyridine a (5.00 g, 29 mmol) and NBS (5.162 g, 29 mmol) in CCl$_4$ (40 mL), AIBN (0.477 g, 2.9 mmol) is added. The reaction is stirred at 75° C. for 5 h. and filtered. The filter cake is washed with CCl$_4$, and the filtrate is evaporated to give a light yellow residue.

The crude is dissolved in anhydrous THF (40 mL). DIEA (5.03 mL, 29 mmol) is added, followed by addition of morpholine (3.0 mL, 34.3 mmol). After stirring at rt for 1 h, the reaction is partitioned between saturated NaHCO$_3$ (30 mL) and EtOAc (100 mL), and separated. The obtained EtOAc extract is washed with brine (30 mL), dried and evaporated.

The crude is purified by flash column chromatography (SiO$_2$, 1% NH$_3$ in CH$_3$OH/CH$_2$Cl$_2$ from 0 to 10%) to give (c) as a light tan colored solid: $^1$H NMR 400 MHz (DMSO-d$_6$) δ 8.31 (d, J=2.4 Hz, 1H), 7.69 (dd, J=2.4, 8.4 Hz, 1H), 7.62 (d, J=8.0 Hz, 1H), 3.57 (t, J=4.8 Hz, 4H), 3.48 (s, 2H), 2.35 (t, J=4.4 Hz, 4H); MS m/z 257.1 (M+1).

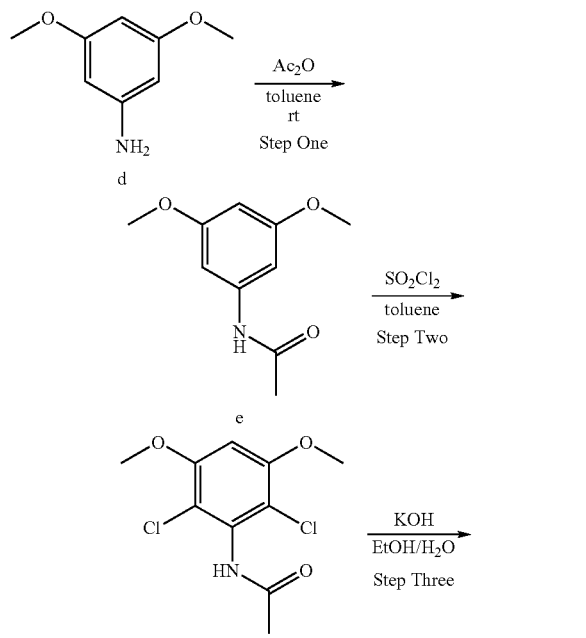

N-(3,5-Dimethoxy-phenyl)-acetamide (e)

To a solution of 3,5-dimethoxy-phenylamine (d) (22.0 g, 143.6 mmol) in toluene (100 mL), Ac$_2$O (14 mL) is added slowly at room temperature. After stirring 30 min, hexane (50 mL) is added with stirring at rt. The resulting solid is filtered and washed with hexane (50 mL) to offer the title product e as a white solid.

N-(2,6-Dichloro-3,5-dimethoxy-phenyl)-acetamide (f)

To a suspension of N-(3,5-dimethoxy-phenyl)-acetamide (e) (10.0 g, 51.22 mmol) in MeCN (150 mL), cooled at 0° C., sulfuryl chloride (8.23 mL, 101.53 mmol) is added slowly. After stirring for half hour, the solution is warmed to rt and stirred overnight. After the solvent (MeCN) is removed under vacuum, NaHCO$_3$ (Sat., 200 mL) and ethyl acetate (250 mL) are added and stirred for half an hour. The white solid is obtained by filtration of the resulting mixture, washed with water and dried to give the title product f: hexane/ethyl acetate, 1:1): MS m/z 264.00 (M+1). The rest of three by-products stays in solution phase.

2,6-Dichloro-3,5-dimethoxy-phenylamine (g)

To a suspension of N-(2,6-dichloro-3,5-dimethoxy-phenyl)-acetamide (f) (6.50 g, 24.61 mmol) in a mixture of EtOH (80 mL) and water (30 mL), KOH (20 g) is added, and the mixture is stirred 2 days at 80° C. After the solvent (EtOH) is removed under vacuum, water (~15 mL) is added, and a white solid is collected by filtration and washed with water and dried to give final product g: $^1$H NMR 600 MHz (CDCl$_3$) δ 6.03 (s, 1H), 4.55 (s, 2H), 3.88 (s, 6H); MS m/z 222.00 (M+1).

The following products can be obtained in analogy to example 94:

TABLE 2

| Compound (Example) Number | Structure | Physical Data $^1$H NMR 400 MHz (DMSO-d$_6$) and/or MS (m/z) |
| --- | --- | --- |
| 94 | 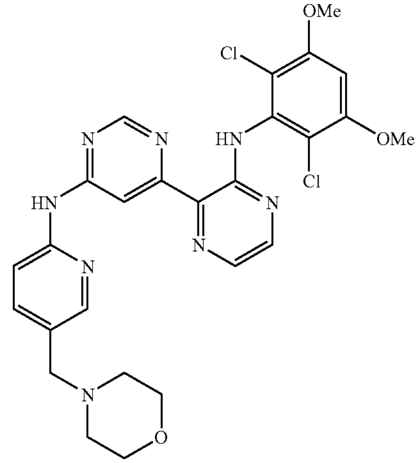 | MS m/z 569.2 (M + 1). |

TABLE 2-continued
| Compound (Example) Number | Structure | Physical Data $^1$H NMR 400 MHz (DMSO-$d_6$) and/or MS (m/z) |
|---|---|---|
| 95 | 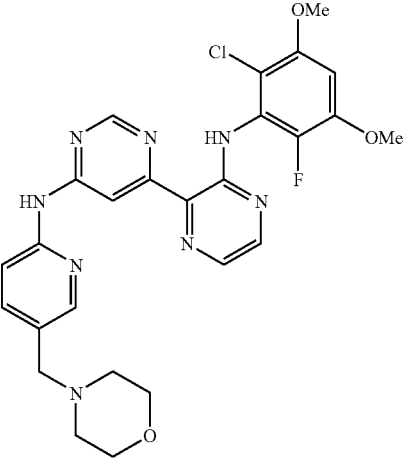 | MS m/z 553.2 (M + 1). |
| 96 | 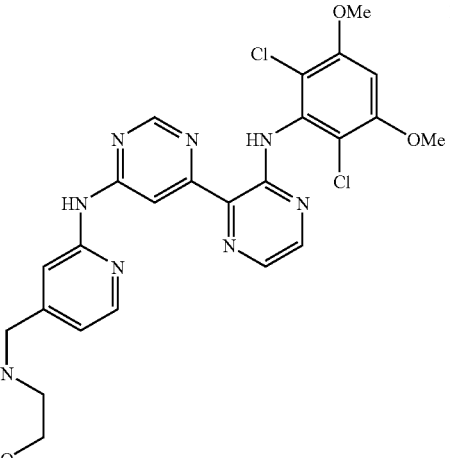 | MS m/z 569.2 (M + 1). |
| 97 | 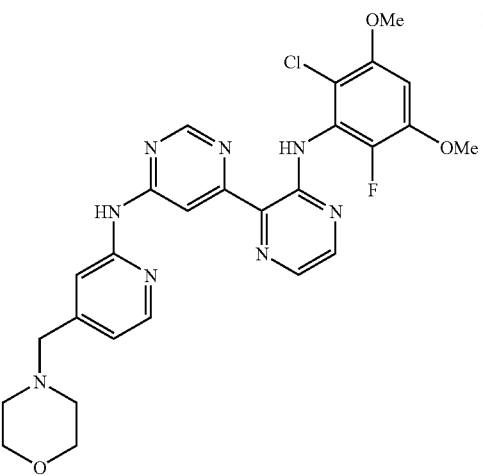 | MS m/z 553.2 (M + 1). |

TABLE 2-continued

| Compound (Example) Number | Structure | Physical Data $^1$H NMR 400 MHz (DMSO-$d_6$) and/or MS (m/z) |
|---|---|---|
| 98 | 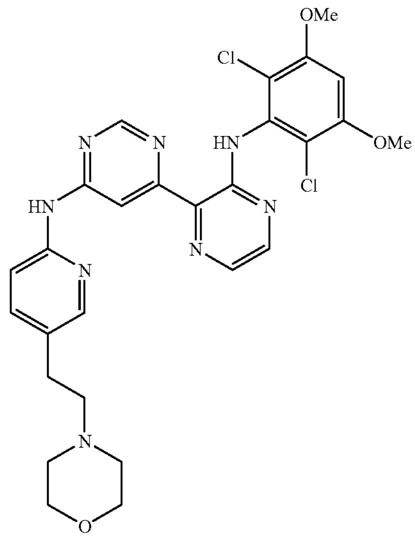 | MS m/z 583.2 (M + 1). |
| 99 | 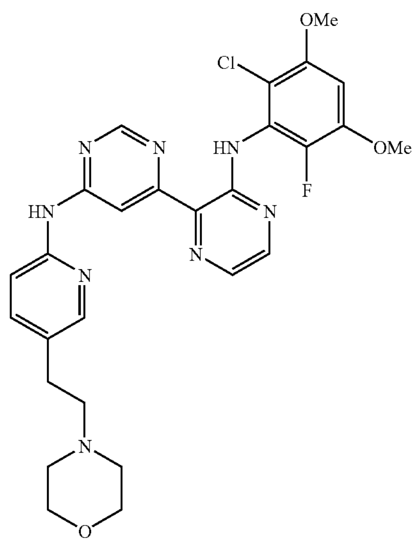 | MS m/z 567.2 (M + 1). |
| 100 | 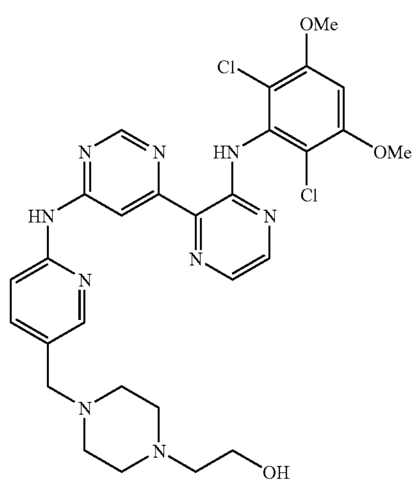 | MS m/z 612.2 (M + 1). |

TABLE 2-continued

| Compound (Example) Number | Structure | Physical Data ¹H NMR 400 MHz (DMSO-$d_6$) and/or MS (m/z) |
|---|---|---|
| 101 | 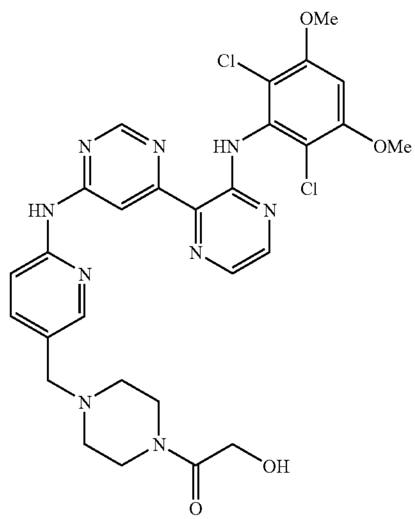 | MS m/z 626.2 (M + 1). |
| 102 | 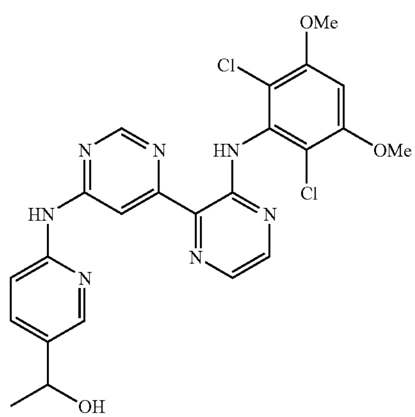 | MS m/z 514.1 (M + 1). |
| 103 | 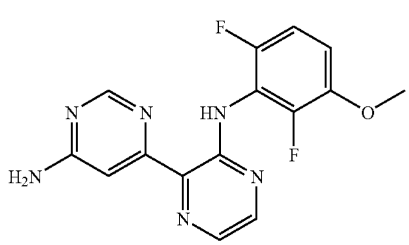 | MS m/z 331.1 (M + 1). |

TABLE 2-continued

| Compound (Example) Number | Structure | Physical Data ¹H NMR 400 MHz (DMSO-d₆) and/or MS (m/z) |
|---|---|---|
| 104 | 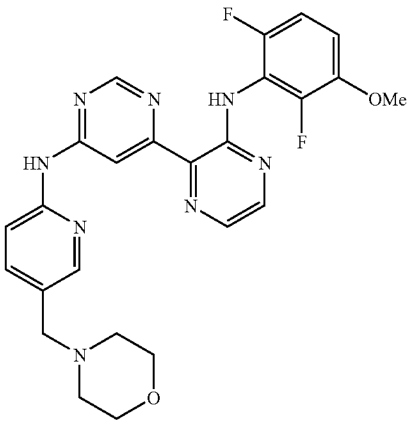 | MS m/z 507.2 (M + 1). |
| 105 | 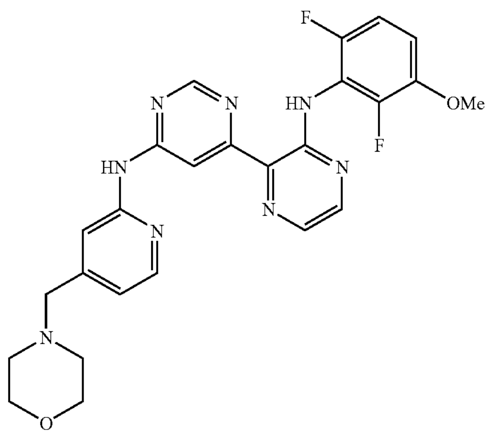 | MS m/z 507.2 (M + 1). |
| 106 | 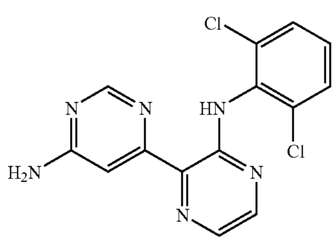 | MS m/z 333.18 (M + 1). |
| 107 | 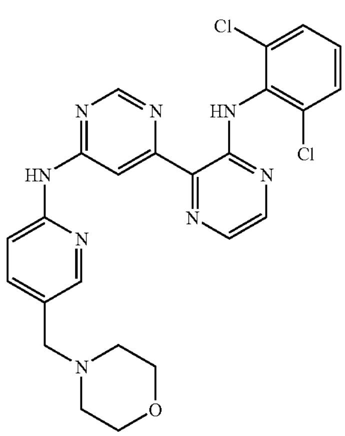 | MS m/z 509.39 (M + 1). |

TABLE 2-continued

| Compound (Example) Number | Structure | Physical Data $^1$H NMR 400 MHz (DMSO-$d_6$) and/or MS (m/z) |
|---|---|---|
| 108 | 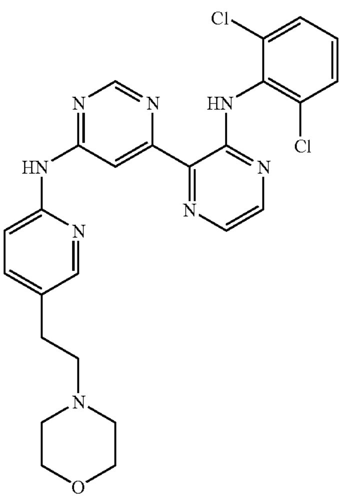 | MS m/z 523.2 (M + 1). |
| 109 | 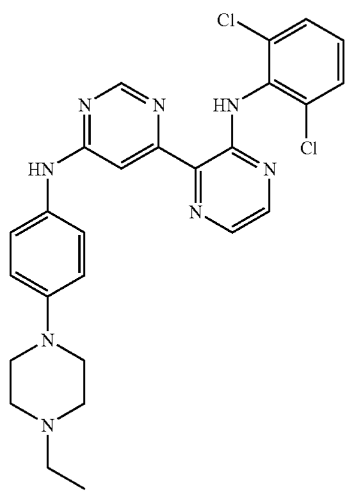 | MS m/z 521.2 (M + 1). |
| 110 | 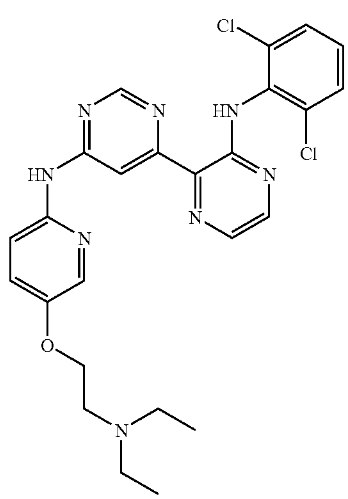 | MS m/z 524.2 (M + 1). |

Assays

Compounds of the present invention are assayed to measure their capacity to selectively inhibit the proliferation of FGFR3 dependent Ba/F3 cells. In addition, compounds are assayed to measure their capacity to inhibit a panel of kinases.

FGFR3 (Enzymatic Assay)

Kinase activity assay with purified FGFR3 (Upstate) is carried out in a final volume of 10 μL containing 0.25 μg/mL of enzyme in kinase buffer (30 mM Tris-HCl pH7.5, 15 mM $MgCl_2$, 4.5 mM $MnCl_2$, 15 μM $Na_3VO_4$ and 50 μg/mL BSA), and substrates (5 μg/mL biotin-poly-EY (Glu, Tyr) (CIS-US, Inc.) and 3 μM ATP). Two solutions are made: the first solution of 5 μl contains the FGFR3 enzyme in kinase buffer was first dispensed into 384-format ProxiPlate® (Perkin-Elmer) followed by adding 50 nL of compounds dissolved in DMSO, then 5 μl of second solution contains the substrate (poly-EY) and ATP in kinase buffer was added to each wells. The reactions are incubated at room temperature for one hour, stopped by adding 10 μL of HTRF detection mixture, which contains 30 mM Tris-HCl pH7.5, 0.5 M KF, 50 mM ETDA, 0.2 mg/mL BSA, 15 μg/mL streptavidin-XL665 (CIS-US, Inc.) and 150 ng/mL cryptate conjugated anti-phosphotyrosine antibody (CIS-US, Inc.). After one hour of room temperature incubation to allow for streptavidin-biotin interaction, time resolved florescent signals are read on Analyst GT (Molecular Devices Corp.). $IC_{50}$ values are calculated by linear regression analysis of the percentage inhibition of each compound at 12 concentrations (1:3 dilution from 50 μM to 0.28 nM). In this assay, compounds of the invention have an $IC_{50}$ in the range of 10 nM to 2 μM.

FGFR3 (Cellular Assay)

Compounds of the invention are tested for their ability to inhibit transformed Ba/F3-TEL-FGFR3 cells proliferation, which is dependent on FGFR3 cellular kinase activity. Ba/F3-TEL-FGFR3 are cultured up to 800,000 cells/mL in suspension, with RPMI 1640 supplemented with 10% fetal bovine serum as the culture medium. Cells are dispensed into 384-well format plate at 5000 cell/well in 50 μA, culture medium. Compounds of the invention are dissolved and diluted in dimethylsulfoxide (DMSO). Twelve points 1:3 serial dilutions are made into DMSO to create concentrations gradient ranging typically from 10 mM to 0.05 μM. Cells are added with 50 nL of diluted compounds and incubated for 48 hours in cell culture incubator. AlamarBlue® (TREK Diagnostic Systems), which can be used to monitor the reducing environment created by proliferating cells, are added to cells at final concentration of 10%. After additional four hours of incubation in a 37° C. cell culture incubator, fluorescence signals from reduced AlamarBlue® (Excitation at 530 nm, Emission at 580 nm) are quantified on Analyst GT (Molecular Devices Corp.). $IC_{50}$ values are calculated by linear regression analysis of the percentage inhibition of each compound at 12 concentrations.

B-Raf (Enzymatic assay)

Compounds of the invention may be tested for their ability to inhibit the activity of b-Raf. The assay is carried out in 384-well MaxiSorp plates (NUNC) with black walls and clear bottom. The substrate, IκBα is diluted in DPBS (1:750) and 15 μl is added to each well. The plates are incubated at 4° C. overnight and washed 3 times with TBST (25 mM Tris, pH 8.0, 150 mM NaCl and 0.05% Tween-20) using the EMBLA plate washer. Plates are blocked by Superblock (15 μl/well) for 3 hours at room temperature, washed 3 times with TBST and pat-dried. Assay buffer containing 20 μM ATP (10 μl) is added to each well followed by 100 nl or 500 nl of compound. B-Raf is diluted in the assay buffer (1 μl into 25 μl) and 10 μl of diluted b-Raf is added to each well (0.4 μg/well). The plates are incubated at room temperature for 2.5 hours. The kinase reaction is stopped by washing the plates 6 times with TBST. Phosph-IκBα (Ser32/36) antibody is diluted in Superblock (1:10,000) and 15 μl is added to each well. The plates are incubated at 4° C. overnight and washed 6 times with TBST. AP-conjugated goat-anti-mouse IgG is diluted in Superblock (1:1,500) and 15 μl is added to each well. Plates are incubated at room temperature for 1 hour and washed 6 times with TBST. 15 μl of fluorescent Attophos AP substrate (Promega) is added to each well and plates are incubated at room temperature for 15 minutes. Plates are read on Acquest or Analyst GT using a Fluorescence Intensity Program (Excitation 455 nm, Emission 580 nm).

B-Raf (Cellular Assay)

Compounds of the invention are tested in A375 cells for their ability to inhibit phosphorylation of MEK. A375 cell line (ATCC) is derived from a human melanoma patient and has a V599E mutation on the B-Raf gene. The levels of phosphorylated MEK are elevated due to the mutation of B-Raf. Sub-confluent to confluent A375 cells are incubated with compounds for 2 hours at 37° C. in serum free medium. Cells are then washed once with cold PBS and lysed with the lysis buffer containing 1% Triton X100. After centrifugation, the supernatants are subjected to SDS-PAGE, and then transferred to nitrocellulose membranes. The membranes are then subjected to western blotting with anti-phospho-MEK antibody (ser217/221) (Cell Signaling). The amount of phosphorylated MEK is monitored by the density of phospho-MEK bands on the nitrocellulose membranes.

Inhibition of Cellular Bcr-Abl Dependent Proliferation (High Throughput Method)

The murine cell line 32D hemopoietic progenitor cell line may be transformed with Bcr-Abl cDNA (32D-p210). These cells are maintained in RPMI/10% fetal calf serum (RPMI/FCS) supplemented with penicillin 50 μg/mL, streptomycin 50 μg/mL and L-glutamine 200 mM. Untransformed 32D cells are similarly maintained with the addition of 15% of WEHI conditioned medium as a source of IL3.

50 μl of a 32D or 32D-p210 cells suspension are plated in Greiner 384 well microplates (black) at a density of 5000 cells per well. 50 nl of test compound (1 mM in DMSO stock solution) is added to each well (STI571 is included as a positive control). The cells are incubated for 72 hours at 37° C., 5% $CO_2$. 10 μl of a 60% Alamar Blue solution (Tek diagnostics) is added to each well and the cells are incubated for an additional 24 hours. The fluorescence intensity (Excitation at 530 nm, Emission at 580 nm) is quantified using the Acquest™ system (Molecular Devices).

Inhibition of Cellular Bcr-Abl Dependent Proliferation 32D-p210 cells are plated into 96 well TC plates at a density of 15,000 cells per well. 50 μL of two fold serial dilutions of the test compound ($C_{max}$ is 40 μM) are added to each well (STI571 is included as a positive control). After incubating the cells for 48 hours at 37° C., 5% $CO_2$, 15 μL of MTT (Promega) is added to each well and the cells are incubated for an additional 5 hours. The optical density at 570 nm is quantified spectrophotometrically and $IC_{50}$ values, the concentration of compound required for 50% inhibition, determined from a dose response curve.

Effect on Cell Cycle Distribution 32D and 32D-p210 cells are plated into 6 well TC plates at $2.5 \times 10^6$ cells per well in 5 ml of medium and test compound at 1 or 10 μM is added (STI571 is included as a control). The cells are then incubated for 24 or 48 hours at 37° C., 5% $CO_2$. 2 ml of cell suspension is washed with PBS, fixed in 70% EtOH for 1 hour and treated with PBS/EDTA/RNase A for 30 minutes. Propidium iodide (Cf=10 µg/ml) is added and the fluorescence intensity is quantified by flow cytometry on the FACScalibur™ system (BD Biosciences). In some embodiments, test compounds of the present invention may demonstrate an apoptotic effect on the 32D-p210 cells but not induce apoptosis in the 32D parental cells.

Effect on Cellular Bcr-Abl Autophosphorylation

Bcr-Abl autophosphorylation is quantified with capture Elisa using a c-Abl specific capture antibody and an antiphosphotyrosine antibody. 32D-p210 cells are plated in 96 well TC plates at $2\times10^5$ cells per well in 50 µL of medium. 50 µL of two fold serial dilutions of test compounds ($C_{max}$ is 10 µM) are added to each well (STI571 is included as a positive control). The cells are incubated for 90 minutes at 37° C., 5% $CO_2$. The cells are then treated for 1 hour on ice with 150 µL of lysis buffer (50 mM Tris-HCl, pH 7.4, 150 mM NaCl, 5 mM EDTA, 1 mM EGTA and 1% NP-40) containing protease and phosphatase inhibitors. 50 µL of cell lysate is added to 96 well optiplates previously coated with anti-Abl specific antibody and blocked. The plates are incubated for 4 hours at 4° C. After washing with TBS-Tween 20 buffer, 50 µL of alkaline-phosphatase conjugated anti-phosphotyrosine antibody is added and the plate is further incubated overnight at 4° C. After washing with TBS-Tween 20 buffer, 90 µL of a luminescent substrate are added and the luminescence is quantified using the Acquest™ system (Molecular Devices). In some embodiments, test compounds of the invention may inhibit the proliferation of the Bcr-Abl expressing cells, inhibiting the cellular Bcr-Abl autophosphorylation in a dose-dependent manner.

Effect on Proliferation of Cells Expressing Mutant Forms of Bcr-Abl

Compounds of the invention may be tested for their antiproliferative effect on Ba/F3 cells expressing either wild type or the mutant forms of Bcr-Abl (G250E, E255V, T315I, F317L, M351T) that confers resistance or diminished sensitivity to STI571. The antiproliferative effect of these compounds on the mutant-Bcr-Abl expressing cells and on the non transformed cells may be tested at 10, 3.3, 1.1 and 0.37 µM as described above (in media lacking IL3). The $IC_{50}$ values of the compounds lacking toxicity on the untransformed cells are determined from the dose response curves obtained as described above.

FLT3 and PDGFRβ

The effects of compounds of the invention on the cellular activity of FLT3 and PDGFRβ may be conducted following identical methods as described above for FGFR3 cellular activity, using Ba/F3-FLT3-ITD and Ba/F3-Tel-PDGFRβ.

Compounds of the invention may be tested for their ability to inhibit transformed Ba/F3-FLT3-ITD or Ba/F3-Tel-PDGFRβ cells proliferation, which is dependent on FLT3 or PDGFRβ cellular kinase activity. Ba/F3-FLT3-ITD or Ba/F3-Tel-PDGFRβ are cultured up to 800,000 cells/mL in suspension, with RPMI 1640 supplemented with 10% fetal bovine serum as the culture medium. Cells are dispensed into 384-well format plate at 5000 cell/well in 50 µL culture medium. Compounds of the invention are dissolved and diluted in dimethylsulfoxide (DMSO). Twelve points 1:3 serial dilutions are made into DMSO to create concentrations gradient ranging typically from 10 mM to 0.05 µM. Cells are added with 50 mL of diluted compounds and incubated for 48 hours in cell culture incubator. AlamarBlue® (TREK Diagnostic Systems), which can be used to monitor the reducing environment created by proliferating cells, are added to cells at final concentration of 10%. After additional four hours of incubation in a 37° C. cell culture incubator, fluorescence signals from reduced AlamarBlue® (Excitation at 530 nm, Emission at 580 nm) are quantified on Analyst GT (Molecular Devices Corp.). $IC_{50}$ values are calculated by linear regression analysis of the percentage inhibition of each compound at 12 concentrations.

FLT3, PDGFRβ, KDR, ALK, EphA/B, InsR, JAK2, c-Kit, Lck, Lyn, c-Met, Ret, Ron, Ros, Src, Syk, Tie-2, TrkB, TYK2 and Zap-70 (Cellular Assay)

The effects of compounds of the invention on the cellular activity of FLT3, PDGFRβ, KDR, ALK, EphA/B, InsR, JAK2, c-Kit, Lck, Lyn, c-Met, Ret, Ron, Ros, Src, Syk, Tie-2, TrkB, TYK2 and Zap-70 are conducted using identical methods as described above for FGFR3 cellular activity, except that instead of using Ba/F3-TEL-FGFR3, Ba/F3-TEL-FLT3, Ba/F3-TEL-PDGFRβ, Ba/F3-TEL-KDR, Ba/F3-TEL-ALK, Ba/F3-TEL-EphA/B, Ba/F3-TEL-InsR, Ba/F3-TEL-JAK2, Ba/F3-TEL-c-Kit, Ba/F3-TEL-Lck, Ba/F3-TEL-Lyn, Ba/F3-TEL-c-Met, Ba/F3-TEL-Ret, Ba/F3-TEL-Ron, Ba/F3-TEL-Ros, Ba/F3-TEL-Src, Ba/F3-TEL-Syk, Ba/F3-TEL-Tie-2, Ba/F3-TEL-TrkB, Ba/F3-TEL-TYK2 and Ba/F3-TEL-Zap-70 are used, respectively.

Upstate KinaseProfiler™—Radio-enzymatic Filter Binding Assay

Compounds of the invention are assessed for their ability to inhibit individual members of the kinase panel. The compounds are tested in duplicates at a final concentration of 10 µM following this generic protocol. Note that the kinase buffer composition and the substrates vary for the different kinases included in the "Upstate KinaseProfiler™" panel. Kinase buffer (2.5 µL, 10×—containing $MnCl_2$ when required), active kinase (0.001-0.01 Units; 2.54), specific or Poly(Glu4-Tyr) peptide (5-500 µM or 0.01 mg/ml) in kinase buffer and kinase buffer (50 µM; 5 µL) are mixed in an eppendorf on ice. A Mg/ATP mix (10 µL; 67.5 (or 33.75) mM $MgCl_2$, 450 (or 225) µM ATP and 1 µCi/µl [$\gamma$-$^{32}$P]-ATP (3000 Ci/mmol)) is added and the reaction is incubated at about 30° C. for about 10 minutes. The reaction mixture is spotted (20 µL) onto a 2 cm×2 cm P81 (phosphocellulose, for positively charged peptide substrates) or Whatman No. 1 (for Poly (Glu4-Tyr) peptide substrate) paper square. The assay squares are washed 4 times, for 5 minutes each, with 0.75% phosphoric acid and washed once with acetone for 5 minutes. The assay squares are transferred to a scintillation vial, 5 ml scintillation cocktail are added and $^{32}$P incorporation (cpm) to the peptide substrate is quantified with a Beckman scintillation counter. Percentage inhibition is calculated for each reaction.

Compounds of Formula I, in free form or in pharmaceutically acceptable salt form, exhibit valuable pharmacological properties, for example, as indicated by the in vitro tests described in this application. Compounds of Formula I are selective for FGFR3 (for example, each compound is 10 to >1000 fold selective for FGFR3 over KDR) and preferably show an $IC_{50}$ in the range of 500 nM or less, preferably, less than 400 nM, 300 nM, 200 nM, 100 nM and 50 nM in the FGFR3 cellular assay.

For example, Table 3 details the activity of the compounds of table 1 in the FGFR3 cellular assay where "*", "" and "*" indicates an activity of 250-500 nM, 100-250 nM and <0-100 nM, respectively:

TABLE 3

| Compound Number | FGFR3 Cellular (nM) |
|---|---|
| 1 | ** |
| 2 | *** |

TABLE 3-continued

| Compound Number | FGFR3 Cellular (nM) |
|---|---|
| 3 | *** |
| 4 | *** |
| 5 | *** |
| 6 | *** |
| 7 | *** |
| 8 | ** |
| 9 | *** |
| 10 | *** |
| 11 | *** |
| 12 | ** |
| 13 | * |
| 14 | * |
| 15 | *** |
| 16 | *** |
| 17 | *** |
| 18 | *** |
| 19 | *** |
| 20 | *** |
| 21 | * |
| 22 | *** |
| 23 | * |
| 24 | *** |
| 25 | *** |
| 26 | * |
| 27 | *** |
| 28 | *** |
| 29 | *** |
| 30 | *** |
| 31 | *** |
| 32 | ** |
| 33 | *** |
| 34 | * |
| 35 | *** |
| 36 | *** |
| 37 | ** |
| 38 | ** |
| 39 | ** |
| 40 | *** |
| 41 | *** |
| 42 | *** |
| 43 | *** |
| 44 | *** |
| 45 | *** |
| 46 | *** |
| 47 | *** |
| 48 | *** |
| 49 | *** |
| 50 | *** |
| 51 | *** |
| 52 | *** |
| 53 | *** |
| 54 | *** |
| 55 | *** |
| 56 | *** |
| 57 | *** |
| 58 | *** |
| 59 | *** |
| 60 | *** |
| 61 | *** |
| 62 | *** |
| 63 | *** |
| 64 | *** |
| 65 | *** |
| 66 | *** |
| 67 | *** |
| 68 | *** |
| 69 | *** |
| 70 | *** |
| 71 | *** |
| 72 | *** |
| 73 | *** |
| 74 | *** |
| 75 | *** |
| 76 | *** |
| 77 | *** |
| 78 | *** |
| 79 | *** |
| 80 | *** |
| 81 | *** |
| 82 | *** |
| 83 | *** |
| 84 | *** |
| 85 | *** |
| 86 | * |
| 87 | *** |
| 88 | *** |
| 89 | *** |
| 90 | *** |
| 91 | *** |
| 92 | *** |
| 93 | *** |
| 94 | *** |
| 95 | *** |
| 96 | *** |
| 97 | *** |
| 98 | *** |
| 99 | — |
| 100 | *** |
| 101 | *** |
| 102 | *** |
| 103 | >500 nM |
| 104 | *** |
| 105 | *** |
| 106 | *** |
| 107 | >500 nM |

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference for all purposes, but not to be regarded as prior art affecting the patentability of the present invention.

We claim:

1. A compound of Formula I:

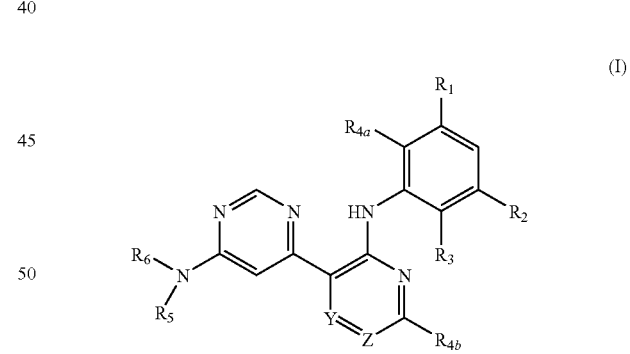

in which:

Z is N and Y is CH;

$R_1$ is $C_{1-4}$alkoxy;

$R_2$ is selected from cyano, $C_{1-4}$alkoxy, —C(O)NR$_7$R$_8$, —NR$_7$C(O)R$_8$, —NR$_7$S(O)$_2$R$_8$, —S(O)$_2$NR$_7$R$_8$, —NR$_7$R$_8$, —C(O)OR$_8$, —OC(O)R$_8$, —C(O)NR$_7$OR$_8$ and a saturated, unsaturated or partially saturated monocyclic ring containing 5 to 7 ring members selected from C, O, N and S; wherein $R_7$ is selected from hydrogen and $C_{1-4}$alkyl; and $R_8$ is selected from hydrogen, $C_{1-4}$alkyl and $C_{3-12}$cycloalkyl, $R_3$ is selected from hydrogen, halo, $C_{1-4}$alkyl and $C_{1-4}$alkoxy;

$R_{4a}$ is selected from halo and $C_{1-4}$alkyl;

$R_{4b}$ is selected from hydrogen and $C_{1-4}$alkyl;

$R_5$ is hydrogen and $C_{1-4}$alkyl;

$R_6$ is selected from hydrogen, —$X_1R_9$ and $X_1NR_{10}R_{11}$; wherein each $X_1$ is independently selected from a bond and $C_{1-4}$alkylene; $R_9$ is selected from $C_{6-10}$aryl, a monocyclic ring containing 5 to 7 ring members selected from C, O, N and S, and a bridged or fused bicyclic ring system containing 8 to 14 members selected from C, O, N and S; wherein said monocyclic and bridged or fused bicyclic rings of $R_9$ can be saturated, unsaturated or partially unsaturated; $R_{10}$ and $R_{11}$ are independently selected from hydrogen and $C_{1-4}$alkyl;

wherein said aryl, monocyclic or bicyclic rings of $R_9$ can be optionally substituted with a group selected from $C_{1-4}$alkyl, —$X_2R_{12}$, and —$OX_2NR_{13}R_{14}$; wherein each $X_2$ is independently selected from a bond and $C_{1-4}$alkylene; $R_{13}$ and $R_{14}$ are independently selected from hydrogen and $C_{1-4}$alkyl; $R_{12}$ is selected from a monocyclic ring containing 5 to 7 ring members selected from C, O, N and S optionally substituted with up to 3 groups selected from $C_{1-4}$alkyl, —$X_3C(O)NR_{15}R_{16}$, —$X_3OR_{16}$, —$X_3C(O)X_3OR_{15}$, —$X_3C(O)R_{15}$ and —$X_3NR_{15}R_{16}$; wherein said monocyclic ring of $R_{12}$ can be saturated, unsaturated or partially unsaturated; wherein each $X_3$ is independently selected from a bond and $C_{1-4}$alkylene; each $R_{15}$ and $R_{16}$ is independently selected from hydrogen and $C_{1-4}$alkyl;

wherein any alkyl substituents of $R_9$ can optionally substituted with up to 3 hydroxyl groups; or a pharmaceutically acceptable salt thereof.

2. The compound of claim 1 wherein $R_2$ is selected from cyano, $C_{1-4}$alkoxy, —$C(O)NR_7R_8$, —$NR_7C(O)R_8$, —$NR_7S(O)_2R_8$, —$S(O)_2NR_7R_8$, —$NR_7R_8$, —$C(O)OR_8$, —$OC(O)R_8$, —$C(O)NR_7OR_8$ and a saturated, unsaturated or partially saturated monocyclic ring containing 5 to 7 ring members selected from C, O, N and S; wherein $R_7$ is selected from hydrogen and $C_{1-4}$alkyl; and $R_8$ is selected from hydrogen, $C_{1-4}$alkyl and $C_{3-12}$cycloalkyl.

3. The compound of claim 1 wherein $R_2$ is selected from phenyl that is unsubstituted or substituted by one or more substituents selected from $C_1$-$C_4$-alkyl, halo-$C_1$-$C_4$-alkyl and (pyrrolidino, piperidino, piperazino or 4-$C_1$-$C_4$-alkylpiperazino)-$C_1$-$C_4$-alkyl.

4. The compound of claim 1 in which Z is N, Y is CH and $R_1$, $R_2$, $R_3$, $R_{4a}$, $R_{4b}$, $R_5$ and $R_6$ are as defined in claim 1.

5. The compound of claim 4 in which:

$R_1$ is $C_{1-4}$alkoxy;

$R_2$ is selected from cyano, $C_{1-4}$alkoxy, —$C(O)NR_7R_8$, —$NR_7C(O)R_8$, —$NR_7S(O)_2R_8$, —$NR_7R_8$, —$C(O)OR_8$, —$C(O)NR_7OR_8$ and a saturated, unsaturated or partially saturated monocyclic ring containing 5 to 7 ring members selected from C, O, N and S; wherein $R_7$ is selected from hydrogen and $C_{1-4}$alkyl; and $R_8$ is selected from hydrogen, $C_{1-4}$alkyl and $C_{3-12}$cycloalkyl;

$R_3$ is selected from hydrogen, halo and $C_{1-4}$alkyl;

$R_{4a}$ is selected from halo and $C_{1-4}$alkyl;

$R_{4b}$ is selected from hydrogen and $C_{1-4}$alkyl;

$R_5$ is hydrogen;

$R_6$ is selected from hydrogen, —$X_1R_9$ and $X_1NR_{10}R_{11}$; wherein each $X_1$ is independently selected from a bond and $C_{1-4}$alkylene; $R_9$ is selected from $C_{6-10}$aryl, a monocyclic ring containing 5 to 7 ring members selected from C, O, N and S, and a bridged or fused bicyclic ring system containing 8 to 14 members selected from C, O, N and S; wherein said monocyclic and bridged or fused bicyclic rings of $R_9$ can be saturated, unsaturated or partially unsaturated; $R_{10}$ and $R_{11}$ are independently selected from hydrogen and $C_{1-4}$alkyl;

wherein said monocyclic and bridged or fused bicyclic rings of $R_9$ can be optionally substituted with a group selected from $C_{1-4}$alkyl, —$X_2R_{12}$, and —$OX_2NR_{13}R_{14}$; wherein each $X_2$ is independently selected from a bond and $C_{1-4}$alkylene; $R_{13}$ and $R_{14}$ are independently selected from hydrogen and $C_{1-4}$alkyl; $R_{12}$ is selected from a monocyclic ring containing 5 to 7 ring members selected from C, O, N and S optionally substituted with up to 3 groups selected from $C_{1-4}$alkyl, —$X_3C(O)NR_{15}R_{16}$, —$X_3OR_{16}$, —$X_3C(O)X_3OR_{15}$, —$X_3C(O)R_{15}$ and —$X_3NR_{15}R_{16}$; wherein said monocyclic and bridged or fused bicyclic rings of $R_{12}$ can be saturated, unsaturated or partially unsaturated; wherein each $X_3$ is independently selected from a bond and $C_{1-4}$alkylene; each $R_{15}$ and $R_{16}$ is independently selected from hydrogen and $C_{1-4}$alkyl;

wherein any alkyl substituents of $R_9$ can optionally substituted with up to 3 hydroxyl groups.

6. The compound of claim 5 in which:

$R_1$ $C_{1-4}$alkoxy;

$R_2$ is selected from H, cyano, $C_{1-4}$alkoxy, —$C(O)NR_7R_8$, —$NR_7C(O)R_8$, —$NR_7S(O)_2R_8$, —$NR_7R_8$, —$C(O)OR_8$, —$C(O)NR_7OR_8$ and a saturated, unsaturated or partially saturated monocyclic ring containing 5 to 7 ring members selected from C, O, N and S; wherein $R_7$ is selected from hydrogen and $C_{1-4}$alkyl; and $R_8$ is selected from hydrogen, $C_{1-4}$alkyl and $C_{3-12}$cycloalkyl;

$R_3$ is selected from hydrogen, halo and $C_{1-4}$alkyl;

$R_{4a}$ is selected from halo and $C_{1-4}$alkyl;

$R_{4b}$ is selected from hydrogen and $C_{1-4}$alkyl;

$R_5$ is hydrogen;

$R_6$ is selected from hydrogen, —$X_1R_9$ and $X_1NR_{10}R_{11}$; wherein each $X_1$ is independently selected from a bond and $C_{1-4}$alkylene; $R_9$ is selected from $C_{6-10}$aryl, a monocyclic ring containing 5 to 7 ring members selected from C, O, N and S, and a bridged or fused bicyclic ring system containing 8 to 14 members selected from C, O, N and S; wherein said monocyclic and bridged or fused bicyclic rings of $R_9$ can be saturated, unsaturated or partially unsaturated; $R_{10}$ and $R_{11}$ are independently selected from hydrogen and $C_{1-4}$alkyl;

wherein said monocyclic and bridged or fused bicyclic rings of $R_9$ can be optionally substituted with a group selected from $C_{1-4}$alkyl, —$X_2R_{12}$, and —$OX_2NR_{13}R_{14}$; wherein each $X_2$ is independently selected from a bond and $C_{1-4}$alkylene; $R_{13}$ and $R_{14}$ are independently selected from hydrogen and $C_{1-4}$alkyl; $R_{12}$ is selected from a monocyclic ring containing 5 to 7 ring members selected from C, O, N and S optionally substituted with up to 3 groups selected from $C_{1-4}$alkyl, —$X_3C(O)NR_{15}R_{16}$, —$X_3OR_{16}$, —$X_3C(O)X_3OR_{15}$, —$X_3C(O)R_{15}$ and —$X_3NR_{15}R_{16}$; wherein said monocyclic and bridged or fused bicyclic rings of $R_{12}$ can be saturated, unsaturated or partially unsaturated; wherein each $X_3$ is independently selected from a bond and $C_{1-4}$alkylene; each $R_{15}$ and $R_{16}$ is independently selected from hydrogen and $C_{1-4}$alkyl;

wherein any alkyl substituents of $R_9$ can optionally substituted with up to 3 hydroxyl groups.

7. The compound of claim 5 in which:
   $R_1$ is methoxy; and
   $R_2$ is selected from cyano, methoxy, ethyl-amino-carbonyl, cyclopropyl-amino-carbonyl, cyclopropyl-carbonyl-amino, methyl-carbonyl-amino, methyl-sulfonyl-amino, amino, methoxy-carbonyl, ethoxy-amino-carbonyl and amino-carbonyl.

8. The compound of claim 6 in which:
   $R_1$ is methoxy; and
   $R_2$ is selected from H, cyano, methoxy, ethyl-amino-carbonyl, cyclopropyl-amino-carbonyl, cyclopropyl-carbonyl-amino, methyl-carbonyl-amino, methyl-sulfonyl-amino, amino, methoxy-carbonyl, ethoxy-amino-carbonyl and amino-carbonyl.

9. The compound of claim 7 in which:
   $R_3$ is selected from hydrogen, chloro, fluoro, bromo and methyl;
   $R_{4a}$ is selected from chloro, fluoro, methyl and oxazole;
   $R_{4b}$ is selected from hydrogen and methyl; and
   $R_5$ is hydrogen.

10. The compound of claim 8 in which:
    $R_3$ is selected from hydrogen, chloro, fluoro, bromo and methyl;
    $R_{4a}$ is selected from chloro, fluoro, methyl and oxazole;
    $R_{4b}$ is selected from hydrogen and methyl; and
    $R_5$ is hydrogen.

11. The compound of claim 9 in which $R_6$ is selected from: hydrogen; morpholino-ethyl; dimethyl-amino-butyl; methyl-piperazinyl-ethyl; pyridinyl substituted with a group selected from morpholino-methyl, amino-carbonyl-piperazinyl-methyl, methyl-carbonyl-piperazinyl-methyl, morpholino-ethyl, piperidinyl-methyl, pyrrolidinyl-methyl, dimethylamino-carbonyl -piperazinyl-methyl, methylamino-carbonyl-piperazinyl-methyl, methyl-piperazinyl-methyl, ethyl-piperazinyl-methyl, hydroxy-ethyl-piperazinyl-methyl, ethyl-piperazinyl, methyl-piperazinyl-ethyl, hydroxy-methyl-carbonyl-piperazinyl, diethyl-amino-methyl and dimethyl-amino-methyl; and phenyl substituted with a group selected from ethyl-piperazinyl, 1-hydroxy-ethyl, morpholino-methyl, diethylamino-ethoxy and morpholino.

12. The compound of claim 10 in which $R_6$ is selected from: hydrogen; morpholino-ethyl; dimethyl-amino-butyl; methyl-piperazinyl-ethyl; pyridinyl substituted with a group selected from morpholino-methyl, amino-carbonyl-piperazinyl-methyl, methyl-carbonyl-piperazinyl-methyl, morpholino-ethyl, piperidinyl-methyl, pyrrolidinyl-methyl, dimethylamino-carbonyl-piperazinyl-methyl, methylamino-carbonyl-piperazinyl-methyl, methyl-piperazinyl-methyl, ethyl-piperazinyl-methyl, hydroxy-ethyl-piperazinyl-methyl, ethyl-piperazinyl, methyl-piperazinyl-ethyl, hydroxy-methyl-carbonyl-piperazinyl, diethyl-amino-methyl and dimethyl-amino-methyl; and phenyl substituted with a group selected from ethyl-piperazinyl, 1-hydroxy-ethyl, morpholino-methyl, diethylamino-ethoxy and morpholino.

13. The compound of claim 1 wherein $R_2$ is —C(O)NR$_7$OR$_8$ wherein $R_7$ is hydrogen or $C_1$-$C_4$-alkyl and $R_8$ is phenyl that is unsubstituted or substituted by one or more substituents selected from $C_1$-$C_4$-alkyl, halo-$C_1$-$C_4$-alkyl and (pyrrolidino, piperidino, piperazino or 4-$C_1$-$C_4$-alkylpiperazino)-$C_1$-$C_4$-alkyl; or is 5-(morpholinomethyl)pyridin-2-ylamino or 6-(5-(2-morpholinoethyl)pyridin-2-ylamino, or a pharmaceutically acceptable salt thereof.

14. The compound of claim 1 selected from N4'-(2,6-Dichloro-3,5-dimethoxy-phenyl)-[4,5']bipyrimidinyl-6,4'-diamine, N4'-(2,6-Dichloro-3,5-dimethoxy-phenyl) -N6-(5-pyrrolidin-1-ylmethyl-pyridin-2-yl)-[4,5']bipyrimidinyl-6,4'-diamine, N4'-(2,6-Dichloro-3,5-dimethoxy-phenyl)-N6-[5-(4-methyl-piperazin-1-ylmethyl)-pyridin-2-yl]-[4,5']bipyrimidinyl-6,4'-diamine, N4'-(2,6-Dichloro-3,5-dimethoxy-phenyl)-N6-(5-morpholin-4-ylmethyl-pyridin-2-yl)-[4,5']bipyrimidinyl-6,4'-diamine, N4'-(2,6-Dichloro-3,5-dimethoxy-phenyl) -N6-(4-morpholin-4-ylmethyl-pyridin-2-yl)-[4,5']bipyrimidinyl-6,4'-diamine, N4'-(2,6-Dichloro-3,5-dimethoxy-phenyl) -N6-[4-(4-methyl-piperazin-1-ylmethyl)-pyridin-2-yl]-[4,5']bipyrimidinyl-6,4'-diamine, N4'-(2,6-Dichloro-3,5-dimethoxy-phenyl)-N6-(5-dimethylaminomethyl-pyridin-2-yl) -[4,5']bipyrimidinyl-6,4'-diamine, 1-[4'-(2,6-Dichloro-3,5-dimethoxy-phenylamino)-[4,5']bipyrimidinyl-6-yl]-3-[2-(4-methyl-piperazin-1-yl)-ethyl]-urea, 1-[4'-(2,6-Dichloro-3,5-dimethoxy-phenylamino)-[4,5']bipyrimidinyl-6-yl]-3-(2-morpholin-4-yl-ethyl)-urea, N4'-(2,6-Dichloro-3,5-dimethoxy-phenyl)-N6-[4-(4-ethyl-piperazin-1-yl)-phenyl]-[4,5']bipyrimidinyl-6,4'-diamine, N4'-(2,6-Dichloro-3,5-dimethoxy-phenyl)-N6-(4-morpholin-4-yl-phenyl) -[4,5']bipyrimidinyl-6,4'-diamine, N4'-(2,6-Dichloro-3,5-dimethoxy-phenyl)-N6-(3-morpholin-4-yl-propyl)-[4,5']bipyrimidinyl-6,4'-diamine, N4'-(2,6-Dichloro-3,5-dimethoxy-phenyl)-N6-(4-dimethylamino-butyl)-[4,5']bipyrimidinyl-6,4'-diamine, N4'-(2,6-Dichloro-3,5-dimethoxy-phenyl)-N6-[2-(4-methyl-piperazin-1-yl)-ethyl]-[4,5']bipyrimidinyl-6,4'-diamine, 4-{6-[4'-(2,6-Dichloro-3,5-dimethoxy-phenylamino)-[4,5']bipyrimidinyl-6-ylamino]-pyridin-3-ylmethyl}-piperazine-1-carboxylic acid amide, 1-(4-{6-[4'-(2,6-Dichloro-3,5-dimethoxy-phenylamino)-[4,5']bipyrimidinyl-6-ylamino]-pyridin-3-ylmethyl}-piperazin-1-yl)-ethanone, N4'-(2,6-Dichloro-3,5-dimethoxy-phenyl)-N6-[4-(2-diethylamino-ethoxy)-phenyl]-[4,5']bipyrimidinyl-6,4'-diamine, N4'-(2,6-Dichloro-3,5-dimethoxy-phenyl)-N6-[5-(2-morpholin-4-yl-ethyl)-pyridin-2-yl]-[4,5']bipyrimidinyl-6,4'-diamine, 4-{6-[4'-(2,6-Dichloro-3,5-dimethoxy-phenylamino)-[4,5']bipyrimidinyl-6-ylamino]-pyridin-3-ylmethyl}-piperazine-1-carboxylic acid dimethylamide, 4-{6-[4'-(2,6-Dichloro-3,5-dimethoxy-phenylamino)-[4,5']bipyrimidinyl-6-ylamino]-pyridin-3-ylmethyl}-piperazine-1-carboxylic acid methylamide, N4'-(2,6-Dichloro-3,5-dimethoxy-phenyl)N6-(5-morpholin-4-ylmethyl-pyridin-3-yl)-[4,5']bipyrimidinyl-6,4'-diamine, N4'-(2,6-Dichloro-3,5-dimethoxy-phenyl)-N6-(5-piperidin-1-ylmethyl-pyridin-2-yl)-[4,5']bipyrimidinyl-6,4'-diamine, 3-(6-Amino-[4,5']bipyrimidinyl-4'-ylamino)-2,4-dichloro-5-methoxy-benzoic acid methyl ester, 2,4-Dichloro-N-ethyl-5-methoxy-3-[6-(5-morpholin-4-ylmethyl-pyridin-2-ylamino)-[4,5']bipyrimidinyl-4'-ylamino]-benzamide, 2,4-Dichloro-N-ethoxy-5-methoxy-3-[6-(5-morpholin-4-ylmethyl-pyridin-2-ylamino)-[4,5']bipyrimidinyl-4'-ylamino]-benzamide, 2,4-Dichloro-5-methoxy-3-[6-(5-morpholin-4-ylmethyl-pyridin-2-ylamino)-[4,5']bipyrimidinyl-4'-ylamino]-benzamide, 2,4-Dichloro-5-methoxy-3-[6-(5-morpholin-4-ylmethyl-pyridin-2-ylamino)-[4,5']bipyrimidinyl-4'-ylamino]-benzoic acid methyl ester, N4'-(2,6-Dichloro-3,5-dimethoxy-phenyl)-N6-(5-diethylaminomethyl-pyridin-2-yl)-[4,5']bipyrimidinyl-6,4'-diamine, 1-{3-[4'-(2,6-Dichloro-3,5-dimethoxy-phenylamino)-[4,5']bipyrimidinyl-6-yl-amino]-phenyl}-ethanol, 2,4-Dichloro-N-ethyl-5-methoxy-3-{6-[4-(4-methyl-piperazin-1-ylmethyl)-pyridin-2-ylamino]-[4,5']bipyrimidinyl-4'-ylamino}-benzamide, 2,4-Dichloro-3-[6-(5-dimethylaminomethyl-pyridin-2-ylamino)-[4,5']bipyrimidinyl-4'-ylamino]-N-ethyl-5-methoxy-benzamide, 2,4-Dichloro-N-ethyl-5-methoxy-3-{6-[5-(2-morpholin-4-yl-ethyl)-pyridin-2-ylamino)-[4,5']bipyrimidinyl-4'-ylamino}-benzamide, 2,4-Dichloro-N-ethyl-5-methoxy-3-[6-(4-morpholin-4-ylmethyl-pyridin-2-ylamino)-[4,5]bipyrimidinyl-4'-ylamino]-benzamide, 2,4-

Dichloro-N-ethyl-5-methoxy-3-{6-[5-(4-methyl-piperazin-1-ylmethyl)-pyridin-2-ylamino]-[4,5']bipyrimidinyl-4'-ylamino}-benzamide, 2,4-Dichloro-N-ethyl-5-methoxy-3-[6-(5-pyrrolidin-1-ylmethyl-pyridin-2-ylamino)-[4,5']bipyrimidinyl-4'-ylamino]-benzamide, 2,4-Dichloro-N-ethyl-3-{6-[4-(4-ethyl-piperazin-1-yl)-phenylamino]-[4,5']bipyrimidinyl-4'-ylamino}-5-methoxy-benzamide, N4'-(2-Chloro-3,5-dimethoxy-phenyl)-N6-(5-morpholin-4-ylmethyl-pyridin-2-yl) -[4,5']bipyrimidinyl-6,4'-diamine, N4'-(2-Chloro-3,5-dimethoxy-phenyl)-N6-[5-(4-ethyl-piperazin-1-ylmethyl)-pyridin-2-yl]-[4,5']bipyrimidinyl-6,4'-diamine, N4'-(2-Chloro-3,5-dimethoxy-phenyl)-N6-[4-(4-methyl-piperazin-1-ylmethyl)-pyridin-2-yl]-[4,5']bipyrimidinyl-6,4'-diamine, N4'-(2,6-Dichloro-3,5-dimethoxy-phenyl)-N6-[5-(4-ethyl-piperazin-1-yl)-pyridin-2-yl]-[4,5']bipyrimidinyl-6,4'-diamine, 2,4-Dichloro-3-{6-[5-(4-ethyl-piperazin-1-yl)-pyridin-2-ylamino]-[4,5']bipyrimidinyl-4'-ylamino}-5-methoxy-benzoic acid methyl ester, 2,4-Dichloro-N-ethyl-3-{6-[5-(4-ethyl-piperazin-1-yl)-pyridin-2-ylamino]-[4,5']bipyrimidinyl-4'-ylamino}-5-methoxy-benzamide, N4'-(2-Chloro-6-fluoro-3,5-dimethoxy-phenyl)-N6-[5-(4-ethyl-piperazin-1-yl)-pyridin-2-yl]-[4,5']bipyrimidinyl-6,4'-diamine, N4'-(2-Chloro-6-fluoro-3,5-dimethoxy-phenyl)-N6-(5-morpholin-4-ylmethyl-pyridin-2-yl)-[4,5']bipyrimidinyl-6,4'-diamine, N4'-(2-Chloro-6-fluoro-3,5-dimethoxy-phenyl)-N6-[5-(4-ethyl-piperazin-1-ylmethyl)-pyridin-2-yl]-[4,5']bipyrimidinyl-6,4'-diamine, N4'-(2-Chloro-6-fluoro-3,5-dimethoxy-phenyl)-N6-(4-morpholin-4-ylmethyl-pyridin-2-yl)-[4,5']bipyrimidinyl-6,4'-diamine, N4'-(2-Bromo-6-chloro-3,5-dimethoxy-phenyl)-N6-[5-(4-ethyl-piperazin-1-yl)-pyridin-2-yl]-[4,5']bipyrimidinyl-6,4'-diamine, N4'-(2-Chloro-3,5-dimethoxy-6-methyl-phenyl)-N6-[5-(4-ethyl-piperazin-1-yl)-pyridin-2-yl]-[4,5']bipyrimidinyl-6,4'-diamine, N4'-(2-Bromo-6-chloro-3,5-dimethoxy-phenyl)-N6-(5-morpholin-4-ylmethyl-pyridin-2-yl)-[4,5']bipyrimidinyl-6,4'-diamine, N4'-(2-Bromo-6-chloro-3,5-dimethoxy-phenyl)-N6-[5-(4-ethyl-piperazin-1-ylmethyl)-pyridin-2-yl]-[4,5']bipyrimidinyl-6,4'-diamine, N4'-(2-Bromo-6-chloro-3,5-dimethoxy-phenyl)-N6-(4-morpholin-4-ylmethyl-pyridin-2-yl)-[4,5']bipyrimidinyl-6,4'-diamine, N4'-(2-Chloro-3,5-dimethoxy-6-methyl-phenyl)-N6-(5-morpholin-4-ylmethyl-pyridin-2-yl)-[4,5']bipyrimidinyl-6,4'-diamine, N4'-(2-Chloro-3,5-dimethoxy-6-methyl-phenyl)-N6-[5-(4-ethyl-piperazin-1-ylmethyl)-pyridin-2-yl]-[4,5']bipyrimidinyl-6,4'-diamine, N4'-(2-Chloro-3,5-dimethoxy-6-methyl-phenyl)-N6-(4-morpholin-4-ylmethyl-pyridin-2-yl)-[4,5']bipyrimidinyl-6,4'-diamine, 2,4-Dichloro-N-cyclopropyl-3-{6-[5-(4-ethyl-piperazin-1-yl)-pyridin-2-ylamino]-[4,5']bipyrimidinyl-4'-ylamino}-5-methoxy-benzamide, N4'-(2-Chloro-6-fluoro-3,5-dimethoxy-phenyl)-N6-[4-(2-morpholin-4-yl-ethyl)-pyridin-2-yl]-[4,5']bipyrimidinyl-6,4'-diamine, 2,4-Dichloro-N-cyclopropyl-5-methoxy-3-[6-(5-morpholin-4-ylmethyl-pyridin-2-ylamino)-[4,5']bipyrimidinyl-4'-ylamino]-benzamide, 2,4-Dichloro-N-cyclopropyl-3-{6-[5-(4-ethyl-piperazin-1-ylmethyl)-pyridin-2-ylamino]-[4,5']bipyrimidinyl-4'-ylamino}-5-methoxy-benzamide, N4'-(2-Chloro-6-fluoro-3,5-dimethoxy-phenyl)-N6-[4-(4-ethyl-piperazin-1-yl)-phenyl]-[4,5']bipyrimidinyl-6,4'-diamine, N4'-(2-Chloro-6-fluoro-3,5-dimethoxy-phenyl)-N6-(4-pyrrolidin-1-ylmethyl-pyridin-2-yl)-[4,5']bipyrimidinyl-6,4'-diamine, 1-(4-{6-[4'-(2-Chloro-6-fluoro-3,5-dimethoxy-phenylamino)-[4,5']bipyrimidinyl-6-ylamino]-pyridin-3-ylmethyl}-piperazin-1-yl)-ethanone, N4'-(2,6-Difluoro-3,5-dimethoxy-phenyl)-N6-[5-(4-ethyl-piperazin-1-yl)-pyridin-2-yl]-[4,5']bipyrimidinyl-6,4'-diamine, N4'-(2,6-Difluoro-3,5-dimethoxy-phenyl)-N6-(5-morpholin-4-ylmethyl-pyridin-2-yl)-[4,5']bipyrimidinyl-6,4'-diamine, N4'-(2,6-Difluoro-3,5-dimethoxy-phenyl)-N6-[5-(4-ethyl-piperazin-1-ylmethyl)-pyridin-2-yl]-[4,5']bipyrimidinyl-6,4'-diamine, N4'-(2,6-Difluoro-3,5-dimethoxy-phenyl)-N6-(4-morpholin-4-ylmethyl-pyridin-2-yl) -[4,5']bipyrimidinyl-6,4'-diamine, 1-(4-{6-[4'-(2,6-Difluoro-3,5-dimethoxy-phenylamino)-[4,5']bipyrimidinyl-6-ylamino]-pyridin-3-ylmethyl}-piperazin-1-yl)-ethanone, 3-{6-[5-(4-Acetyl-piperazin-1-ylmethyl)-pyridin-2-ylamino]-[4,5']bipyrimidinyl-4'-ylamino}-2,4-dichloro-N-cyclopropyl-5-methoxy-benzamide, N4'-(2-Fluoro-3,5-dimethoxy-phenyl)-N6-(5-morpholin-4-ylmethyl-pyridin-2-yl)-[4,5']bipyrimidinyl-6,4'-diamine, N6-[5-(4-Ethyl-piperazin-1-ylmethyl)-pyridin-2-yl]-N4'-(2-fluoro-3,5-dimethoxy-phenyl)-[4,5']bipyrimidinyl-6,4'-diamine, 2-(4-{6-[4'-(2-Fluoro-3,5-dimethoxy-phenylamino)-[4,5']bipyrimidinyl-6-ylamino]-pyridin-3-ylmethyl}-piperazin-1-yl)-ethanol, N4'-(2-Fluoro-3,5-dimethoxy-phenyl)-N6-(4-morpholin-4-ylmethyl-pyridin-2-yl)-[4,5']bipyrimidinyl-6,4'-diamine, N6-[5-(4-Ethyl-piperazin-1-yl)-pyridin-2-yl]-N4'-(2-fluoro-3,5-dimethoxy-phenyl)-[4,5']bipyrimidinyl-6,4'-diamine, 2-(4-{6-[4'-(2-Chloro-6-fluoro-3,5-dimethoxy-phenylamino)-[4,5']bipyrimidinyl-6-ylamino]-pyridin-3-ylmethyl}-piperazin-1-yl)-ethanol, 2-(4-{6-[4'-(2,6-Difluoro-3,5-dimethoxy-phenylamino)-[4,5']bipyrimidinyl-6-ylamino]-pyridin-3-ylmethyl}-piperazin-1-yl)-ethanol, 2-(4-{6-[4'-(2,6-Dichloro-3,5-dimethoxy-phenylamino)-[4,5']bipyrimidinyl-6-ylamino]-pyridin-3-Ylmethyl}-piperazin-1-yl)-ethanol, 2-(4-{6-[4'-(2-Chloro-3,5-dimethoxy-6-methyl-phenylamino)-[4,5']bipyrimidinyl-6-ylamino]-pyridin-3-ylmethyl}-piperazin-1-yl)-ethanol, 1-{3-[4'-(2-Chloro-6-fluoro-3,5-dimethoxy-phenylamino)-[4,5']bipyrimidinyl-6-ylamino]-phenyl}-ethanol, 1-{3-[4'-(2,6-Difluoro-3,5-dimethoxy-phenylamino)-[4,5']bipyrimidinyl-6-ylamino]-phenyl}-ethanol, 1-{6-[4'-(2-Chloro-6-fluoro-3,5-dimethoxy-phenylamino)-[4,5']bipyrimidinyl-6-ylamino]-pyridin-3-yl}-ethanol, 1-{6-[4'-(2,6-Difluoro-3,5-dimethoxy-phenylamino)-[4,5']bipyrimidinyl-6-ylamino]-pyridin-3-yl}-ethanol, 1-{6-[4'-(2-Chloro-3,5-dimethoxy-6-methyl-phenylamino)-[4,5']bipyrimidinyl-6-ylamino]-pyridin-3-yl}-ethanol, 1-{6-[4'-(2,6-Dichloro-3,5-dimethoxy-phenylamino)-[4,5']bipyrimidinyl-6-ylamino]-pyridin-3-yl}-ethanol, 1-{6-[4'-(2-Fluoro-3,5-dimethoxy-phenylamino)-[4,5']bipyrimidinyl-6-ylamino]-pyridin-3-yl}-ethanol, N4'-(2-Fluoro-3,5-dimethoxy-phenyl)-N6-[5-(2-morpholin-4-yl-ethyl)-pyridin-2-yl]-[4,5']bipyrimidinyl-6,4'-diamine, N4'-(2,6-Difluoro-3,5-dimethoxy-phenyl)-N6-[5-(2-morpholin-4-yl-ethyl)-pyridin-2-yl]-[4,5']bipyrimidinyl-6,4'-diamine, N4'-(2-Chloro-3,5-dimethoxy-6-methyl-phenyl)-N6-[5-(2-morpholin-4-yl-ethyl)-pyridin-2-yl]-[4,5']bipyrimidinyl-6,4'-diamine, 1-(4-{6-[4'-(2,6-Dichloro-3,5-dimethoxy-phenylamino)-[4,5']bipyrimidinyl-6-ylamino]-pyridin-3-ylmethyl}-piperazin-1-yl)-2-hydroxy-ethanone, 1-(4-{6-[4'-(2-Chloro-6-fluoro-3,5-dimethoxy-phenyl-amino)-[4,5']bipyrimidinyl-6-ylamino]-pyridin-3-ylmethyl}-piperazin-1-yl)-2-hydroxy-ethanone, and N4'-(2-Chloro-6-fluoro-3,5-dimethoxy-phenyl)-2'-methyl-N6-(5-morpholin-4-ylmethyl-pyridin-2-yl)-[4,5']bipyrimidinyl-6,4'-diamine; or a pharmaceutically acceptable salt thereof.

15. A compound selected from the group consisting of 2,4-dichloro-5-methoxy-3-(6-(5-(morpholinomethyl)pyridin-2-ylamino)-4,5'-bipyrimidin-4'-ylamino)-N-(3-(trifluoromethyl)phenyl)benzamide, 2,4-dichloro-N-(4-((4-ethylpiperazin-1-yl)methyl)-3-(trifluoromethyl)phenyl)-5-methoxy-3-(6-(5-(morpholinomethyl)pyridin-2-ylamino)-4,5'-bipyrimidin-4'-ylamino)benzamide, {6-[3-(2,6-Dichloro- 3,5-dimethoxy-phenylamino)-pyrazin-2-yl]-pyrimidin-4-yl}-(5-morpholin-4-ylmethyl-pyridin-2-yl) -amine, {6-[3-(2-chloro-3,5-dimethoxy-6-fluoro phenylamino)-pyrazin-2-yl]-pyrimidin-4-yl}-(5-morpholin-4-ylmethyl-pyridin-2-yl)-amine, {6-[3-(2,6-Dichloro-3,5-dimethoxy-phenylamino)-pyrazin-2-yl]-pyrimidin-4-yl}-(4-morpholin-4-ylmethyl-pyridin-2-yl)-amine, {6-[3-(2-chloro-3,5-dimethoxy-6-fluoro phenylamino)-pyrazin-2-yl]-pyrimidin-4-yl}-(4-morpholin-4-ylmethyl-pyridin-2-yl)-amine, {6-[3-(2,6-Dichloro-3,5-dimethoxy-phenylamino)-pyrazin-2-yl]-pyrimidin-4-yl}-(4-[2-(morpholin-4-yl)-ethyl]-pyridin-2-yl)-amine, {6-[3-(2-chloro-3,5-dimethoxy-6-fluorophenylamino)-pyrazin-2-yl]-pyrimidin-4-yl}-(4-[2-(morpholin-4-yl)-ethyl]-pyridin-2-yl)-amine, {6-[3-(2,6-Dichloro-3,5-dimethoxy-phenylamino)-pyrazin-2-yl]-pyrimidin-4-yl}-(5-[1-(2-hydroxyethyl)-piperazin-4-yl]-pyridin-2-yl)-amine, {6-[3-(2,6-Dichloro-3,5-dimethoxy-phenylamino)-pyrazin-2-yl]-pyrimidin-4-yl}-(5-[1-(2-hydroxy-1-oxo-ethyl)-piperazin-4-yl]-pyridin-2-yl)-amine, {6-[3-(2,6-Dichloro-3,5-dimethoxy-phenylamino)-pyrazin-2-yl]-pyrimidin-4-yl}-(5-[1-hydroxyethyl]-pyridin-2-yl)-amine, {6-[3-(2,6-Difluoro-3-methoxy-phenylamino)-pyrazin-2-yl]-pyrimidin-4-yl}-amine, {6-[3-(2,6-Difluoro-3-methoxy-phenylamino)-pyrazin-2-yl]-pyrimidin-4-yl}-N-(5-(morpholin-4-ylmethyl)-pyridin-2-yl)-amine, {6-[3-(2,6-Difluoro-3-methoxy-phenylamino)-pyrazin-2-yl]-pyrimidin-4-yl}-(4-(morpholin-4-ylmethyl)-pyridin-2-yl)-amine, 6-(3-(2,6-dichlorophenylamino)pyrazin-2-yl)pyrimidin-4-amine, 6-(3-(2,6-dichlorophenylamino)pyrazin-2-yl)-N-(5-(morpholinomethyl)pyridin-2-yl)pyrimidin-4-amine, 6-(3-(2,6-dichlorophenylamino)pyrazin-2-yl)-N-(5-(2-morpholinoethyl)pyridin-2-yl)pyrimidin-4-amine, 6-(3-(2,6-dichlorophenylamino)pyrazin-2-yl)-N-(4-(4-ethylpiperazin-1-yl)phenyl)pyrimidin-4-amine, and 6-(3-(2,6-dichlorophenylamino)pyrazin-2-yl)-N-(4-(2-(diethylamino)ethoxy)phenyl)pyrimidin-4-amine, or a pharmaceutically acceptable salt thereof.

16. A pharmaceutical composition comprising a therapeutically effective amount of a compound of claim 1, in combination with a pharmaceutically acceptable excipient.

17. A method for treating bladder cancer in an animal comprising administering to the animal a therapeutically effective amount of a compound according to claim 1, or a pharmaceutically acceptable salt thereof.

18. A method for treating cervical cancer in an animal comprising administering to the animal a therapeutically effective amount of a compound according to claim 1, or a pharmaceutically acceptable salt thereof.

19. A method for treating multiple myeloma in an animal comprising administering to the animal a therapeutically effective amount of a compound according to claim 1, or a pharmaceutically acceptable salt thereof.

* * * * *